United States Patent
Koizumi et al.

(10) Patent No.: US 10,813,920 B2
(45) Date of Patent: Oct. 27, 2020

(54) DRUG FOR TREATING CORNEAL ENDOTHELIUM BY PROMOTING CELL PROLIFERATION OR INHIBITING CELL DAMAGE

(71) Applicant: THE DOSHISHA, Kyoto (JP)

(72) Inventors: Noriko Koizumi, Kyotanabe (JP); Naoki Okumura, Kyotanabe (JP); Shigeru Kinoshita, Kyoto (JP)

(73) Assignee: THE DOSHISHA, Kyoto-shi, Kyoto (JP)

( * ) Notice: Subject to any disclaimer, the term of this patent is extended or adjusted under 35 U.S.C. 154(b) by 188 days.

(21) Appl. No.: 15/034,710

(22) PCT Filed: Nov. 13, 2014

(86) PCT No.: PCT/JP2014/080831
§ 371 (c)(1),
(2) Date: May 5, 2016

(87) PCT Pub. No.: WO2015/072580
PCT Pub. Date: May 21, 2015

(65) Prior Publication Data
US 2016/0331736 A1    Nov. 17, 2016

(30) Foreign Application Priority Data

Nov. 14, 2013 (JP) .................. 2013-235768

(51) Int. Cl.
| A61K 31/4439 | (2006.01) |
| A61K 31/455 | (2006.01) |
| A61K 31/167 | (2006.01) |
| A61K 31/437 | (2006.01) |
| A61K 31/44 | (2006.01) |
| A61K 31/4418 | (2006.01) |
| A61K 31/5377 | (2006.01) |
| A61K 31/4155 | (2006.01) |

(52) U.S. Cl.
CPC ........ *A61K 31/4439* (2013.01); *A61K 31/167* (2013.01); *A61K 31/4155* (2013.01); *A61K 31/437* (2013.01); *A61K 31/44* (2013.01); *A61K 31/4418* (2013.01); *A61K 31/5377* (2013.01)

(58) Field of Classification Search
None
See application file for complete search history.

(56) References Cited

U.S. PATENT DOCUMENTS

| 7,662,389 | B2 | 2/2010 | Clark et al. | |
| 2005/0119262 | A1* | 6/2005 | Wax | A61K 31/535 |
| | | | | 514/235.5 |
| 2006/0189541 | A1* | 8/2006 | Gamache | A61K 31/192 |
| | | | | 514/20.8 |
| 2008/0119498 | A1* | 5/2008 | Kato | A61K 9/0048 |
| | | | | 514/269 |
| 2009/0202534 | A1 | 8/2009 | Fleenor et al. | |
| 2009/0232772 | A1 | 9/2009 | Amano et al. | |
| 2010/0028328 | A1 | 2/2010 | Reiff et al. | |
| 2010/0144755 | A1 | 6/2010 | Corsi et al. | |
| 2010/0209402 | A1* | 8/2010 | Koizumi | A61K 9/0048 |
| | | | | 424/93.7 |
| 2015/0044178 | A1* | 2/2015 | Kinoshita | C12N 5/0621 |
| | | | | 424/93.7 |
| 2016/0296505 | A1 | 10/2016 | Koizumi et al. | |
| 2018/0369220 | A1 | 12/2018 | Koizumi et al. | |

FOREIGN PATENT DOCUMENTS

| EP | 1 548 008 A1 | 6/2005 |
| EP | 1 669 367 A1 | 6/2006 |
| EP | 1835023 | 9/2007 |
| EP | 2034838 | 3/2009 |
| EP | 2799537 | 5/2014 |
| EP | 3 064 222 A1 | 9/2016 |
| JP | 2006-508169 A | 3/2006 |
| JP | 2006-188496 A | 7/2006 |
| JP | 2006187281 | 7/2006 |
| JP | 2007-525204 A | 9/2007 |
| JP | 2009-539977 A | 11/2009 |
| JP | 2009542816 | 12/2009 |
| JP | 2010-513563 A | 4/2010 |

(Continued)

OTHER PUBLICATIONS

Awad et al., Growth Regulation via p38 Mitogen-activated Protein Kinase in Developing Liver, The Journal of Biological Chemistry, vol. 275, No. 49, Issue of Dec. 8, pp. 38716-38721 (Year: 2000).*

(Continued)

*Primary Examiner* — Louise W Humphrey
*Assistant Examiner* — Srikanth Patury
(74) *Attorney, Agent, or Firm* — Foley & Lardner LLP

(57) ABSTRACT

Provided is an agent for treating or preventing a corneal endothelial disorder wherein cell proliferation is required. More specifically, provided is an agent for treating or preventing a corneal endothelial disorder, wherein cell proliferation is required, said agent comprising a p38MAP kinase inhibitor. In a preferred embodiment, the corneal endothelial disorder is a wound. In a preferred embodiment, the p38MAP kinase inhibitor is soluble in water. The p38MAP kinase inhibitor may comprise 4-(4-fluorophenyl)-2-(4-methylsulfinylphenyl)-5-(4-pyridyl)-1H-imidazole (SB203580) or a salt thereof.

3 Claims, 26 Drawing Sheets
(7 of 26 Drawing Sheet(s) Filed in Color)
Specification includes a Sequence Listing.

(56) References Cited

FOREIGN PATENT DOCUMENTS

| | | |
|---|---|---|
| JP | 2011-518828 A | 6/2011 |
| JP | 2013-520405 A | 6/2013 |
| WO | WO-2004/018430 A1 | 3/2004 |
| WO | WO-2004/060388 A1 | 7/2004 |
| WO | 2006092894 | 9/2006 |
| WO | 2007147103 | 12/2007 |
| WO | WO-2011/101478 A1 | 8/2011 |
| WO | WO-2012/009171 A2 | 1/2012 |
| WO | WO-2012/167143 A1 | 12/2012 |
| WO | 2013100208 | 7/2013 |
| WO | WO-2015/015655 A1 | 2/2015 |
| WO | WO-2015/064768 A1 | 5/2015 |
| WO | WO-2015/072580 A1 | 5/2015 |

OTHER PUBLICATIONS

Funaki et al., Smad7 Suppresses the Inhibitory Effect of TGF-beta2 on corneal endothelial cell proliferation and accelerates corneal endothelial wound closure in vitro, Cornea, 22(2): 153-159 (Year: 2003).*

Huh et al., Distribution of TGF-beta isoforms and signaling intermediates in corneal fibrotic wound repair, Journal of Cellular Biochemistry, 108:476-488,2009 (Year: 2009).*

Okumura et al., The new therapeutic concept of using a Rho kinase inhibitor for the treatment of corneal endothelial dysfunction, Cornea, vol. 30, No. 10, Supplement 1, p. S54-S59, Oct. 2011 (Year: 2011).*

Colby, Medical treatment of Fuch's Dystrophy in our lifetime, IOVS, 2013.*

Fuch's—Dystrophy, Medline Plus Article, 2014.*

Kaufman, The coreal endothelium in intraocular surgery, Journal of Royal Society of Medicine, vol. 73, Mar. 1980.*

Okumura'09, Okumura et a., Enhancement on Primate Corneal Endothelial Cell Survival In Vitro by a ROCK inhibitor, IOVS, Aug. 2009, vol. 50 , No. 8, p. 3680-3687.*

SB203580, Product Catalog, Webpage, SelleckChem.com, 2020 (Year: 2020).*

Song, J. et al. "Induction of FGF-2 Systhesis by IL-1β in Aqueous Humor through P13-Kinase and p38 in Rabbit Corneal Endothelium." Investigative Ophthalmology & Visual Science, vol. 51, No. 2, Feb. 2010, pp. 822-829.

Extended European Search Report dated Jul. 17, 2017 in related European Appl. 14861468.8 (8 pgs.).

Shivanna M. et al., "Barrier dysfunctional of the corneal endothelium in response to the TNF-alpha: role of p38 MAP kinase", IOVS, 2010, vol. 51, No. 3, p. 1575-1582 particularly, abstract, p. 1575, right column, 3rd paragraph, p. 1577, right column, lines 17 to 21.

Rajashekhar G. et al., "Role of MMP-9 in the breakdown of barrier integrity of the corneal endothelium in response to TNF-α", Experimental Eye Research, Mar. 2014, vol. 122, p. 77-85.

International Search Report and Written Opinion issued in connection with PCT/JP2014/080831.

Adachi et al., "Contribution of p38 MAPK, NF-KB and glucocorticoid signaling pathways to ER stress-induced increase in retinal endothelial permeability," Archives of Biochemistry and Biophysics, (Jan. 2012) vol. 520,No. 1, pp. 30-35.

Azizi et al., "p53-Regulated Increase in Oxidative-Stress-Induced Apoptosis in Fuchs Endothelial Corneal Dystrophy: A Native Tissue model," Investigative Ophthalmology & Visual Science, (Dec. 2011), vol. 52, No. 13, pp. 9291-9297.

Corwin et al., "The unfolded protein response in human corneal endothelial cells following hypothermic storage: Implications of a novel stress pathway," Cryobiology (Apr. 2011) vol. 63, No. 1, pp. 46-55.

Huang et al., "Endoplasmic reticulum stress-induced hepatic stellate cell apoptosis through calcium-mediated JNK/P38 MAPK and Calpain/Caspase-12 pathways," Molecular Cellular Biochemistry (Jun. 2014) vol. 394, pp. 1-12.

Kelliher et al., "A cellular model for the investigation of Fuchs' Endothelial Corneal Dystrophy," Experimental Eye Research (2011) vol. 93, pp. 880-888.

Kim et al., "p38 Mitogen-Activated Protein Kinase is Involved in Endoplasmic Reticulum Stress-Induced Cell Death and Autophagy in Human Gingival Fibroblasts," Biological & Pharmaceutical Bulletin (2010) vol. 33, No. 4. pp. 545-549.

Kopplin et al., "Relationship of Fuchs Endothelial Corneal Dystrophy Severity to Central Corneal Thickness," Arch Opthalmol. vol. 130(4):433-439 (Apr. 2012).

Office Action dated May 1, 2020 in U.S. Appl. No. 16/062,045 (US 2018-0369220).

Office Action dated Jan. 17, 2020 in U.S. Appl. No. 16/062,045 (US 2018-0369220).

Yang et al., "Functional Roles of p38 Mitogen-Activated Protein Kinase in Macrophage-Mediated Inflammatory Responses," Mediators of Inflammation, vol. 2011, Article ID 352371, 13 pages (Mar. 2014).

Zaniolo et al., "Culture of human corneal endothelial cells isolated from corneas with Fuchs endothelial corneal dystrophy," Experimental Eye Research, vol. 94 (2012) pp. 22-31.

* cited by examiner

| Name | Concentration (μM) |
|---|---|
| SB203580 | 10 |
| BIRB 796 | 3 |
| PH-797804 | 1 |
| VX-702 | 3 |
| LY2228820 | 3 |
| TAK-715 | 3 |

Scale bar: 100μm

DRUG FOR TREATING CORNEAL ENDOTHELIUM BY PROMOTING CELL PROLIFERATION OR INHIBITING CELL DAMAGE

CROSS REFERENCE TO RELATED APPLICATIONS

This application is a U.S. National Phase Application under 35 U.S.C. § 371 of International Patent Application PCT/JP2014/080831 filed Nov. 13, 2014 which claims priority to Japanese Patent Application No. 2013-235768 filed Nov. 14, 2013. The contents of the foregoing applications are hereby incorporated by reference in their entireties.

TECHNICAL FIELD

The present invention relates to a technique and a method for culturing corneal endothelial cells in a normal state and an agent and a medium therefor.

BACKGROUND ART

Visual information is recognized when light transmitted into the cornea, which is a transparent tissue at the front-most part of an eye ball, reaches the retina and excites nerve cells of the retina, and a generated electric signal is transmitted through the optic nerve to the visual cortex of the cerebrum. To attain good vision, it is necessary that the cornea is transparent. The transparency of the cornea is maintained by maintaining constant water content with pumping and barrier functions of corneal endothelial cells.

Human corneal endothelial cells are present at a density of about 3000 cell per 1 $mm^2$ at birth. However, once damaged, corneal endothelial cells do not have the ability to regenerate. Corneal endothelial dystrophy or bullous keratopathy induced by corneal endothelial dysfunction due to various causes results in edema or turbidity of the cornea, leading to significant deterioration in vision. Currently, penetrating keratoplasty is performed to transplant the entire three layer structure consisting of epithelium, stroma, and endothelium of the cornea for bullous keratopathy. However, there is a shortage of cornea donation in Japan. While there are about 2600 patients waiting for a corneal transplantation, the number of corneal transplantations performed domestically is about 1700 annually.

The cornea is a transparent tissue, which is positioned in the front side of an eyeball and has a three layer structure consisting mainly of a corneal epithelial cell layer, a corneal stroma layer, and a corneal endothelial cell layer. The corneal endothelial cell layer is a single-layer cell layer present in the deeper part of the cornea. The corneal endothelial cell layer has barrier and pumping functions and plays a role in maintaining the transparency of the cornea by maintaining a constant amount of moisture in the cornea. Further, it is known that corneal endothelial cells do not grow in a living organism even if they are damaged. In addition, it is known that a decrease in the number of corneal endothelial cells from damage due to trauma, disease or the like to the cells leads to severe visual impairment.

Patent Literature 1 is a summary of topical therapy for diseases on an ocular surface. Non Patent Literature 1 describes the effect of an inhibitor of p38 on cryotreatment in a corneal endothelium. Non Patent Literature 2 describes the effect of P38 MAP kinase on a TNFα induced loss of barrier function (integrity) in endothelia. Non Patent Literatures 3 and 4 describe treatment methods of corneal epithelial cells utilizing p38 kinase. Non Patent Literature 5 describes the involvement of p38 MAP kinase signals in the process of fibrotic wound repair. Non Patent Literature 6 describes the relationship between MAP kinase and migration of corneal endothelial cells. Non Patent Literature 7 describes the relationship between a corneal endothelial disorder and TNFβ. Non Patent Literature 8 describes the relationship between regenerative healing of corneal wound and TNFβ. Non Patent Literature 9 describes the relationship between corneal endothelial cells and TNFβ.

CITATION LIST

Patent Literature

[PTL 1] Japanese National Phase PCT Laid-open Publication No. 2009-539977

Non Patent Literature

[NPL 1] Song J S et al., Invest. Ophthalmol. Vis. Sci. 51 (2), 822-829 2010
[NPL 2] Shivanna M et al., Invest. Ophthalmol. Vis. Sci. 51 (3), 1575-1582 2010
[NPL 3] Li C. et al., J Cell Physiol Vol. 226, No. 9, Page. 2429-2437 (2011)
[NPL 4] Kang M G et al., J Biol Chem Vol. 278, No. 24, Page. 21989-21997 (2003)
[NPL 5] Sharma G D et al., J Cell Biochem Vol. 108, No. 2, Page. 476-488 (2009)
[NPL 6] Joko et al., Programs and Proceedings of Japan Cornea Conference/Keratoplasty Society of Japan Vol. 32nd-44th, Page. 55 (2008)
[NPL 7] http://kaken.nii.ac.jp/d/p/21791705/2009/3/ja.ja.html, downloaded on Nov. 6, 2013
[NPL 8] Mi H. et al., Histol Histopathol. 2009 November; 24 (11): 1405-16
[NPL 9] Joko T. et al., Exp Eye Res. 2013 March; 108: 23-32

SUMMARY OF INVENTION

Solution to Problem

The inventors have discovered that a p38 MAP kinase inhibitor can be used to treat or prevent a corneal endothelial disorder requiring cell proliferation to arrive at the completion of the present invention. Thus, the present invention representatively provides the following.

(1) A therapeutic or prophylactic drug for a corneal endothelial disease, disorder or condition requiring cell proliferation, suppression of a cellular disorder or suppression of cellular senescence, comprising a p38 MAP kinase inhibitor.
(2) The therapeutic or prophylactic drug of item (1), wherein the corneal endothelial disorder is at least one selected from the group consisting of Fuchs' endothelial corneal dystrophy, sustained decrease in corneal endothelial density after corneal transplantation, trauma, ophthalmic surgery, aging, and disorder associated with corneal endotheliitis.
(3) The therapeutic or prophylactic drug of item (1) or (2), wherein the p38 MAP kinase inhibitor is water-soluble.
(4) The therapeutic or prophylactic drug of any one of items (1)-(3), wherein the p38 MAP kinase inhibitor comprises at least one selected from the group consisting of 4-(4-fluorophenyl)-2-(4-hydroxyphenyl)-5-(4-pyridyl)-1H-imidazole (SB-202190), trans-4-[4-(4-fluorophenyl)-5-(2-methoxy-4-pyrimidinyl)-1H-imidazole-1-yl]cyclohexanol (SB-239063), 4-(4-fluorophenyl)-2-(4-methylsulfinylphenyl)-5-

(4-pyridyl)-1H-imidazole (SB-203580), 4-(4-fluorophenyl)-5-(2-methoxypyrimidine-4-yl)-1-(piperidine-4-yl)imidazole (SB-242235), 4-(4-fluorophenyl)-2-(4-hydroxy-1-butynyl)-1-(3-phenylpropyl)-5-(4-pyridyl)imidazole (RW3-67657), 4-(4-fluorophenyl)-1-(piperidine-4-yl)-5-(4-pyridyl)imidazole (HEP-689), (S)-2-(2-amino-3-phenylpropylamino)-1-methyl-5-(2-naphthyl)-4-(4-pyridyl)-pyrimidine-6-one (AMG-548), 2-chloro-4-(4-fluoro-2-methylanilino)-2'-methylbenzophenone (EO-1606), 3-(4-chlorophenyl)-5-(1-hydroxyacetylpiperidine-4-yl)-4-(pyrimidine-4-yl)-pyrazole (SD-06), 5-(2,6-dichlorophenyl)-2-(2,4-difluorophenylthio) pyrimido[3,4-b]pyridazine-6-one (VX-745), 4-acetylamino-N-tert-butylbenzamide (CPI-1189), N-[3-tert-butyl-1-(4-methylphenyl)pyrazole-5-yl)-N'-[4-(2-morpholinoethoxy)-1-naphthyl]urea (Doramapimod), 2-benzamide-4-[2-ethyl-4-(3-methylphenyl)thiazole-5-yl]pyridine (TAK-715), Talmapimod (SCIO-469), 1-(carbamoyl-6-(2,4-difluorophenyl)pyridine-2-yl)-1-(2,6-difluorophenyl)urea (VX-702); 2-(2,4-difluorophenyl)-6-(1-(2,6-difluorophenyl)ureido) nicotinamide), dilmapimod (GSK-681323), 4-(5-(cyclopropylcarbamoyl)-2-methylphenylamino)-5-methyl-N-propylpyrrolo-(1,2-f)(1,2,4)triazine-6-carboxamide (PS-540446), 4-[3-(4-chloro-phenyl)-5-(1-(2-hydroxy-1-oxoethyl)-pyperizine-4-yl)-pyrazo-4-yl]-pyrimidine (SC-80036), AVE-9940, [5-amino-1-(4-fluorophenyl)-1H-pyrazole-4-yl][3-(3-amino-2-hydroxypropoxy-)phenyl]methanone (RO-3201195), 1-(1,3-dihydroxyprop-2-yl)-4-(4-fluorophenyl)-5-(2-phenoxypyrimidine-4-yl]imidazole (SB-281832), 2-[5-({4-[(4-fluorophenyl)methyl]piperidine-1-yl}carbonyl)-6-methoxy-1-methyl-1H-indole-3-yl]-N,N'-dimethyl-2-oxoacetamide (SCIO-323), 2-(5-tertbutyl-2-m-tolyl-2H-pyrazole-3-yl)-2-hydroxyimide-N-[4-(2-morpholine-4-ylethoxy)-naphthalene-1-yl]-acetamide (KC-706), N,N'-bis[3,5-bis[1-(2-amidinohydrazono)ethyl]phenyl]decandiamide, N,N'-bis[3,5-bis[1-[2-(aminoiminomethyl)hydrazono]ethyl] phenyl]decandiamide (Semapimod), 3-(3-bromo-4-((2,4-difluorobenzyl)oxy)-6-methyl-2-oxopyridine-1(2H)-yl)-N-,4-dimethylbenzamide (PH-797804), and 5-(2-(tert-butyl)-5-(4-fluorophenyl)-1H-imidazole-4-yl)-3-neopentyl-3H-imidazo[4,5-b]pyridine-2-amine (LY2228820).

(5) The therapeutic or prophylactic drug of any one of items (1)-(4), wherein the p38 MAP kinase inhibitor is 4-(4-fluorophenyl)-2-(4-methylsulfinylphenyl)-5-(4-pyridyl)-1H-imidazole (SB203580) or a salt thereof.

(6) The therapeutic or prophylactic drug of any one of items (1)-(5), wherein the p38 MAP kinase inhibitor comprises 4-(4-fluorophenyl)-2-(4-methylsulfinylphenyl)-5-(4-pyridyl)-1H-imidazole (SB203580) hydrochloride.

(7) A p38 MAP kinase inhibiting substance for treatment or prevention of a corneal endothelial disorder requiring cell proliferation.

(8) A method of treating or preventing a corneal endothelial disorder requiring cell proliferation, comprising the step of administering an effective amount of a p38 MAP kinase inhibitor to a subject in need thereof.

It is understood that the present invention can be provided as further combination of one or more of the aforementioned features in addition to the explicitly shown combinations. Further embodiments and advantages of the present invention are recognized by those skilled in the art by reading the understanding the following Detailed Description as needed.

Advantageous Effects of Invention

The present invention provides a technique that can prevent or heal a corneal endothelial disorder, which has been difficult to achieve. In particular, Non Patent Literatures 1 and 2 analyze the role of p38 MAP kinase in corneal endothelium in a special system such as cryotreatment or TNFα induced loss of barrier function (integrety) and explain the effects of inhibitors. However, an effect in a corneal endothelial disorder requiring cell proliferation such as wound (trauma) could not be predicted. In particular, as shown in the Examples and the like, it is understood that recovery from a wound or the like is extremely prominent with the present invention. In addition, the effect healing is more prominent relative to conventional medications, and the present invention is useful as eye drops. Further, although not wishing to be bound by any theory, it is understood that the cellular disorder suppressing effect demonstrated in the Examples could not be expected from conventional techniques and is useful in a disease in which a cellular disorder continuously progresses such as corneal endotheliitis after corneal transplantation or Fuchs' corneal endothelial dystrophy.

BRIEF DESCRIPTION OF DRAWINGS

The patent or application file contains drawings executed in color. Copies of this patent or patent application publication with color drawings will be provided by the Office upon request and payment of the necessary fee.

FIG. 25 is a result of Annexin V and DAPI staining. Green staining indicates Annexin V, and blue staining indicates DAPI staining. The top row, from the left, shows UV (100 J/m$^2$) irradiation (DMSO as a control), VX-702, and PH-797804. The middle row shows SB203580 and LY2228820. The bottom row shows BIRB796 and TAK-715. The concentration used was 10 µM for SB203580, 1 µM for Semapimod, 3 µM for BIRB796, 1 µM for PH-797804, 3 µM for VX-702, 3 µM for LY2228820, and 3 µM for TAX-715. Apoptosis induced by UV was suppressed by all p38 MAPK inhibitors that were used. The scale bar indicates 100 µm.

DESCRIPTION OF EMBODIMENTS

Figure 1:
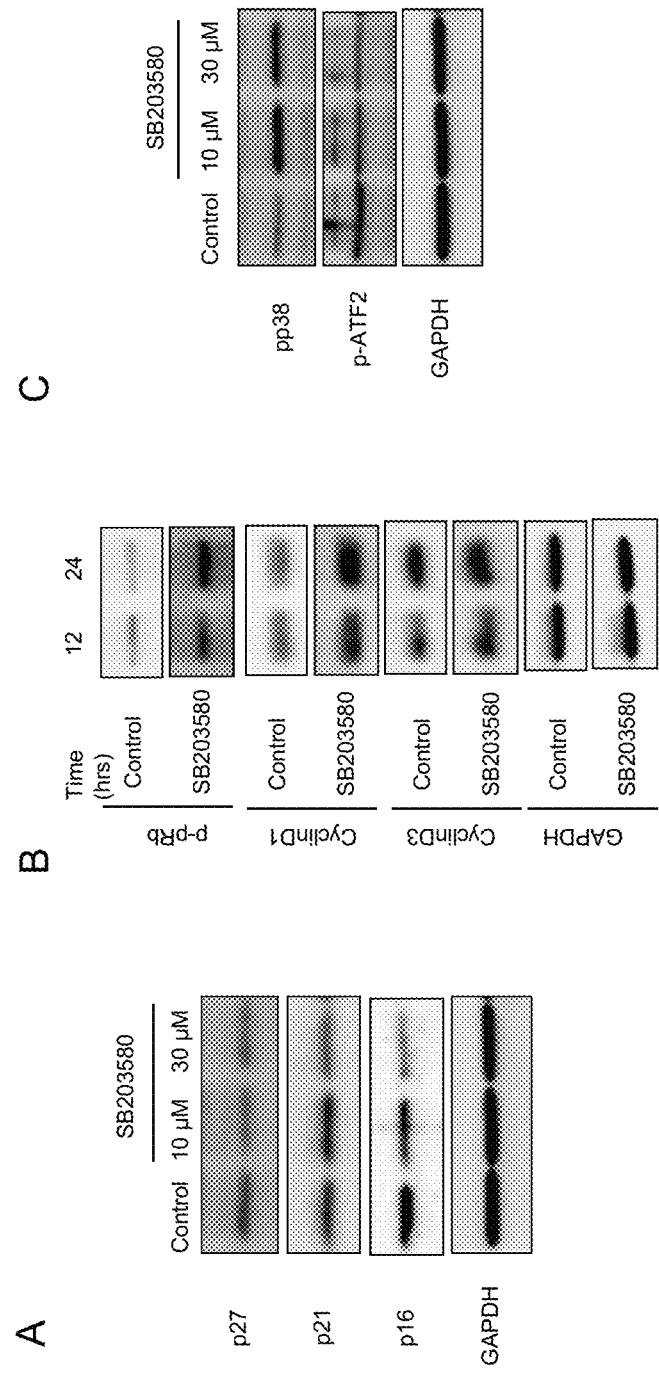
FIG. 1 shows that a p38 MAP kinase signal inhibition suppresses a cyclin-dependent kinase inhibiting factor to transition a cell cycle of corneal endothelial cells. Corneal endothelial cells cultured from corneas for research, which were imported from the Seattle Eye Bank, were cultured for use in the following study. A p38 MAP kinase inhibitor SB203580 was added to a cell culture medium to study the expression of cyclin-dependent kinase inhibiting factors p27, p21, and p16 after 20 days by Western blotting. Each of p27, p21, and p16 was suppressed by the addition of SB203580 (A: p27, p21, p16, and GAPDH are shown in order from the top. The left lane shows the controls, the middle shows 10 μM of SB203580, and the right lane shows 30 μM of SB203580). It is reported that p27, p21, and p16 are cyclin-dependent kinase inhibiting factors negatively regulating corneal endothelial cell proliferation. Further, when expression of cyclins D1 and D3 and phosphorylation of Rb proteins as a molecule associated with transition of cell cycle to the G1/S phase were studied by Western blotting, expression of such molecules was promoted after 12 hours and 24 hours by the addition of SB203580 (B; two rows each of, from the top, phosphorylated Rb protein, cyclin D1, cyclin D3 and GAPDH are shown. In each of the two rows, the top side shows a control and the bottom side shows stimulation by SD203580 (10 μM). The left lane shows 12 hours and the right lane shows 24 hours). Further, it was confirmed that phosphorylation of ATF2, which is a downstream molecule of a p38 MAP kinase signal, was suppressed by SB203580 by Western blotting as of 20 days after the stimulation. (C; phosphorylated p38, phosphorylated ATF2, and GAPDH are shown from the top. The left lane shows the controls, the middle shows 10 μM of SB203580, and the right lane shows 30 μM of SB203580). The above results demonstrate that cycline-dependent kinase inhibiting factors are suppressed and the cell cycle of corneal endothelial cells is transitioned by inhibiting p38 MAP kinase signals. Further, it is known that expression of p27, p21, and p16 is promoted by senescence. However, it was demonstrated that the expression is suppressed by SB203580 to suppress cellular senescence.

The present invention is described hereinafter. Throughout the entire specification, a singular expression should be understood as encompassing the concept thereof in the plural form unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art pertaining to the present invention. In case of a contradiction, the present specification (including the definitions) takes precedence.

Definitions

As used herein, "cell mitogen factor (mitogen) activated protein (MAP) kinase" is a mitogen activated protein (MAP) phosphorylating enzyme, which is a part of the serine/threonine kinase family. MAP kinases are from the serine/threonine protein kinase group, which are activated in response to various extracellular stimulations and mediate signaling from a cell surface to a nucleus. MAP kinases also are called extracellular signal-regulated protein kinases or ERK and are terminal enzymes in a 3 kinase cascade. In a related context, repeat of a 3 kinase cascade for a divided signaling pathway leads to the concept of a MAP kinase pathway as a modular multifunctional signaling element sequentially acting in one pathway, which is characterized in that each enzyme is phosphorylated whereby the next member in the sequence is activated. In this manner, a standard MAP kinase module consists of three protein kinases. That is, a certain MAP kinase kinase (or MEKK) activates a certain MAP kinase kinase (or MEK), which activates a certain MAPK/ERK enzyme in order. Each of MAPK/ERK, JNK (c-jun amino terminal protein kinase (or SAPK)) and p38 cascades consist of three enzyme modules including MEKK, MEK and ERK, or a MAP kinase superfamily member. When various extracellular signals bind with their respectively cell surface receptor, an initial event is triggered, and then the signal is transmitted inside the cells, where an appropriate cascade is activated.

A MAP kinase is a mitogen activated protein kinase (or ERK) super family having a TXY consensus sequence in a catalytic core. ERK1/2, p38HOG, and JNK/SAPK are related in parallel pathways, but are separate terminal enzymes.

Sebolt-Leopold et al., Nat. Med., 5(7): 810-6 (July, 1999) describes an in vitro cascade assay system for identifying a small molecule inhibitor of a MAP kinase (MAPK) pathway. Glutathione-S-transferase (GST)-MEK1 and GST-MAPK fusion proteins prepared from microbial cells were used in this assay system for sequential phosphorylation of MEK1 into MAPK or MBP (myelin basic protein). PD184352 [2-(2-chloro-4-iodine-phenylamino)-N-cyclopropyl-methoxy-3,4-difluoro-benzamide] that directly inhibits MEK1 has also been discovered.

As used herein, a "p38 MAP kinase inhibitor (also referred to as "p38 MAPK inhibitor")" refers to any agent that inhibits signaling of a MAP kinase associated with p38. Thus, a p38 MAP kinase inhibitor relates to a compound that targets and decreases or inhibits a p38 MAP kinase, which is a MAP kinase family member. It is preferable that a p38 MAP kinase inhibitor is water-soluble. This is because, if the p38 MAP kinase inhibitor is not water soluble, it may be necessarily to use an inhibitor that is less likely to be compatible to the body as a solvent. Whether a p38 MAP kinase inhibitor is water soluble can be classified based on the definition of solubility in the pharmacopoeia. That is, the amount of solvent required to dissolve 1 g or 1 mL of solute is defined as extremely readily dissolvable: less than 1 mL; readily dissolvable: 1 mL or greater and less than 10 mL; somewhat readily dissolvable: 10 mL or greater and less than 30 mL; somewhat difficult to dissolve: 30 mL or greater and less than 100 mL; difficult to dissolve: 100 mL or greater and less than 1000 mL; very difficult to dissolve: 1000 mL or greater and less than 10000 mL; and hardly dissolvable: 10000 mL or greater. Solubility is similarly assessed herein. For water solubility, it is understood that a substance with any solubility can be used as long as an effective amount thereof can be dissolved when water is used as a solvent. For instance, 4-(4-fluorophenyl)-2-(4-methylsulfinylphenyl)-5-(4-pyridyl)-1H-imidazole (SB-203580) is considered soluble into methanol, but difficult to dissolve in water, while a hydrochloride of 4-(4-fluorophenyl)-2-(4-methylsulfinylphenyl)-5-(4-pyridyl)-1H-imidazole (SB-203580) is considered soluble into water and is classified as water-soluble.

P38 is a mammalian MAP kinase super family member, which is activated by stress, ultraviolet ray and inflammatory cytokine. P38 has a TGY consensus sequence in a catalytic core.

Abnormally regulated kinases have been gradually recognized as the main pathological cause of many diseases, especially proliferative and inflammatory disorders. One of the carcinogenic genes first identified in a cancer region was for epithelial growth factor receptor kinases (EGFR). Excessive expression thereof is associated with lung, breast, brain, prostate, GI and ovarian cancer. For example, structural activation of a MAP kinase is associated with primary tumor from numerous cancer cell lineages (pancreas, large intestine, lung, ovary, and kidney) and various human organs (kidney, large intestine, and lung) (Hoshino et al., Oncogene, 18(3): 813-22 (January 1999)). Furthermore, p38 MAP kinases regulate the production of two cytokines associated with onset and progression of inflammation, TNFα and IL-1.

Besides VX-745 (Vertex Pharmaceuticals Inc.), p38 MAP kinase inhibitors that can be used in the present invention are not particularly limited, as long as it is a compound having p38 MAP kinase inhibiting activity, including the compounds described in patent documents such as Japanese Laid-Open Publication No. 2002-97189, Japanese National Phase PCT Laid-open Publication No. 2000-503304, Japanese National Phase PCT Laid-open Publication No. 2001-522357, Japanese National Phase PCT Laid-open Publication No. 2003-535023, Japanese National Phase PCT Laid-open Publication No. 2001-506266, Japanese National Phase PCT Laid-open Publication No. 9-508123, International Publication No. WO 01/56553, International Publication No. WO 93/14081, International Publication No. WO 01/35959, International Publication No. WO 03/68229, International Publication No. WO 03/85859, Japanese National Phase PCT Laid-open Publication No. 2002-534468, Japanese National Phase PCT Laid-open Publication No. 2001-526222, Japanese National Phase PCT Laid-open Publication No. 2001-526223, U.S. Pat. No. 6,344,476, International Publication No. WO 03/99811, International Publication No. WO 03/99796, Japanese National Phase PCT Laid-open Publication No. 2004-506042, International Publication No. WO 04/60286, Japanese National Phase PCT Laid-open Publication No. 2002-363179, Japanese National Phase PCT Laid-open Publication No. 2004-107358, U.S. Pat. Nos. 5,670,527, 6,096,753, International Publication No. WO 01/42189 and International Publication No. WO 00/31063, preferably 4-(4-fluorophenyl)-2-(4-hydroxyphenyl)-5-(4-pyridyl)-1H-imidazole (SB-202190), trans-4-[4-(4-fluorophenyl)-5-(2-methoxy-4-pyrimidinyl)-1H-imidazole-1-yl]cyclohexanol (SB-239063), 4-(4-fluorophenyl)-2-(4-methylsulfinylphenyl)-5-(4-pyridyl)-1H-imidazole (SB-203580), 4-(4-fluorophenyl)-5-(2-methoxypyrimidine-4-yl)-1-(piperidine-4-yl)imidazole (SB-242235), 4-(4-fluorophenyl)-2-(4-hydroxy-1-butynyl)-1-(3-phenylpropyl)-5-(4-pyridyl)imidazole (RWJ-67657), 4-(4-fluorophenyl)-1-(piperidine-4-yl)-5-(4-pyridyl)imidazole (HEP-689), (S)-2-(2-amino-3-phenylpropylamino)-1-methyl-5-(2-naphthyl)-4-(4-pyridyl)pyrimidine-6-one (AMG-548), 2-chloro-4-(4-fluoro-2-methylanilino)-2'-methylbenzophenone (EO-1606), 3-(4-chlorophenyl)-5-(1-hydroxyacetylpiperidine-4-yl)-4-(pyrimidine-4-yl)pyrazole (SD-06), 5-(2,6-dichlorophenyl)-2-(2,4-difluorophenylthio)pyrimido[3,4-b]pyridazine-6-one (VX-745), 4-acetylamino-N-tert-butylbenzamide (CPI-1189), N-[3-tert-butyl-1-(4-methylphenyl)pyrazole-5-yl)-N'-[4-(2-morpholinoethoxy)-1-naphthyl]urea (Doramapimod), 2-benzamide-4-[2-ethyl-4-(3-methylphenyl)thiazole-5-yl]pyridine (TAK-715), SCIO-469, 1-(carbamoyl-6-(2,4-difluorophenyl)pyridine-2-yl)-1-(2,6-difluorophenyl)urea (VX-702; 2-(2,4-difluorophenyl)-6-(1-(2,6-difluorophenyl) ureido)nicotinamide), GSK-681323, PS-540446, SC-80036, AVE-9940, RO-320-1195, 1-(1,3-dihydroxyprop-2-yl)-4-(4-fluorophenyl)-5-[2-phenoxypyrimidine-4-yl]imidazole (SB-281832), 2-[5-({4-[(4-fluorophenyl)methyl]piperidine-1-yl}carbonyl)-6-methoxy-1-methyl-1H-indole-3-yl]-N,N'-dimethyl-2-oxoacetamide (SCIO-323), 2-(5-tert-butyl-2-m-tolyl-2H-pyrazole-3-yl)-2-hydroxyimide-N-[4-(2-morpholine-4-yl-ethoxy)-naphthalene-1-yl]-acetamide (KC-706), N,N'-bis[3,5-bis[1-(2-amidinohydrazono)ethyl]phenyl]decandiamide, N,N'-bis[3,5-bis[1-[2-(aminoiminomethyl)hydrazono]ethyl]phenyl]decandiamide (Semapimod), 3-(3-bromo-4-((2,4-difluorobenzyl)oxy)-6-methyl-2-oxopyridine-1(2H)-yl)-N,4-dimethylbenzamide (PH-797804), and 5-(2-(tert-butyl)-5-(4-fluorophenyl)-1H-imidazole-4-yl)-3-neopentyl-3H-imidazo[4,5-b]pyridine-2-amine (LY2228820).

Furthermore, Tocris Cookson (St Louis, USA) provides various MAP kinase inhibitors exemplified at http://www-.tocris.com/. For instance, SB202190 (4-[4-(4-fluorophenyl)-5-(4-pyridinyl)-1H-imidazole-2-yl]phenol) is a highly selective, potent and cell permeable p38 MAP kinase inhibitor (SmithKline Beecham, plc) (Jiang et al., J. Biol. Chem, 271: 17920 (1996); Frantz et al., Biochemistry, 37: 138-46 (1998); Nemoto et al., J. Biol. Chem., 273: 16415 (1998); and Davies et al., Biochem. J., 351:95 (2000)). Further, anisomycin ((2R,3R,4S)-2-[(4-methoxyphenyl)methyl]-3,4-pyrrolidinediol-3-acetate) is a protein synthesis inhibitor (blocks translation). This is a potent activator of stress activated protein kinases (JNK/SAPK) and p38 MAP kinases, acting as a potent signaling agonist that selectively induces homologous desensitization induced by an immediate early gene (c-fos, fosB, c-jun, junB, and junD). PD98059 (2-(2-amino-3-methoxyphenyl)-4H-1-benzopyran-4-one) is a specific inhibitor of a mitogen activated protein kinase kinase (MAPKK) (Pfizer=Warner-Lambert Company). SB203580 4-(4-fluorophenyl)-2-(4-methylsulfinylphenyl)-5-(4-pyridyl)-1H-imidazole) is a highly selective inhibitor of p38 mitogen activated protein kinases (SmithKline Beecham, plc). It is shown that interleukin-2-derived T cell proliferation, cyclooxygenase-1 and -2 and thromboxane synthase are inhibited. SB203580 hydrochloride 4-(4-fluorophenyl)-2-(4-methylsulfinylphenyl)-5-(4-pyridyl)-1H-imidazole) compound is a water-soluble salt of a highly selective p38 mitogen activated protein kinase inhibitor. It is shown that interleukin-2-derived T cell proliferation, cyclooxygenase-1 and -2 and thromboxane synthase are inhibited. U0126 (1,4-diamino-2,3-dicyano-1,4-bis[2-aminophenylthio]butadiene) is a potent and selective non-competitive inhibitor of MAP kinase kinase.

An example of a preferred p38 MAP kinase inhibitor includes SB203580 4-(4-fluorophenyl)-2-(4-methylsulfinylphenyl)-5-(4-pyridyl)-1H-imidazole, but is not limited thereto.

Other examples of p38 MAP kinase inhibitors that can be used in the present invention include neutralizing antibodies against p38 MAP kinases, compounds inhibiting the activity of p38 MAP kinases, compounds inhibiting transcription of a gene encoding a p38 MAP kinase (e.g., antisense nucleic acids, RNAi, ribozymes), peptides, and compounds of a plant component or the like (e.g., polyphenol, flavonoid, glycoside). A concentration used is for example about 50 µmol/l-100 µmol/l, and is generally about 0.001-100 µmol/l, preferably about 0.01-75 µmol/l, about 0.05-50 µmol/l, about 1-10 µmol/l, about 0.01-10 µmol/l, about 0.05-10 µmol/l, about 0.075-10 µmol/l, about 0.1-10 µmol/l, about 0.5-10 µmol/l, about 0.75-10 µmol/l, about 1.0-10 µmol/l, about 1.25-10 µmol/l, about 1.5-10 µmol/l, about 1.75-10 µmol/l, about 2.0-10 µmol/l, about 2.5-10 µmol/l, about 3.0-10 µmol/l, about 4.0-10 µmol/l, about 5.0-10 µmol/l, about 6.0-10 µmol/l, about 7.0-10 µmol/l, about 8.0-10 µmol/l, about 9.0-10 µmol/l, about 0.01-50 µmol/l, about 0.05-5.0 µmol/l, about 0.075-5.0 µmol/l, about 0.1-5.0 µmol/l, about 0.5-5.0 µmol/l, about 0.75-5.0 µmol/l, about 1.0-5.0 µmol/l, about 1.25-5.0 µmol/l, about 1.5-5.0 µmol/l, about 1.75-5.0 µmol/l, about 2.0-5.0 µmol/l, about 2.5-5.0 µmol/l, about 3.0-5.0 µmol/l, about 4.0-5.0 µmol/l, about 0.01-3.0

µmol/l, about 0.05-3.0 µmol/l, about 0.075-3.0 µmol/l, about 0.1-3.0 µmol/l, about 0.5-3.0 µmol/l, about 0.75-3.0 µmol/l, about 1.0-3.0 µmol/l, about 1.25-3.0 µmol/l, about 1.5-3.0 µmol/l, about 1.75-3.0 µmol/l, about 2.0-3.0 µmol/l, about 0.01-1.0 µmol/l, about 0.05-1.0 µmol/l, about 0.075-1.0 µmol/l, about 0.1-1.0 µmol/l, about 0.5-1.0 µmol/l, about 0.75-1.0 µmol/l, about 0.09-35 µmol/l, about 0.09-3.2 µmol/l, and more preferably about 0.05-1.0 µmol/l, about 0.075-1.0 µmol/l, about 0.1-1.0 µmol/l, about 0.5-1.0 µmol/l, and about 0.75-1.0 µmol/l, but is not limited thereto.

Antisense nucleic acids used in the present invention may inhibit the expression and/or function of a gene (nucleic acid) encoding a member of a signaling pathway of the p38 MAP kinase discussed above or the like by any of the above-described action. As one embodiment, translation of a gene would be considered effectively inhibited by designing an antisense sequence complementary to an untranslated region near the 5' end of mRNA of a gene encoding the aforementioned p38 MAP kinase or the like. Further, a sequence that is complementary to an untranslated region of 3' or a coding region can also be used. In this manner, antisense nucleic acids utilized in the present invention include not only a translation region of a gene encoding the aforementioned p38 MAP or the like, but also nucleic acids comprising an antisense sequence of a sequence of an untranslated region. An antisense nucleic acid to be used is linked downstream of a suitable promoter, and preferably a sequence comprising a transcription termination signal is linked to the 3' side. A nucleic acid prepared in this manner can be transformed into a desired animal (cell) by using a known method. A sequence of an antisense nucleic acid is preferably a sequence that is complementary to a gene encoding a p38 MAP kinase or the like of the animal (cell) to be transformed or a portion thereof. However, such a sequence does not need to be fully complementary, as long as gene expression can be effectively suppressed. A transcribed RNA preferably has complementarity that is 90% or greater, and most preferably 95% or greater, with respect to a transcript of a target gene. In order to effectively inhibit the expression of a target gene using an antisense nucleic acid, it is preferable than the length of the antisense nucleic acid is at least 12 bases and less than 25 bases. However, the antisense nucleic acid of the present invention is not necessarily limited to this length. For example, the length may be 11 bases or less, 100 bases or more, or 500 bases or more. An antisense nucleic acid may be composed of only DNA, but may comprise a nucleic acid other than DNAs, e.g., locked nucleic acid (LNA). As one embodiment, an antisense nucleic acid used in the present invention may be an LNA containing antisense nucleic acid comprising LNA at the 5' terminal or LNA at the 3' terminal. In an embodiment using an antisense nucleic acid in the present invention, the antisense sequence can be designed based on a nucleic acid sequence of a p38 MAP kinase or the like by using the method described in, for example, Hirashima and Inoue, Shin-seikagaku Jikkenn Kouza [*New Biochemical Experiment Course*] 2 Kakusan [*Nucleic Acid*] IV Idenshi no Fukusei to Hatsugen [*Duplication and Expression of Gene*], Ed. by the Japanese Biochemical Society, Tokyo Kagaku Dojin, 1993, 319-347.

Expression of p38 MAP kinases or the like can also be inhibited by utilizing a ribozyme or DNA encoding a ribozyme. A ribozyme refers to an RNA molecule having catalytic activity. There are ribozymes with various activities. A study especially focusing on ribozymes as an enzyme for cleaving an RNA made it possible to design a ribozyme that site-specifically cleaves an RNA. There are ribozymes with a size of 400 nucleotides or more as in group I intron ribozymes and Ml RNA contained in RNase P, but there are also those with an active domain of about 40 nucleotides called hammerhead and hair-pin ribozymes (Makoto Koizumi and Eiko Otsuka, Protein, Nucleic Acid and Enzyme, 1990, 35, 2191).

For example, a self-cleaving domain of a hammerhead ribozyme cleaves the 3' side of C15 of a sequence called G13U14C15. Base pair formation of U14 and A9 is considered important for the activity thereof. It is shown that cleavage can also be made at A15 or U15 instead of C15 (Koizumi, M. et al., FEBS Lett, 1988, 228, 228.) Restriction enzyme-like RNA-cleaving ribozymes that recognize the sequence UC, UU, or UA in the target RNAs can be created by designing their substrate-binding sites to be complementary to an RNA sequence near the target site (Koizumi, M. et al., FEBS Lett, 1988, 239, 285., Makoto Koizumi and Eiko Otsuka, Protein, Nucleic Acid and Enzyme, 1990, 35, 2191., Koizumi, M. et al., Nucl. Acids Res., 1989, 17, 7059.)

Further, hairpin ribozymes are also useful for the objective of the present invention. Such a ribozyme is found, for example, in the minus strand of a tobacco ringspot virus satellite RNA (Buzayan J M, Nature, 1986, 323; 349). It is shown that a target specific RNA-cleaving ribozymes can also be created from hairpin ribozymes (Kikuchi, Y. & Sasaki, N., Nucl. Acids Res, 1991, 19, 6751., Yo Kikuchi, Kagaku to Seibutsu [*Chemistry and Biology*], 1992, 30: 112). In this manner, expression of a gene encoding a p38 MAP kinase or the like can be inhibited by specifically cleaving a transcript of the gene by using a ribozyme.

Expression of an endogenous gene such as a p38 MAP kinase can also be suppressed by RNA interference (hereinafter abbreviated as "RNAi") using a double-stranded RNA having a sequence that is identical or similar to a target gene sequence. RNAi is a methodology current drawing attention, which can suppress the expression of a gene having a sequence that is homologous to a double strand RNA (dsRNA) when the dsRNA is uptaken directly into a cell. In mammalian cells, short stranded dsRNA (siRNA) can be used to induce RNAi. RNAi has many advantages relative to knockout mice, such as a stable effect, facilitated experiment, and low cost. SiRNA is discussed in detail in other parts of the specification.

As used herein "siRNA" is an RNA molecule having a double-stranded RNA portion consisting of 15-40 bases, where siRNA has a function of cleaving mRNA of a target gene with a sequence complementary to an antisense strand of the siRNA to suppress expression of the target gene. Specifically, the siRNA in the present invention is an RNA comprising a double-stranded RNA portion consisting of a sense RNA strand consisting of a sequence homologous to consecutive RNA sequences in mRNA of p38 MAP kinases or the like and an antisense RNA strand consisting of a sequence complementary to the sense RNA sequence. Design and manufacture of such siRNA and mutant siRNA discussed below are within the competence of those skilled in the art. Any consecutive RNA regions of mRNA which is a transcript of a sequence of p38 MAP kinase or the like can be appropriately selected to make double-stranded RNA corresponding to this region, which is within the ordinary procedure performed by those skilled in the art. Further, those skilled in the art can appropriately select siRNA having a stronger RNAi effect from mRNA sequences, which are transcripts of the sequence, by a known method. Further, if one of the strands is revealed, those skilled in the art can readily find the base sequence of the other stand (complementary strand). SiRNA can be appropriately made by using a commercially available nucleic acid synthesizer. Further, a common synthesis services can be utilized for desired RNA synthesis.

In terms of bases, the length of a double-stranded RNA portion is 15-40 bases, preferably 15-30 bases, more preferably 15-25 bases, still more preferably 18-23 bases, and most preferably 19-21 bases. It is understood that the upper limits and the lower limits are not limited to such specific limits, and may be of any combination of the mentioned limits. The terminal structure of a sense strand or antisense strand of siRNA is not particularly limited, and can be appropriately selected in accordance with the objective. For example, such a terminal structure may have a blunt end or a sticky end (overhang). A type where the 3' end protrudes out is preferred. SiRNA having an overhang consisting of several bases, preferably 1-3 bases, and more preferably 2 bases at the 3' terminal of a sense RNA strand and antisense RNA strand is preferable for having a large effect of suppressing expression of a target gene in many cases. The type of bases of an overhang is not particularly limited, which may be either a base constituting an RNA or a base constituting a DNA. An example of a preferred overhang sequence includes dTdT at the 3' terminal (2 by of deoxy T) and the like. Examples of preferable siRNA include, but are not limited to, all siRNA with dTdT (2 by of deoxy T) at the 3' terminal of the sense or antisense strands.

Furthermore, it is also possible to use siRNA in which one to several nucleotides are deleted, substituted, inserted and/or added at one or both of the sense strand and antisense strand of the siRNA described above. One to several bases as used herein is not particularly limited, but preferably refers to 1 to 4 bases, still more preferably 1 to 3 bases, and most preferably 1 to 2 bases. Specific examples of such mutations include, but are not limited to, mutations with 0 to 3 bases at the overhand portion, mutations in which the base sequence of the 3'-overhang portion is changed to another base sequence, mutations in which the length of the above-described sense RNA strand and antisense RNA strand is different by 1 to 3 bases due to insertion, addition or deletion of bases, mutations substituting the base in the sense strand and/or antisense with another base, and the like. However, it is necessary that the sense strand and antisense strand can hybridize in such mutant siRNAs, and these mutant siRNAs to have the ability to suppress gene expression that is equivalent to that of siRNAs without any mutations.

Furthermore, siRNA may also have a molecule with a structure in which one end is closed, such as a hairpin structure (Short Hairpin RNA; shRNA). A shRNA is an RNA comprising a sense strand RNA of a specific sequence of a target gene, an antisense strand RNA consisting of a sequence complementary to the sense strand sequence, and a linker sequence for connecting the two strands, wherein the sense strand portion hybridizes with the antisense strand portion to form a double-stranded RNA portion.

It is desirable for siRNA not to exhibit the so-called off-target effect in clinical use. An off-target effect refers to an action for suppressing the expression of another gene, besides the target gene, which is partially homologous to the siRNA used. In order to avoid an off-target effect, it is possible to confirm that a candidate siRNA does not have cross reactivity by using a DNA microarray in advance. Further, it is possible to avoid an off-target effect by confirming whether there is a gene comprising a moiety that is highly homologous to a sequence of a candidate siRNA, other than a target gene, using a known database provided by the NCBI (National Center for Biotechnology Information) or the like.

In order to make the siRNA according to the present invention, a known method, such as a method using chemical synthesis or a method using a gene recombination technique, can be appropriately used. With a method using synthesis, a double-stranded RNA can be synthesized based on sequence information by using a common method. With method using a gene recombination technique, a siRNA can be made by constructing an expression vector encoding a sense strand sequence or an antisense strand sequence and introducing the vector into a host cell, and then obtaining each of sense strand RNA and antisense strand RNA produced by transcription. Further, it is possible to make a desired double-stranded RNA by expressing a shRNA forming a hairpin structure, which comprises a sense strand of a specific sequence of a target gene, an antisense strand consisting of a sequence complementary to the sense strand sequence, and a linker sequence for linking the two strands.

For a siRNA, all or part of the nucleic acid constituting the siRNA may be a natural or a modified nucleic acid, as long as such a nucleic acid has an activity to suppress the expression of a target gene.

The siRNA according to the present invention does not necessarily have to be a pair of double-stranded RNAs to a target sequence. It may be a mixture of a plurality of pairs (the "plurality" is not particularly limited, but preferably refers to a small number of about 2 to 5) of double-stranded RNAs to a region comprising a target sequence. In this regard, those skilled in the art can appropriately make a siRNA as a nucleic acid mixture corresponding to a target sequence by using a commercially available nucleic acid synthesizer and a DICER enzyme. Further, a common synthesis service can be utilized for desired RNA synthesis. It should be noted that the siRNA according to the present invention encompasses the so-called "cocktail siRNA". For the siRNA according to the present invention, not all the nucleotides have to be a ribonucleotide (RNA). Specifically, in the present invention, one or plurality of ribonucleotides constituting a siRNA may be a corresponding deoxyribonucleotide. The term "corresponding" refers to having the same base type (adenine, guanine, cytosine, thymine (uracil)) but a different sugar moiety structure. For example, a deoxyribonucleotide corresponding to a ribonucleotide having adenine refers to a deoxyribonucleotide having adenine.

Furthermore, a DNA (vector) which can express the above-described RNA according to the present invention is also encompassed as a preferred embodiment of a nucleic acid which can suppress expression of p38 MAP kinase or the like. For example, the DNA (vector) which can express the above-described double-stranded RNA according to the present invention is a DNA having a structure in which a DNA encoding one of the strands of the double-stranded RNA and a DNA encoding the other strand of the double-stranded RNA are linked with a promoter so that each of the DNAs can be expressed. The above-described DNA according to the present invention can be appropriately made by those skilled in the art by using a common genetic engineering technique. More specifically, the expression vector according to the present invention can be made by appropriately inserting a DNA encoding the RNA of interest into various known expression vectors.

In the present invention, a modified nucleic acid may be used as a nucleic acid for suppressing the expression of a target gene. A modified nucleic acid refers to a nucleic acid, which has a modification at a nucleoside (base moiety, sugar moiety) and/or an inter-nucleoside binding site and has a structure different from that of a natural nucleic acid. Examples of "modified nucleoside" constituting a modified nucleic acid include: abasic nucleosides; arabinonucleoside, 2'-deoxyuridine, α-deoxyribonucleoside, β-L-deoxyribonucleoside, and nucleosides having other sugar modifications; peptide nucleic acid (PNA), phosphate group-binding peptide nucleic acid (PHONA), locked nucleic acid (LNA), morpholino nucleic acid and the like. The above-described nucleosides having a sugar modification include 2'-O-methylribose, 2'-deoxy-2'-fluororibose, 3'-O-methylribose and other substituted pentose; 1',2'-deoxyribose; arabinose; substituted arabinose sugar; and nucleoside having a sugar modification of alpha-anomer and hexose. These nucleosides may be a modified base in which the base moiety is modified. Examples of such modified bases include pyrimidine such as 5-hydroxycytosine, 5-fluorouracil, and 4-thiouracil; purine such as 6-methyladenine and 6-thioguanosine; other heterocyclic bases and the like.

Examples of a "modified inter-nucleoside bond" which constitutes a modified nucleic acid include alkyl linker, glyceryl linker, amino linker, poly(ethylene glycol) bond, inter-methyl phosphonate nucleoside bond; methylphosphonothioate, phosphotriester, phosphothiotriester, phosphorothioate, phosphorodithioate, triester prodrug, sulfone, sulfonamide, sulfamate, formacetal, N-methylhydroxylamine, carbonate, carbamate, morpholino, boranophosphonate, phosphoramidate and other bonds between non-natural nucleosides.

The nucleic acid sequence comprised in the double-stranded siRNA according to the present invention includes a siRNA for a p38 MAP kinase, other p38 MAP kinase signal members and the like.

It is also possible to introduce the nucleic acid or agent according to the present invention into a phospholipid endoplasmic reticulum such as a liposome to administer the endoplasmic reticulum. An endoplasmic reticulum in which a siRNA or shRNA is retained can be introduced into a predetermined cell using lipofection. The resulting cell is then systemically-administered, for example intravenously, intra-arterially or the like. The endoplasmic reticulum can also be locally administered to a required site in an eye or the like. While a siRNA exhibits a very good specific, post-transcription suppressing effect in vitro, the siRNA is quickly degraded in vivo due to nuclease activity in the serum. Since the duration thereof is limited, there has been a need for development of a better and more effective delivery system. As an example, Ochiya, T et al., Nature Med., 5: 707-710, 1999, Curr. Gene Ther., 1: 31-52, 2001 reports that a biocompatible material atelocollagen, when mixed with a nucleic acid to form a complex, is a carrier having an action of protecting a nucleic acid from a degrading enzyme in a living organism and is extremely suitable as a carrier of a siRNA. While such a form can be used, the method for introducing a nucleic acid, therapeutic or prophylactic drug according to the present invention is not limited thereto. In this manner, due to fast degradation by the action of a nucleic acid degrading enzyme in serum in a living organism, it becomes possible to achieve continuation of the effect for an extended period of time. For example, Takeshita F. PNAS, (2003) 102 (34) 12177-82, Minakuchi Y Nucleic Acids Research (2004) 32 (13) e109 report that atelocollagen derived from bovine skin forms a complex with a nucleic acid, which has action of protecting a nucleic acid from a degrading enzyme in a living organism and is extremely suitable as a carrier of a siRNA. Such a technique can be used.

As used herein, "corneal endothelial disease, disorder or condition requiring cell proliferation, suppression of cellular disorder, or suppression of cellular senescence" refers to any corneal endothelial disease, disorder or condition associated with at least one of corneal endothelial disorder, cellular disorder, and cellular senescence requiring cell proliferation for which cell proliferation, suppression of cellular disorder, or suppression of cellular senescence can achieve improvement or healing. Examples of corneal endothelial disease, disorder or condition requiring cell proliferation, suppression of cellular disorder, or suppression of cellular senescence include, but are not limited to, disorders associated with corneal endotheliitis, senescence, ocular surgery, trauma, sustained decrease in corneal endothelial density post-corneal transplantation, Fuchs' corneal endothelial dystrophy, and the like. As used herein, "corneal endothelial disorder requiring cell proliferation" refers to a condition where there is a loss of corneal endothelium due to trauma, surgery or the like, and "cellular disorder" refers to a condition where apoptosis, cell death or the like has occurred due to Fuchs' corneal endothelial dystrophy, corneal endotheliitis or the like. In addition, "cellular senescence" refers to a condition where expansion of cytoplasm, decrease in cell density, increase in size mismatch in cells, decrease in the ratio of hexagonal cells, decrease in cell proliferation capability or the like has occurred.

(General Techniques)

Molecular biological methodology, biochemical methodology, microbiological methodology used herein are well known and conventionally used in the art, which are described for example in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [*Experimental Medicine, Supplemental Volume*], Idenshi Donyu Oyobi Hatsugen Kaiseki Jikken Ho [*Experimental Methods for Transgenesis & Expression Analysis*], Yodosha, 1997, or the like. The reports by Nancy Joyce et al {Joyce, 2004 #161} and {Joyce, 2003 #7} are well known for corneal endothelial cells. However, as discussed above, long-term culture or subculture results in fibroblast-like transformation, and research for an effective culturing method is currently ongoing. Relevant portions (which may be all) thereof are incorporated herein by reference.

DESCRIPTION OF PREFERRED EMBODIMENTS

Preferred embodiments of the present invention are described below. The embodiments are provided for better understanding of the present invention. It is understood that the scope of the present invention is not limited to such preferred embodiments. Further, it should be understood that those skilled in the art can readily make modifications or changes within the scope of the present invention while referring to the following preferred examples. For such embodiments, those skilled in the art can appropriately combine any embodiments.

In one aspect, the present invention provides a therapeutic or prophylactic drug for a corneal endothelial disorder requiring cell proliferation, comprising a p38 MAP kinase inhibitor. A p38 MAP kinase is considered to be involved in various signaling. A p38 MAP kinase is also considered to be involved in inflammations. However, not the entire mechanism thereof is elucidated in corneal endothelia. In particular, it was unexpected that, for example, inhibition of corneal endothelial disorder requiring cell proliferation is effective in healing or prevention of a wound. Thus, application of a p38 MAP kinase inhibitor to treat or prevent a corneal endothelial disorder requiring cell proliferation is recognized as an unexpected discovery found by the inventors. In particular, a p38 MAP kinase inhibitor in an embodiment available as eye drops had not been found. Thus, such an embodiment should be considered highly valued in actual clinical settings.

In one embodiment, the p38 MAP kinase inhibitor is water soluble. This is because, if the p38 MAP kinase inhibitor is water soluble, water which has no issues in terms of biocompatibility can be utilized as a solvent. A p38 MAP kinase inhibitor that is not water-soluble can be utilized as along as it dissolves into a pharmaceutically acceptable solvent (e.g., ethanol or the like). Solubility can be classified based on the definition of solubility in the pharmacopoeia. That is, the amount of solvent required to dissolve 1 g or 1 mL of solute is defined as extremely readily dissolvable: less than 1 mL; readily dissolvable: 1 mL or greater and less than 10 mL; somewhat readily dissolvable: 10 mL or greater and less than 30 mL; somewhat difficult to dissolve: 30 mL or greater and less than 100 mL; difficult to dissolve: 100 mL or greater and less than 1000 mL; very difficult to dissolve: 1000 mL or greater and less than 10000 mL; and hardly dissolvable: 10000 mL or greater. Components of the present invention are similarly assessed. For water solubility, it is understood that a substance with any solubility can be used as long as an effective amount thereof can be dissolved when water is used as a solvent. For the present invention, target solubility (water solubility for water) generally refers to solubility within the scope of "readily dissolvable" or greater. However, "somewhat readily dissolvable" substances can be used in some cases. In addition, substances classified as "somewhat difficult to dissolve" and "difficult to dissolve" can be also used if there is an effect at a low concentration. For example, 4-(4-fluorophenyl)-2-(4-methylsulfinylphenyl)-5-(4-pyridyl)-1H-imidazole (SB-203580) is considered soluble into methanol, but difficult to dissolve in water, while a hydrochloride of 4-(4-fluorophenyl)-2-(4-methylsulfinylphenyl)-5-(4-pyridyl)-1H-imidazole (SB-203580) is considered soluble into water and classified as water-soluble.

In one embodiment, methods of utilizing the present invention, besides as eye drops, include administration methods such as injection into the anterior chamber, impregnation into a sustained release agent, subconjunctival injection, systemic administration (oral administration, intravenous injection) and the like.

In one embodiment, the p38 MAP kinase inhibitor used in the present invention comprises at least one agent selected from the group consisting of 4-(4-fluorophenyl)-2-(4-hydroxyphenyl)-5-(4-pyridyl)-1H-imidazole (SB-202190), trans-4-[4-(4-fluorophenyl)-5-(2-methoxy-4-pyrimidinyl)-1H-imidazole-1-yl]cyclohexanol (SB-239063), 4-(4-fluorophenyl)-2-(4-methylsulfinylphenyl)-5-(4-pyridyl)-1H-imidazole (SB-203580), 4-(4-fluorophenyl)-5-(2-methoxypyrimidine-4-yl)-1-(piperidine-4-yl)imidazole (SB-242235), 4-(4-fluorophenyl)-2-(4-hydroxy-1-butynyl)-1-(3-phenylpropyl)-5-(4-pyridyl)imidazole (RWJ-67657), 4-(4-fluorophenyl)-1-(piperidine-4-yl)-5-(4-pyridyl)imidazole (HEP-689), (S)-2-(2-amino-3-phenylpropylamino)-1-methyl-5-(2-naphthyl)-4-(4-pyridyl)-pyrimidine-6-one (AMG-548), 2-chloro-4-(4-fluoro-2-methylanilino)-2'-methylbenzophenone (EO-1606), 3-(4-chlorophenyl)-5-(1-hydroxyacetylpiperidine-4-yl)-4-(pyrimidine-4-yl)-pyrazole (SD-06), 5-(2,6-dichlorophenyl)-2-(2,4-difluorophenylthio) pyrimido[3,4-b]pyridazine-6-one (VX-745), 4-acetylamino-N-tert-butylbenzamide (CPI-1189), N-[3-tert-butyl-1-(4-methylphenyl)pyrazole-5-yl]-N'44-(2-morpholinoethoxy)-1-naphthyl]urea (Doramapimod), 2-benzamide-4-[2-ethyl-4-(3-methylphenyl)thiazole-5-yl]pyridine (TAK-715), Talmapimod (SCIO-469), 1-(carbamoyl-6-(2,4-difluorophenyl)pyridine-2-yl)-1-(2,6-difluorophenyl) urea (VX-702; 2-(2,4-difluorophenyl)-6-(1-(2,6-difluorophenyl)ureido) nicotinamide), dilmapimod (GSK-681323), 4-(5-(cyclopropylcarbamoyl)-2-methylphenylamino)-5-methyl-N-propylpyrrolo-(1,2-f)(1,2,4)triazine-6-carboxamide (PS-540446), 4-[3-(4-chloro-phenyl)-5-(1-(2-hydroxy-1-oxoethyl)-pyperizine-4-yl)-pyrazo-4-yl]-pyrimidine (SC-80036), AVE-9940 (Sanofi-Aventis), [5-amino-1-(4-fluorophenyl)-1H-pyrazole-4-yl][3-(3-amino-2-hydroxypropoxy)phenyl]methanone (RO-320-1195), 1-(1,3-dihydroxyprop-2-yl)-4-(4-fluorophenyl)-5-[2-phenoxypyrimidine-4-yl]imidazole (SB-281832), 2-[5-({4-[(4-fluorophenyl)methyl]piperidine-1-yl}carbonyl)-6-methoxy-1-methyl-1H-indole-3-yl]-N,N'-dimethyl-2-oxoacetamide (SCIO-323), 2-(5-tert-butyl-2-m-tolyl-2H-pyrazole-3-yl)-2-hydroxyimide-N-[4-(2-morpholine-4-yl-ethoxy)-naphthalene-1-yl]-acetamide (KC-706), N,N'-bis[3,5-bis[1-(2-amidinohydrazono)ethyl] phenyl]decandiamide, N,N'-bis[3,5-bis[1-[2-(aminoiminomethyl)hydrazono]ethyl]phenyl]decandiamide (Semapimod), 3-(3-bromo-4-((2,4-difluorobenzyl)oxy)-6-methyl-2-oxopyridine-1(2H)-yl)-N-,4-dimethylbenzamide (PH-797804), and 5-(2-(tert-butyl)-5-(4-fluorophenyl)-1H-imidazole-4-yl)-3-neopentyl-3H-imidazo[4,5-b]pyridine-2-amine (LY2228820).

In a preferred embodiment, a p38 MAP kinase inhibitor is selected from the group consisting of 4-(4-fluorophenyl)-2-(4-methylsulfinylphenyl)-5-(4-pyridyl)-1H-imidazole (SB203580), N-[3-tert-butyl-1-(4-methylphenyl) pyrazole-5-yl]-N'44-(2-morpholinoethoxy)-1-naphthyl]urea (Doramapimod; BIRB796), 2-benzamide-4-[2-ethyl-4-(3-methylphenyl)thiazole-5-yl]pyridine (TAK-715), 1-(carbamoyl-6-(2,4-difluorophenyl)pyridine-2-yl)-1-(2,6-difluorophenyl) urea (VX-702; 2-(2,4-difluorophenyl)-6-(1-(2,6-difluorophenyl)ureido)nicotinamide), N,N'-bis[3,5-bis[1-[2-(aminoiminomethyl)hydrazono]ethyl]phenyl]decandiamide (Semapimod), 3-(3-bromo-4-((2,4-difluorobenzyl)oxy)-6-methyl-2-oxopyridine-1(2H)-yl)-N-,4-dimethylbenzamide (PH-797804), and 5-(2-(tert-butyl)-5-(4-fluorophenyl)-1H-imidazole-4-yl)-3-neopentyl-3H-imidazo[4,5-b]pyridine-2-amine (LY2228820) and salts thereof. More preferably, a p38 MAP kinase inhibitor comprises 4-(4-fluorophenyl)-2-(4-methylsulfinylphenyl)-5-(4-pyridyl)-1H-imidazole (SB203580) or a salt thereof. Preferably, a salt is a pharmaceutically acceptable salt.

In another embodiment, a p38 MAP kinase inhibitor comprises a hydrochloride of 4-(4-fluorophenyl)-2-(4-methylsulfinylphenyl)-5-(4-pyridyl)-1H-imidazole (SB203580). A hydrochloride of 4-(4-fluorophenyl)-2-(4-methylsulfinylphenyl)-5-(4-pyridyl)-1H-imidazole (SB203580) is preferable for healing a wound because it is water soluble, directly applicable as eye drops, and has little risk of side effects.

The concentration of a p38 MAP kinase agent used in the present invention is generally about 0.1-100 µmol/l, preferably about 0.1-30 µmol/l, and more preferably about 1 µmol/l. When several types of agents are used, the concentration can be appropriately changed. Examples of other concentration ranges include, but are not limited to, generally about 0.001-100 µmol/l, preferably about 0.01-75 µmol/l, about 0.05-50 µmol/l, about 1-10 µmol/l, about 0.01-10 µmol/l, about 0.05-10 µmol/l, about 0.075-10 µmol/l, about 0.1-10 µmol/l, about 0.5-10 µmol/l, about 0.75-10 µmol/l, about 1.0-10 µmol/l, about 1.25-10 µmol/l, about 1.5-10 µmol/l, about 1.75-10 µmol/l, about 2.0-10 µmol/l, about 2.5-10 µmol/l, about 3.0-10 µmol/l, about 4.0-10 µmol/l, about 5.0-10 µmol/l, about 6.0-10 µmol/l, about 7.0-10 µmol/l, about 8.0-10 µmol/l, about 9.0-10 µmol/l, about 0.01-50 µmol/l, about 0.05-5.0 µmol/l, about 0.075-5.0 µmol/l, about 0.1-5.0 µmol/l, about 0.5-5.0 µmol/l, about 0.75-5.0 µmol/l, about 1.0-5.0 µmol/l, about 1.25-5.0 µmol/l, about 1.5-5.0 µmol/l, about 1.75-5.0 µmol/l, about 2.0-5.0 µmol/l, about 2.5-5.0 µmol/l, about 3.0-5.0 µmol/l, about 4.0-5.0 µmol/l, about 0.01-3.0 µmol/l, about 0.05-3.0 µmol/l, about 0.075-3.0 µmol/l, about 0.1-3.0 µmol/l, about 0.5-3.0 µmol/l, about 0.75-3.0 µmol/l, about 1.0-3.0 µmol/l, about 1.25-3.0 µmol/l, about 1.5-3.0 µmol/l, about 1.75-3.0 µmol/l, about 2.0-3.0 µmol/l, about 0.01-1.0 µmol/l, about 0.05-1.0 µmol/l, about 0.075-1.0 µmol/l, about 0.1-1.0 µmol/l, about 0.5-1.0 µmol/l, about 0.75-1.0 µmol/l, about 0.09-35 µmol/l, about 0.09-3.2 µmol/l, and more preferably about 0.05-1.0 µmol/l, about 0.075-1.0 µmol/l, about 0.1-1.0 µmol/l, about 0.5-1.0 µmol/l, and about 0.75-1.0 µmol/l.

In one embodiment, a therapeutic or prophylactic drug of the present invention can be targeted for any animal with a corneal endothelium, such as mammals. Such a drug preferably is intended for treatment or prevention of a primate corneal endothelium. The subject of treatment or prevention is preferably a human corneal endothelium.

In one embodiment, the corneal endothelial disease, disorder or condition targeted by the therapeutic and prophylactic drug of the present invention is a corneal endothelial disease, disorder or condition requiring cell proliferation, suppression of cellular disorder or suppression of cellular senescence. Examples thereof include, but are not limited to, disorders associated with corneal endotheliitis, senescence, ocular surgery, trauma, sustained decrease in corneal endothelial density post-corneal transplantation, Fuchs' corneal endothelial dystrophy and the like.

In another aspect, the present invention provides a method of treating or preventing a corneal endothelial disorder requiring cell proliferation, comprising the step of administering an effective amount of a p38 MAP kinase inhibitor to a subject in need thereof.

Subjects of administration (transplantation) of the therapeutic or prophylactic drug or method of the present invention include mammals (e.g., human, mouse, rat, hamster, rabbit, cat, dog, cow, horse, sheep, monkey and the like), but primates are preferred and humans are especially preferred. Corneal endothelial therapy in primates has not attained satisfactory results up to this point. In this context, the present invention provides a groundbreaking therapeutic method and medicament. In particular, the present invention is the first to attain excellent therapeutic results by using a p38 MAP kinase inhibitor in cases using a wound model of a corneal endothelium. The dosage and frequency of dosing vary depending on the symptom, age, weight, or dosing format. For example, when used as eye drops, a formulation containing about 0.0001-0.5 w/v %, preferably about 0.003-0.03 w/v %, of effective ingredient can generally be administered 1-10 times, preferably 1-6 times, more preferably 1-3 times a day with about 0.01-0.1 mL per dose for adults. When the medicament of the present invention is injected into the anterior chamber, a concentration that is $1/10$ to $1/1000$ of the above-described concentration may be used. Those skilled in the art can appropriately select the type and concentration of p38 MAP kinase inhibitor depending on the condition of the disease.

Reference literatures such as scientific literatures, patents, and patent applications cited herein are incorporated herein by reference to the same extent that the entirety of each document is specifically described.

As described above, the present invention has been described by showing preferred embodiments to facilitate understanding. The present invention is described below based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

Examples of culturing normal corneal endothelial cells of the present invention are disclosed hereinafter. Experimental animals were used in accordance with the International Guiding Principles for Biomedical Research involving Animals, laws for the protection and management of animals, and standards for caring and management of experimental animals. Further, the present experiment was conducted in accordance with the Guidelines of the Association for Research in Vision and Ophthalmology on the Use of Animals in Ophthalmic and Vision Research. Tissue isolation was approved by animal experiment ethics committee of Shiga Laboratory, Nissei Bills Co., Ltd. (Ohtsu, Japan) and animal experiment committee of Eve Bioscience, Co., Ltd. (Hashimoto, Japan). Further, Biological samples or the like, when applicable, were handled in compliance with the standards enacted by the Ministry of Health, Labour and Welfare, Ministry of Education, Culture, Sports, Science and Technology, or the like and, if applicable, based on the Helsinki Declaration or ethical codes prepared based thereon. For the donation of eyes used for the research, consent was obtained from close relatives of all deceased donors.

Experimental Methodology: Research-Grade Human Corneal Tissue 12 human donor corneas were obtained from SightLife™ Eye Bank. All corneas were stored at 4° C. in a storage medium (Optisol; Chiron Vision Corporation, Irvine, Calif.) over a period of less than 14 days prior to primary culture.

(Statistical Analysis)

The statistically significant difference (P value) in the means value comparing two samples was determined with Student's t-test. The statistically significant difference in comparing multiple sample sets was analyzed by using Dunnett's multiple comparison test. The values shown in the graph represent mean±SE.

(Materials and Methods)

*Human corneal endothelial cells (HCEC, where the cells were obtained and culturing method thereof): HCEC was cultured as follows. In short, Descemet's membrane including corneal endothelial cells was peeled off from a corneal for research purchased from the Seattle Eye Bank, and the corneal endothelial cells were mechanically peeled off with a basal membrane. After collagenase (ROCHE catalog No: 10 103 586 001) was used to detach and collect the corneal endothelial cell from the basal membrane (typically 1 mg/mL collagenase A (Roche Applied Science) was used for treatment at 37° C. for 2 hours), the cells were subjected to primary culture. The medium used was Opti-MEM I Reduced-Serum Medium, Liquid (INVITROGEN catalog No.: 31985-070) to which 8% fetal bovine serum (FBS) (BIOWEST, catalog No.: S1820-500), 200 mg/ml of $CaCl_2.2H_2O$ (SIGMA catalog No.: C7902-500G), 0.08% of chondroitin sulfate (SIGMA catalog No.: C9819-5G), 20 μg/ml of ascorbic acid (SIGMA catalog No.: A4544-25G), 50 μg/ml of gentamicin (INVITROGEN catalog No.: 15710-064) and 5 ng/ml of EGF (INVITROGEN catalog No.: PHG0311) were added and acclimated for a 3T3 feeder cell. Specifically, after digestion at 37° C., HCEC obtained from individual corneas was resuspended in a culture medium and plated on a well of a 12-well plate coated with FNC Coating Mix®. The culture medium was prepared in accordance with a partially-modified disclosed protocol. In short, a basal cultural medium containing OptiMEM-I (Life Technologies), 8% FBS, 5 ng/mL of epithelial growth factor (EGF) (Sigma-Aldrich Co., St. Louis, Mo.), 20 μg/mL of ascorbic acid (Sigma-Aldrich), 200 mg/L calcium chloride (Sigma-Aldrich), 0.08% chondroitin sulfate (Wako Pure Chemical Industries, Osaka) and 50 μg/mL of gentamicin was prepared and an acclimated medium was collected after inactivated 3T3 fibroblasts were cultured. The 3T3 fibroblasts were inactivated as previously described. In short, confluent 3T3 fibroblasts were incubated for 2 hours at 37° C. under 5% $CO^2$ with 4 μg/mL mitomycin C (MMC) (Kyowa Hakko Kirin Co., Ltd, Tokyo) and then treated with trypsin and plated on a plastic plate at a density of $2\times10^4$ cells/$cm^2$. HCEC was cultured under a humidified atmosphere at 37° C. in 5% $CO^2$. The culture medium was exchanged every 2 days. Once HCEC reached confluence in 14-28 days, HCEC was rinsed with $Ca^{2+}$ and $Mg^{2+}$-free PBS, treated with trypsin with 0.05% trypsin-EDTA for 5 minutes at 37° C., and subcultured at a ratio of 1:2.

*Method of observing cells such as staining (histological test): Cells were observed with a phase difference microscope. Further, after immobilizing the cells, ZO-1 and $Na^+/K^+$-ATPase were used as function associated markers. Immunostaining was applied to the cells for observation with a fluorescence microscope. For tissue staining inspection, the cultured HCEC was placed in Lab-Tek™ Chamber Slides™ (NUNC A/S, Roskilde, Denmark), immobilized with 4% formaldehyde for 10 minutes at room temperature (RT), and incubated for 30 minutes with 1% bovine serum albumin (BSA). Specifically, cultured HCEC on Lab-Tek™ Chamber Slides™ (NUNC A/S, Roskilde, Denmark) were immobilized in 4% formaldehyde for 10 minutes at room temperature and incubated for 30 minutes with 1% bovine serum albumin (BSA). To investigate the phenotype of the CEC, immunohistological chemical analysis was performed on ZO-1 (Zymed Laboratories, Inc., South San Francisco, Calif.), which is a close bond associated protein, $Na^+/K^+$-ATPase (Upstate Biotec, Inc., Lake Placid, N.Y.), which is a pumping function associated protein, fibronectin (BD, Franklin Lakes, N.J.) and actin. ZO-1 and $Na^+/K^+$-ATPase were used as markers associated with functions of CEC, and fibronectin and type 1 collagen were used to assess fibroblast-like changes. Stained actin was used to assess the cell form. ZO-1, $Na^+/K^+$-ATPase, and type 1 collagen and fibronectin were stained with a 1:200 dilution of ZO-1 polyclonal antibodies, $Na^+/K^+$-ATPase monoclonal antibodies, and fibronectin monoclonal antibodies, respectively. For secondary antibodies, a 1:2000 dilution of Alexa Fluor® 488 labeling or Alexa Fluor® 594 labeling goat antimouse IgG (Life Technologies) was used. Actin was stained with 1:400 dilution of Alexa Fluor® 488 labelling phalloidine (Life technologies). Cellular nuclei were then stained with DAPI (Vector Laboratories, Inc., Burlingame, Calif.) or PI (Sigma-Aldrich). Slides were then observed under a fluorescence microscope (TCS SP2 AOBS; Leica Microsystems, Welzlar, Germany).

*Western blot: Electrophoresis was applied to a protein extracted and obtained in a RIPA buffer with 7.5% polyacrylamide. The isolated protein was transferred onto a PVDF membrane (PALL LIFE SCIENCE, catalog number: EH-2222). A Tris buffered saline (10 mM Tris-HCl, pH 7.4; 100 mM NaCl) complemented with 0.1% (vol/vol) polyethylene sorbitan monolaurate (Nacalai Tesque, catalog number: 28353-85) (TBS-T) and 5% NON FAT DRY MILK (CELL SIGNALING, catalog number: 9999) and a blotted membrane were incubated for 1 hour for a blocking operation. The membrane was then immersed in 1:1000 dilution of TBS-T complemented with antibodies to p27 (SC-527, Santa Cruz), p21 (2946, Cell Signaling), p16 (4824, Cell Signaling), p-pRb (9308, Cell Signaling), cyclin D1 (2926, Cell Signaling), cyclin D3 (2936, Cell Signaling), pp38 (4631, Cell Signaling), p-ATF2 (SC-8398, Santa Cruz), and GAPDH (2118, Cell Signaling) and reacted for 1 hour at room temperature. After washing three times with T-TBS and incubating with a mouse-IgG antibody HRP complex (CELL SIGNALING, catalog number: 7074P2) and rabbit-IgG antibody HRP complex (GE Healthcare, catalog number: NA934) and washing, a band illuminated with an ECL-ADVAVCE (GE Healthcare Japan, catalog number: RPN2135V) was detected.

*Immunostaining: After washing cells that have reached confluence with PBS (Nissui Pharmaceutical, catalog number: 5913), the cells were immobilized for 10 minutes with ice-cooled ethanol (Nacalai Tesque, catalog number: 14713-95) and acetic acid (WAKO catalog number: 017-00256) (95:5).

The cells were incubated for 1 hour with a Tris buffered saline (10 mM Tris-HCl, pH 7.4; 100 mM NaCl) complemented with 10% bovine fetal serum and 0.1% (vol/vol) polyethylene sorbitan monolaurate (NacalaiTesque, catalog number: 28353-85) (TBS-T) for a blocking operation. Rabbit anti-human ZO-1 antibodies (1:200) and mouse anti-human $Na^+/K^+$-ATPase antibodies (1:200) were used as primary antibodies for a reaction for 1 hour at room temperature. A dilution ratio of 1:200 or 1:1000 was appropriately used.

A reaction was then carried out for 1 hour at room temperature with ALEXA FLUOR 488 (INVITROGEN (catalog number: A21206)) and ALEXA FLUOR 594 (INVITROGEN (catalog number: A21203)) diluted 1000-fold in TBS-T. After washing with PBS, they were enclosed in a slide with VECTASHIELD WITH DAPI (VECTOR LABORATORIES (catalog number: 94010)) and observed with a confocal microscope (Leica).

*Antibodies to $Na^+/K^+$-ATPase: from MILLIPORE (MILLIPORE catalog number: 05-369) were used.

*Antibodies to ZO-1: from INVITROGEN (INVITROGEN catalog number: 339100) (mice) and ZYMED LABORATORIES (ZYMED LABORATORIES catalog number: 61-7300) (rabbits) were used.

*Antibodies to GAPDH: from ABCAM (catalog number: ab36840) were used.

*Secondary antibodies (HPR binding anti-rabbit IgG secondary antibodies, Cell Signaling Technology (catalog number: 7074)

*Secondary antibodies (anti-rabbit IgG secondary antibodies) Cell Signaling Technology (catalog number: 7076)

*Cytokine antibodies

Corneal endothelial cells were cultured in the presence of 10 μM SB203580, and culture supernatant was collected as a sample solution. Cytokines in the culture supernatant were comprehensively measured semi quantitatively with a Proteome Profiler (# ARY005, R&D). A membrane blotted with cytokine antibodies was placed in a tray. 2 ml of blocking solution was added and the membrane was incubated for 1 hour at room temperature. Biotin antibodies were added to the sample solution and incubated for 1 hour at room temperature. The blocking solution was discarded. The membrane was immersed in an antibody solution and incubated overnight at 4° C. After washing the membrane, 2 ml of HRP labeling streptavidin solution diluted with a blocking solution was added and the membrane was incubated at room temperature for 30 minutes. After washing the membrane, a substrate solution was added for detection with LAS400 (Fuji Film).

*PCR: PCR was carried out on each laminin chain and integrin chain by RT-PCR (reverse transcription polymerase chain reaction). A primer was purchased from the oligonucleotide synthesis company INVITROGEN and then desalinized for use. RNEasy Mini Kit (QIAGEN, catalog number: 74106) was used for extracting the entire RNA from cells. The Descemet's membrane including corneal endothelial cells were peeled off from a cornea for research purchased from the Seattle Eye Bank and the corneal endothelial cells were mechanically peeled off with the basal membrane for use in RNA extraction from the corneal endothelial cells. A reverse transcription reaction (42° C., 60 minutes) was performed on RNA with ReverTra Ace (TOYOBO (catalog number: TRT-101)), and CD166 and CD73 were amplified with TAKARA TaqHotStart Version (TAKARA RIO, catalog number: RR001A) with GAPDH as the internal standard. The same amount of cDNA was amplified by the following primer pairs and PCR instrument (GeneAmp 9700; Applied Biosystems). The primers shown below were used in the PCR reaction. The primers were obtained from Life Technologies Japan (catalog number: 10336022).

*IL6-F:
　　　　　　　　　　　　　　　　　(SEQ ID NO: 1)
CACAAGCGCCTTCGGTCCAGTT

*IL6-R:
　　　　　　　　　　　　　　　　　(SEQ ID NO: 2)
TCTGCCAGTGCCTCTTTGCTGC

*GAPDH-F:
　　　　　　　　　　　　　　　　　(SEQ ID NO: 3)
GAGTCAACGGATTTGGTCGT

*GAPDH-R:
　　　　　　　　　　　　　　　　　(SEQ ID NO: 4)
TTGATTTTGGAGGGATCTCG

Electrophoresis is applied to an amplified DNA fragment with 1.5% agarose gel (Nacalai Tesque, catalog number: 01149-76) and the fragment was detected by staining with ethidium bromide (Nacalai Tesque, catalog number: 14603-51).

*The amount of IL-6 expression of human corneal endothelial cells was quantified by RT-PCR by the following method. Human corneal endothelial cells (n=3, passage 5) were cultured for 20 days in the presence of 10 μM of SB203580, and then RNA was extracted with RneasyMini (QIAGEN). 277 ng of total RNA was reverse-transcribed with RevertraAce (Toyobo) and cDNA synthesized into a template to perform PCR. 10 μl of PCR solution containing 1 μl of reaction mixture from single strand cDNA synthesis was heated for 1 minute at an initial temperature of 94° C. and then 1 minute at 94° C., 30 seconds at 54° C., and 30 seconds at 72° C. The temperature cycle was repeated 30 times.

IL-6 sense primer: cacaagcgccttcggtccagtt (SEQ ID NO: 1)
IL-6 antisense primer: tctgccagtgcctctttgctgc (SEQ ID NO: 2)

*ELISA (BrdU): Cells were seeded on a 96-well culture plate at a seeding density of 5000 cells/well. 5-bromo-2'-deoxyuridine (BrdU) was then added to a medium and the cells were cultured overnight. The medium was removed and an immobilizing solution (Amersham cell proliferation biotrak ELISA system, version 2) was added and the cells were incubated for 30 minutes at room temperature. The immobilizing solution was then removed and a blocking solution (Amersham cell proliferation biotrak ELISA system, version 2) was added and the cells were left standing at room temperature for 30 minutes. The blocking solution was then removed and peroxidase binding anti-BrdU antibodies were added, and the cells were left standing for 90 minutes at room temperature. The plate was washed three times with a washing buffer, and TMB (3,3',5,5'-tetramethylbenzidine) substrate (Amersham cell proliferation biotrak ELISA system, version 2) was added and the cells were left standing for 5-30 minutes. The reaction was stopped with 1M sulfuric acid to measure the absorbance at 450 nm with a plate reader. The results are shown as a mean value of 5 measurements±standard error.

*ELISA (IL-6): After human corneal endothelial cells (n=3, passage 5) were cultured for 20 days in the presence of 10 μM of SB203580, the medium was exchanged with a fresh medium. The amount of IL-6 protein in a culture supernatant collected after 7 days was quantified in accordance with the manual of DuoSetELISA human IL-6 (R & D Cat # DY206). IL-6 antibodies (2.0 μg/mL) were covered overnight at room temperature in phosphate-buffered saline (PBS) at 100 μL/well on a flat bottom plate (nunc). The plate was washed with PBS, 0.05% (v/v) Tween 20 (PBS/Tween), and blocking was performed for 2 hours with PBS/Tween (PTG) supplemented with 1% serum albumin (Nacalai Tesque). 0.1 ml of culture supernatant was added and the cells were incubated for 2 hours at room temperature. After washing, anti-IL-6 antibodies treated with biotin were added and the cells were incubated for 2 hours at room temperature. After washing, horseradish peroxidase binding streptavidin was added and the cells were incubated for 20 minutes. The plate was washed and the bound peroxidase was detected with a substrate solution (R&D Systems Cat # DY999). The coloring reaction was stopped with 2M of $H_2SO_4$ to read out the plate with Multimax (Promega) at 450 nM.

Example 1

Suppression of Cyclin Dependent Kinase Inhibiting Factors and Transition in Cell Cycle of Corneal Endothelial Cells by p38 MAP Kinase Signal Inhibition The present Example shows that p38 MAP kinase signal inhibition suppresses cyclin dependent kinase inhibiting factors and transitions cell cycle of corneal endothelial cells.

In accordance with the aforementioned preparation examples, corneal endothelial cells cultured from a cornea for research imported from the Seattle Eye Bank were cultured for use in the following study. A p38 MAP kinase inhibitor SB203580 (13067, Cayman) was added to a cell culture medium. After 20 days, the expression of cyclin dependent kinase inhibiting factors p27, p21, and p16 was studied by Wester blotting. Each of p27, p21, and p16 was suppressed by the addition of SB203580 (FIG. 1 A shows, from the top, p27, p21, p16 and GAPDH. The left lane shows the control, the middle shows 10 μM of SB203580, and the right lane shows 30 μM of SB203580). It is reported that p27, p21, and p16 are cyclin dependent kinase inhibiting factors that negatively regulates cell proliferation of corneal endothelial cells.

As molecules associated with the transition of the G1/S phase of a cell cycle, Rb protein phosphorylation, and cyclin D1 and D3 expression were studied by Western blotting. The results are shown in FIG. 1. The expression of these molecules was promoted by the addition of SB203580 after each of 12 hours and 24 hours (B; 2 rows each of p-pRb, cycline D1, cycline D3 and GAPDH are shown from the top. In each of the two rows, the top side shows the control and the bottom side shows stimulation by SB203580 (10 μM). The left lane shows 12 hours and the right lane shows 24 hours). Further, it was confirmed by Western blotting after 20 days from a stimulation that phosphorylation of a downstream molecule of a p38 MAP kinase signal, ATF2, was suppressed by SB203580 (C; shows, from the top, pp38, p-ATF2, and GAPDH. The left lane shows the control, the middle shows 10 μM of SB203580, and the right lane shows 30 μM of SB203580). The above results demonstrate that p38 MAP kinase, signal inhibition suppresses cyclin dependent kinase inhibiting factors and transitions a cell cycle of corneal endothelial cells. This is demonstrated for the first time for corneal endothelial cells as far as the inventors are aware.

Example 2

Promotion of Cell Proliferation of Corneal Endothelial Cells by p38 MAP Kinase Inhibitor The present Example demonstrate that a p38 MAP kinase inhibitor promotes cell proliferation of corneal endothelial cells.

Cultured human corneal endothelial cells were stimulated with a p38 MAP kinase inhibitor SB203580. After three days, immunostaining was applied with a cell proliferation marker Ki67 (Dako, M7240) based on the experimental methodology discussed herein. The methodology was as discussed above.

Figure 2:
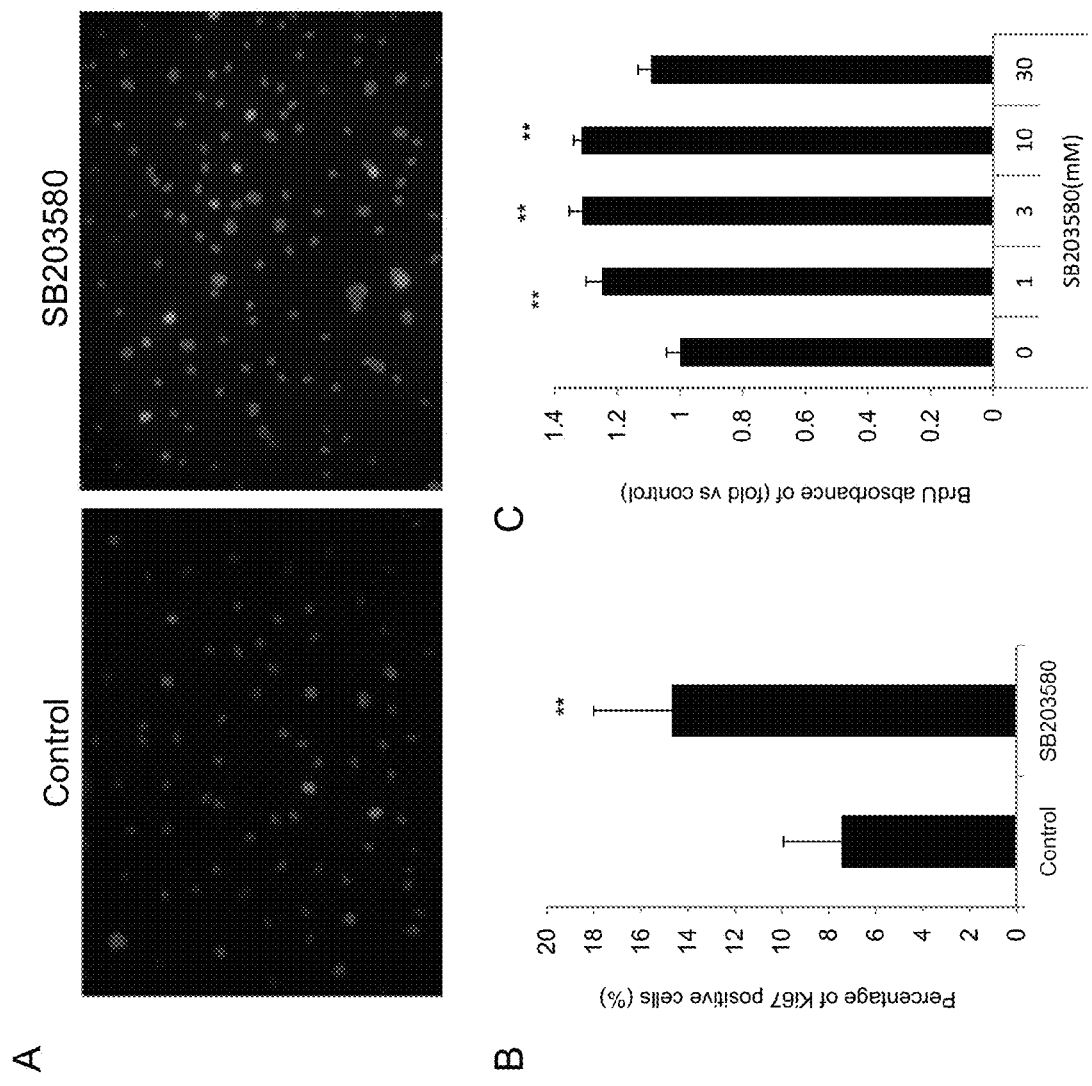
FIG. 2 shows that p38 MAP kinase signal inhibition promotes corneal endothelial cell proliferation. Cultured human corneal endothelial cells were stimulated with a p38 MAP kinase inhibitor SB203580 and immunostained with a cell proliferation marker Ki67 after 3 days. Expression of Ki67 was observed in significantly more cells by a stimulation with SB203580 (A, B; The picture on the left side of A shows the control and the right side shows SB203580 stimulation (10 μM). B shows the percentage of Ki67 positive cells. The vertical axis is the ratio of Ki67 positive cells (%). The left bar shows the control and the right bar shows SB203580 stimulation (10 μM)). Further, when BrdU uptake was similarly studied as an indicator as a cell proliferation marker after three days by ELISA, BrdU uptake was significantly promoted by a stimulation with SB203580 (C; The vertical axis shows BrdU uptake (relative value with respect to a control) and the horizontal axis shows results of stimulation with various amounts of SB203580 (0 μM, 1 μM, 3 μM, 10 μM, and 30 μM)). The above results demonstrate that p38 MAP kinase signal inhibition promotes corneal endothelial cell proliferation.

The results are shown in FIG. 2. Expression of Ki67 was observed in significantly more cells by a stimulation with SB203580 (A, B). Similarly, as a cell proliferation marker, uptake of BrdU was studied after 3 days by ELISA as an indicator. BrdU uptake was significantly promoted by a stimulation with SB203580 (C). The above results show that p38 MAP kinase signal inhibition promotes cell proliferation of corneal endothelial cells.

Example 3

Promotion of Corneal Endothelial Cell Proliferation with p38 MAP Kinase Inhibitor in a Partial Rabbit Corneal Endothelial Disorder Model The present Example studied whether p38 MAP kinase signal inhibition promotes corneal endothelial cell proliferation in a living organism by using a partial rabbit corneal endothelial disorder model.

A stainless steel chip with a diameter of 7 mm was immersed in liquid nitrogen and cooled. The chip was contacted with the center portion of a corneal of a Japanese white rabbit (obtained from Oriental Bioservice) for 15 seconds under general anesthesia, such that corneal endothelial cells at the center portion partially fell off. Eye drops of SB203580 adjusted to 10 mM was then administered 4 times a day for 2 days at 50 μl per dose. As a control, eye drops of a base agent were administered in an eye in which a partial corneal endothelial disorder was similarly created, and a picture was taken. Further, the rabbit was euthanized and the corneal was extracted. The wounded area of the corneal endothelium was stained with alizarin red S (Nacalai Tesque, CI-58005) and observed. Furthermore, immunostaining was applied to corneal tissue with the cell proliferation marker Ki67. The same methodology as the aforementioned Examples or the like was used for immunostaining.

Figure 3:
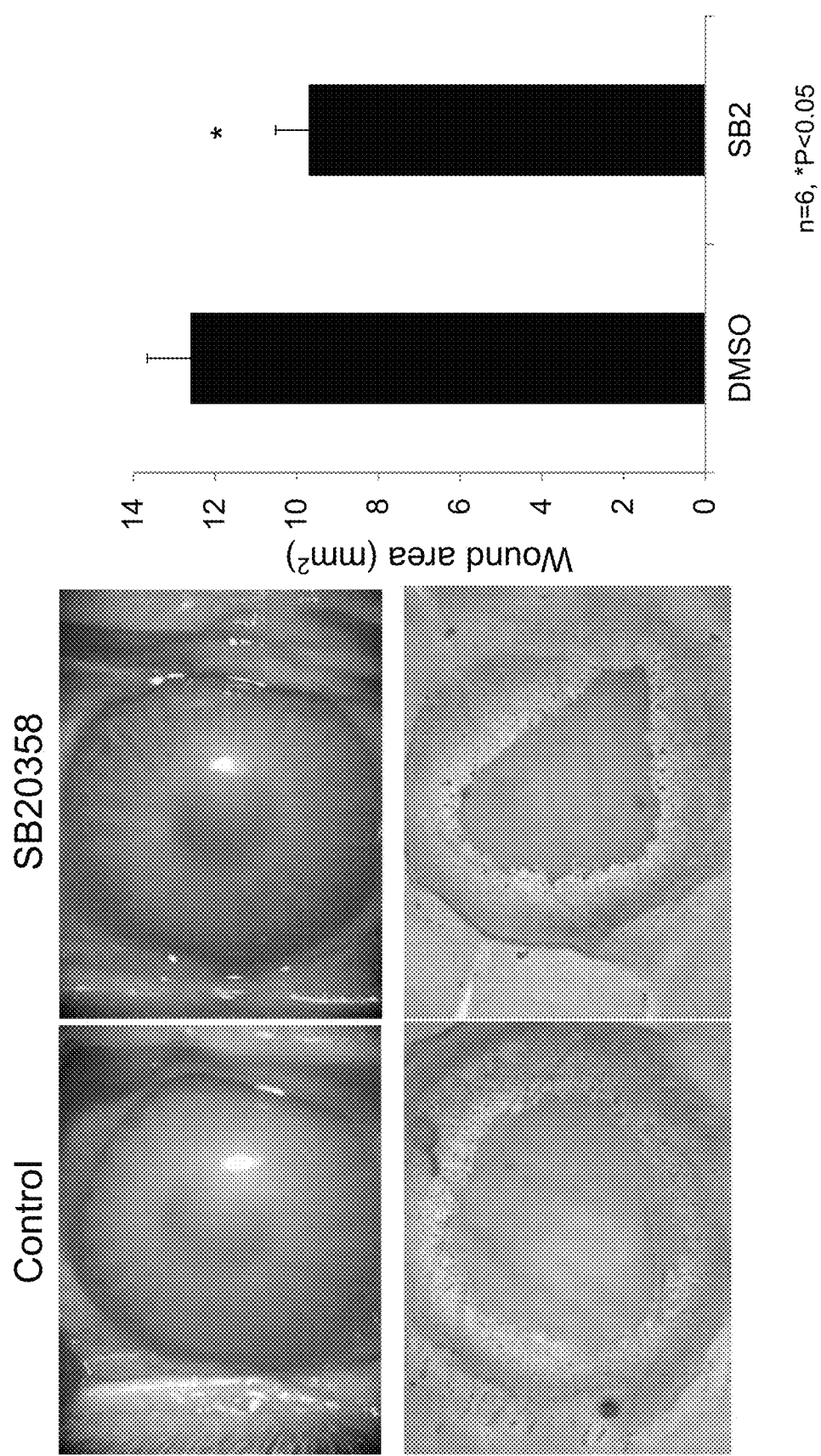
FIG. 3 shows that administration of eye drops of a p38 MAP kinase inhibitor promotes wound healing in a partial rabbit corneal endothelial disorder model. A partial rabbit corneal endothelial disorder model was used to study whether p38 MAP kinase signal inhibition promotes cell proliferation of corneal endothelium in a living organism. A stainless steel chip with a diameter of 7 mm was immersed in liquid nitrogen, cooled, and then contacted with the center of a cornea of a white rabbit under general anesthesia for 15 seconds, such that corneal endothelial cells at the center portion partially fell off. SB203580 adjusted to 10 mM was then administered as eye drops 4 times a day for 2 days at 50 μl per dose (Left side panel of pictures, right side. The picture on the top right shows the overall image, and the picture on the bottom right shows the wounded portion). As a control, eye drops of a base agent were adminisetered into an eye where a partial corneal endothelial disorder was similarly made (Left side panel of pictures, left side. The picture on the top left shows the overall image, and the picture on the bottom left side shows the wounded portion). Early recover of transparency in the cornea was confirmed in the SB203580 eye drops group from a picture of the anterior ocular segment on day 2. Further, when the rabbit was euthanized to remove the cornea and the wounded area of the corneal endothelium was stained with alizarin stain, the wounded area in the SB203580 eye drops group was diminished more than the control (Left side panel of pictures, each picture on the bottom side). Further, when a total of 6 eyes each were studied, the wound area was significantly diminished in the SB203580 eye drops group (right graph, vertical axis indicates the wound area (mm$^2$), the right indicates DMSO (control), and left indicates the result of stimulation by SB203580. * indicates statistical significance at $p<0.01$), thus demonstrating that p38 MAP kinase signal inhibition promotes wound healing in a corneal endothelium.

The results are shown in FIG. 3. FIG. 3 shows a picture of the anterior eye section after administration of eye drops of SB203580 adjusted to 10 mM 4 times a day for 2 days at 50 μl per dose on the right side of the left panel picture. The picture on the top right shows the overall image. The picture on the bottom right shows the wounded area of the corneal endothelium by alizarin staining. On the left side, the picture on the top right shows the overall image and the picture on the bottom right shows the wounded area of the corneal endothelium by alizarin staining. It was confirmed from the picture of the anterior eye section that transparency of a corneal recovered quickly in the SB203580 eye drops group on day 2. Further, the rabbit was euthanized and the corneal was extracted. When the wounded area of the corneal endothelium was stained by alizarin staining, the area showed more contraction in the SB203580 eye drops group relative to the control. Further, when total of 6 eyes each were studied, it was shown that the wound area contracted significantly more in the SB203580 eye drops group and p38 MAP kinase signal inhibition promoted wound healing of the corneal endothelium. Rabbit models are known to be excellent models, which allow extrapolation for primates, especially humans. Thus, it is expected in view of the results of the present Example that p38 MAP kinase signal inhibition also promotes wound healing in the corneal endothelium in primates including humans.

Figure 4:
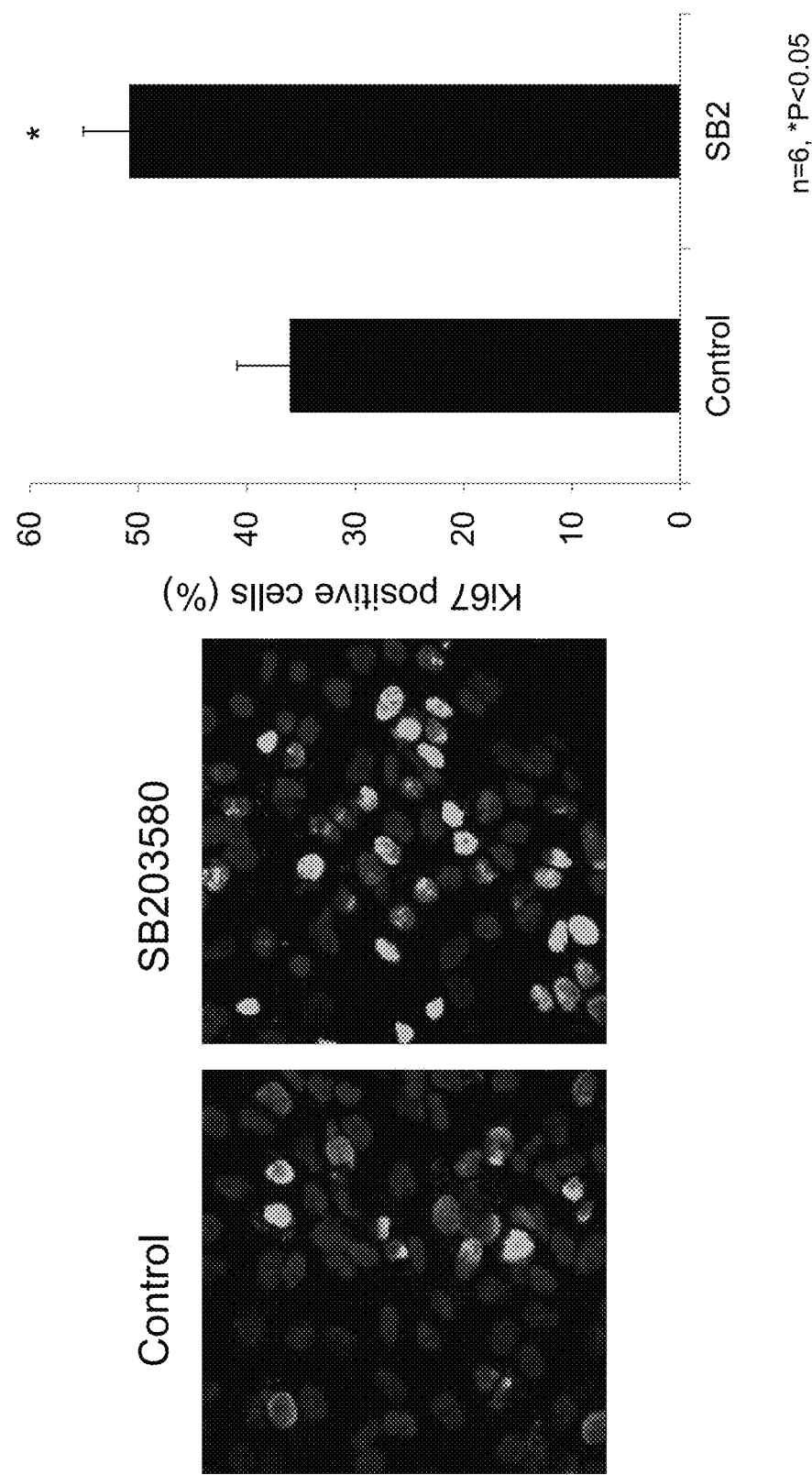
FIG. 4 shows that administration of eye drops of a p38 MAP kinase inhibitor promotes corneal endothelial cell proliferation in a partial rabbit corneal endothelial disorder model. In addition to FIG. 3, immunostaining was further performed on corneal tissue with a cell proliferation marker Ki67 (left picture; the left side in the picture shows the control and the right side shows the SB203580 (10 mM) eye drops group. The right side graph shows the ratio of Ki67 positive cells for the control (left) and SB203580 eye drops (10 mM)). Ki67 expression was observed in significantly more cells by eye drops of SB203580. The above results show that p38 MAP kinase signal inhibition promotes corneal endothelial cell proliferation in a living organism.

Furthermore, FIG. 4 shows results of immunostaining of corneal tissue with a cell proliferation marker Ki67. The picture on the left shows control on the left side of the picture and the right side shows a typical example of an individual applied with an SB203580 eye drops (10 mM). The graph on the right shows the ratio of Ki67 positive cells for the control (left) and SB203580 stimulation (10 mM). Expression of Ki67 was observed in significantly more cells by a stimulation with SB203580. The above results show that p38 MAP kinase signal inhibition promotes corneal endothelial cell proliferation in a living organism.

Example 4

Suppression of Decrease in Corneal Endothelial Cell Density by p38 MAP Kinase Inhibitor The present Example shows that p38 MAP kinase signal inhibition suppresses decrease in cell density due to hypertrophy of cells that occurs in a culturing environment.

Cellular senescence-like decrease similar to a living organism, such as hypertrophy and decrease in density of cells, occurs from cell culture. In this regard, the effect of p38 MAP kinase signal inhibition on cellular senescence-like decrease such as decrease in corneal endothelial cell density was studied.

Figure 5:
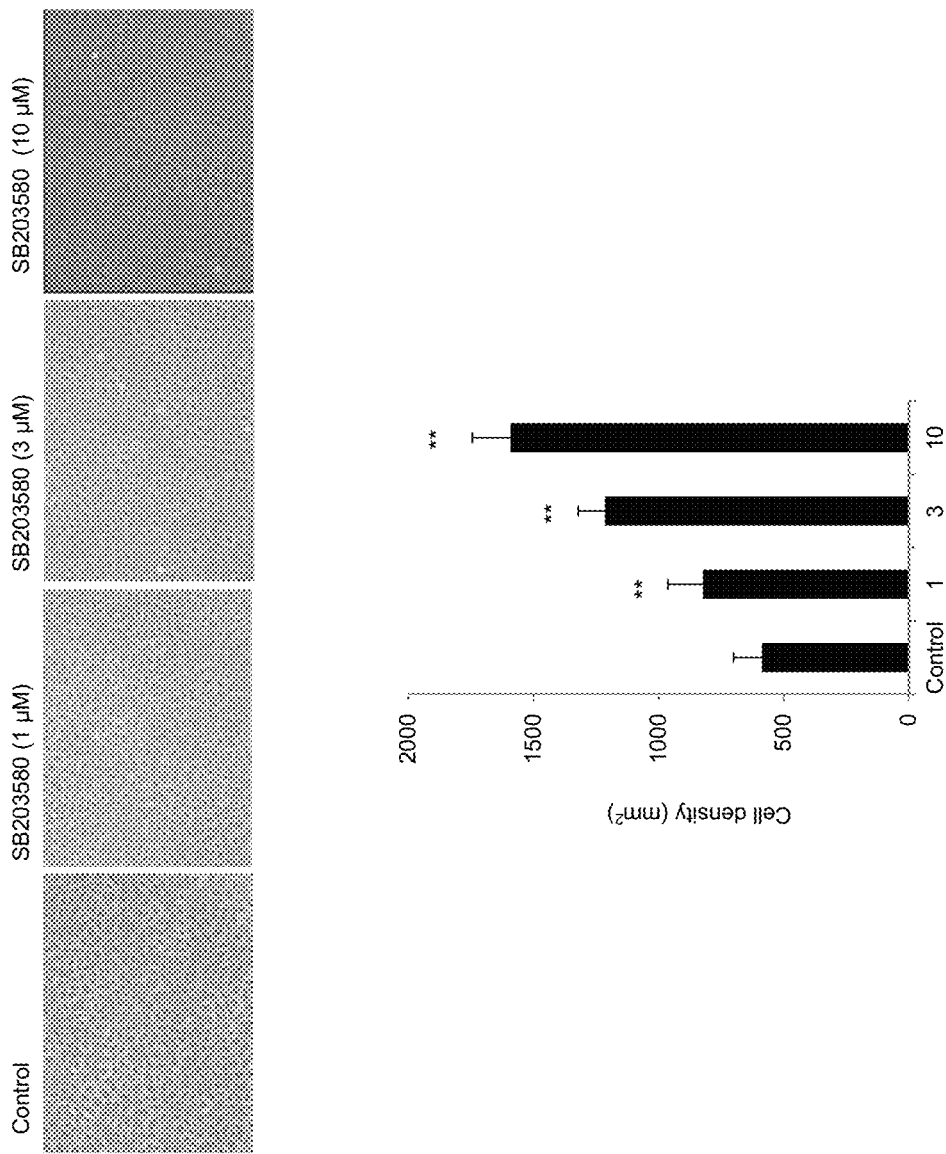
FIG. 5 shows that p38 MAP kinase signal inhibition suppresses a decrease in cell density due to hypertrophy of cells that occurs in a culture environment. For corneal endothelial cells, cell density decreases about 0.5% annually with age in a living organism. Further, the cell density also decreases due to various corneal endothelial diseases. Cell culture causes hypertrophy of cells and cellular as in a living organism and cellular senescence like reduction as in a living organism, which is a decrease in cell density. In this regard, the effect of p38 MAP kinase signal inhibition was studied on cellular senescence like reduction, which is a decrease in corneal endothelial cell density. Pictures from a phase difference microscope of cultured human corneal endothelial cells stimulated by using a p38 MAP kinase inhibitor SB203580 at various concentrations after 20 days are shown (Top panel shows, from the left, control, SB203580 1 μM, 3 μM, and 10 μM). Decrease in cell density due to culturing was inhibited and the cell density increased in an SB203580 concentration-dependent manner (bottom panel: vertical axis indicates cell density (mm$^2$) and the horizontal axis indicates, from the left, control, SB203580 1 μM, 3 μM, and 10 μM. ** indicates statistical significance ($p<0.05$) with respect to the control).

The results are shown in FIG. 5. Pictures from a phase difference microscope are shown from 20 days after stimulating cultured human corneal endothelial cells at various concentrations by using a p38 MAP kinase inhibitor SB203580 (top panel). Decrease in cell density due to culture was inhibited in a SB203580 concentration dependent manner and the cell density increased (bottom panel).

The above result shows that a p38 MAP kinase inhibitor suppresses decrease in corneal endothelial cell density.

Example 5 p38 MAP Kinase Inhibitor Maintains Corneal Endothelial Cell Functions, Pumping Function and Barrier Function, and Suppresses Decrease in Density In the present Example, it was confirmed whether p38 MAP kinase signal inhibition maintains pumping and barrier functions and inhibits decrease in cell density due to culturing. Cultured human corneal endothelial cells were stimulated at various concentrations by using a p38 MAP kinase inhibitor SB 203580. After 20 days, immunostaining was performed with $Na^+/K^+$-ATPase and ZO-1 as makers for functions of corneal endothelial cells, pumping function and barrier function, respectively.

Figure 6:
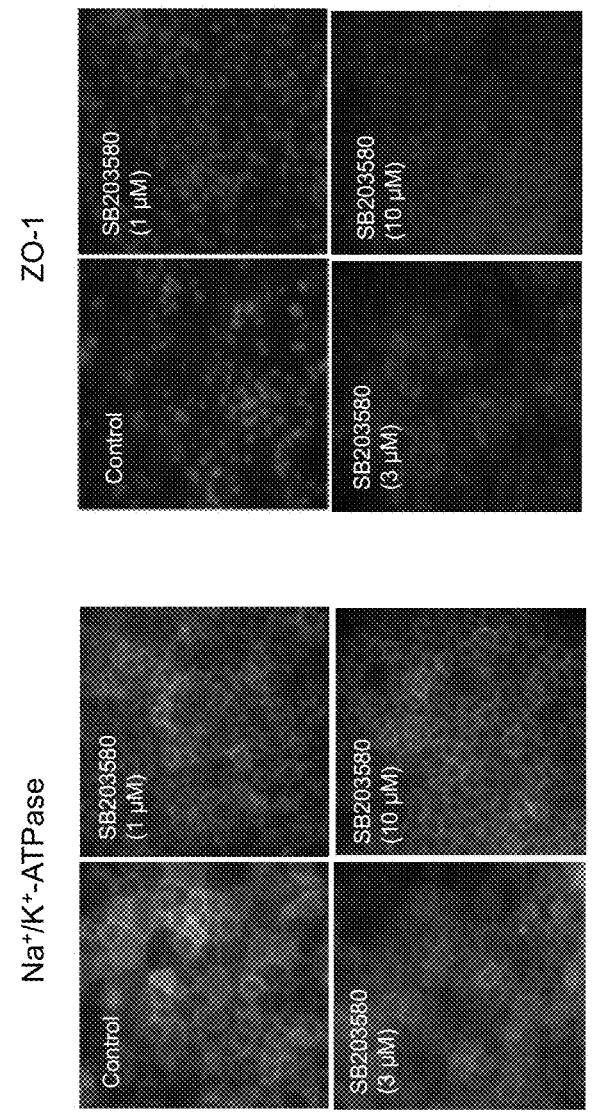
FIG. 6 shows that p38 MAP kinase signal inhibition maintains pumping and carrier functions to inhibit a decrease in cell density. Cultured human corneal endothelial cells were stimulated by using a p38 MAP kinase inhibitor SB203580 at various concentrations and immunostaining was applied after 20 days with Na$^+$/K$^+$-ATPase and ZO-1 as markers for the pumping function and barrier functions, which are functions of the corneal endothelial cells, respectively (left: Na$^+$/K$^+$-ATPase, right: ZO-1. In each panel, the top left shows a control, top right shows SB203580 1 μM, bottom left shows SB203580 3 μM, and bottom right shows SB203580 10 μM). The corneal endothelial cells were demonstrated to express Na$^+$/K$^+$-ATPase and ZO-1 and to maintain normal functions in all cells by p38 MAP kinase signal inhibition.

The results are shown in FIG. 6. It is shown that corneal endothelial cells express $Na^+/K^+$-ATPase and ZO-1 in all cells while maintaining normal functions, and decrease in cell density and hypertrophy of the corneal endothelial cells are suppressed by p38 MAP kinase signal inhibition. This is understood as p38 MAP kinase signal inhibition suppressing cellular senescence while maintaining normal cellular functions without losing cellular functions or stratification.

The above results show that a p38 MAP kinase inhibitor maintains corneal endothelial cell functions, pumping function and barrier function, and suppresses decrease in density.

Example 6

P38 MAP Kinase Inhibitor Suppresses Cytokine Production by Corneal Endothelial Cells The present Example confirms whether p38 MAP kinase signal inhibition suppresses cytokines produced by corneal endothelial cells.

Based on the aforementioned experimental methodology, a cytokine antibody array (Proteome Profiler, # ARY005, R&D Systems) blotted with 36 types of antibodies was used to find the expression pattern of cytokines in a human corneal endothelial culture solution.

Figure 7:
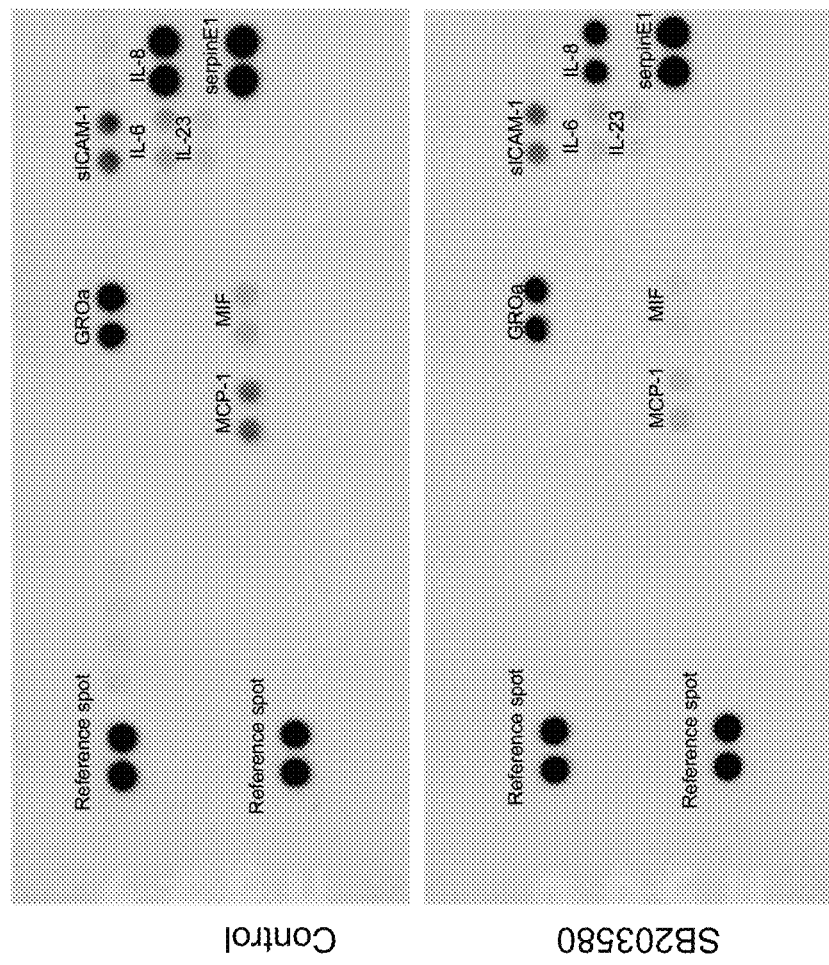
FIG. 7 are results showing that p38 MAP kinase signal inhibition suppresses cytokines produced by corneal endothelial cells. Reference Spot indicates a reference spot. GROa, sICAM-1, IL-6, IL-8, IL-23, MCP-1, MIF, and SerpinE1 show their respective marker spots. In the control (top row), GROa, sICAM-1, IL-6, IL-8, IL-23, MCP-1, MIF, and SerpinE1 were detected. Meanwhile, cytokines other than serpinE1 decreased relative to the control in a culture supernatant added with SB203580 (bottom row).
Figure 8:
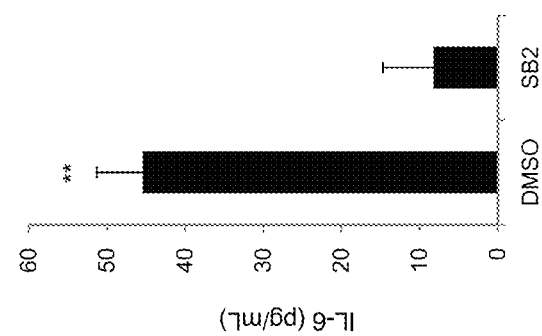
FIG. 8 shows that p38 MAP kinase signal inhibition suppresses IL-6 produced by corneal endothelial cells. It was demonstrated by PCR (left)) and ELISA (right)) that IL-6 production decreases when cultured by adding SB203580 relative to the control. In the left column, the left lane shows a control and the right lane shows SB203580. The top row shows IL-6 and the bottom row shows the control GAPDH. In the graph in the right section, the left shows the control DMSO and right shows SB203580. The y axis indicates the amount of IL-6 production (pg/mL).
Figure 8:
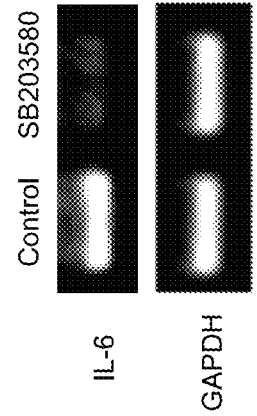

The results are shown in FIG. 7. As shown in FIG. 7, signals of GROa, sICAM-1, IL-6, IL-8, IL-23, MCP-1, MIF, and SerpinE1 were detected regardless of the presence of SB203580. Cytokines other than serpinE1 were decreased relative to vehicle in culture supernatant added with SB203580. This indicates suppression of cytokine production of corneal endothelial cells due to a culturing environment. Further, cellular senescence particularly has drawn attention in recent years for increasing production of cytokines such as IL-6, which is involved with senescence. Thus, whether to suppress IL-6 production was studied by PCR and ELISA. The results are shown in FIG. 8. PCR (left and ELISA (right) show that IL-6 production decreases relative to the control by adding SB203580 for culturing. The amount of expression of IL-6 of human corneal endothelial cells was quantified by ELISA (IL-6) and RT-PCR as described in the aforementioned experimental methods.

The above results show that a p38 MAP kinase inhibitor suppresses cytokine production by corneal endothelial cells.

Example 6

Study of Effect of p38 MAP Kinase Inhibitor on Cell Death

The present Example studied whether a p38 MAP kinase inhibitor suppresses death of corneal endothelial cells.

In order to study the effect of a p38 MAP kinase signal inhibition on cell death, cultured human corneal endothelial cells were stimulated with ultraviolet rays (UV) of 100 $J/m^2$ to induce cell death to study the effect of SB203580 (used at 10 μM). The number of cells was counted for the study.

Figure 9:
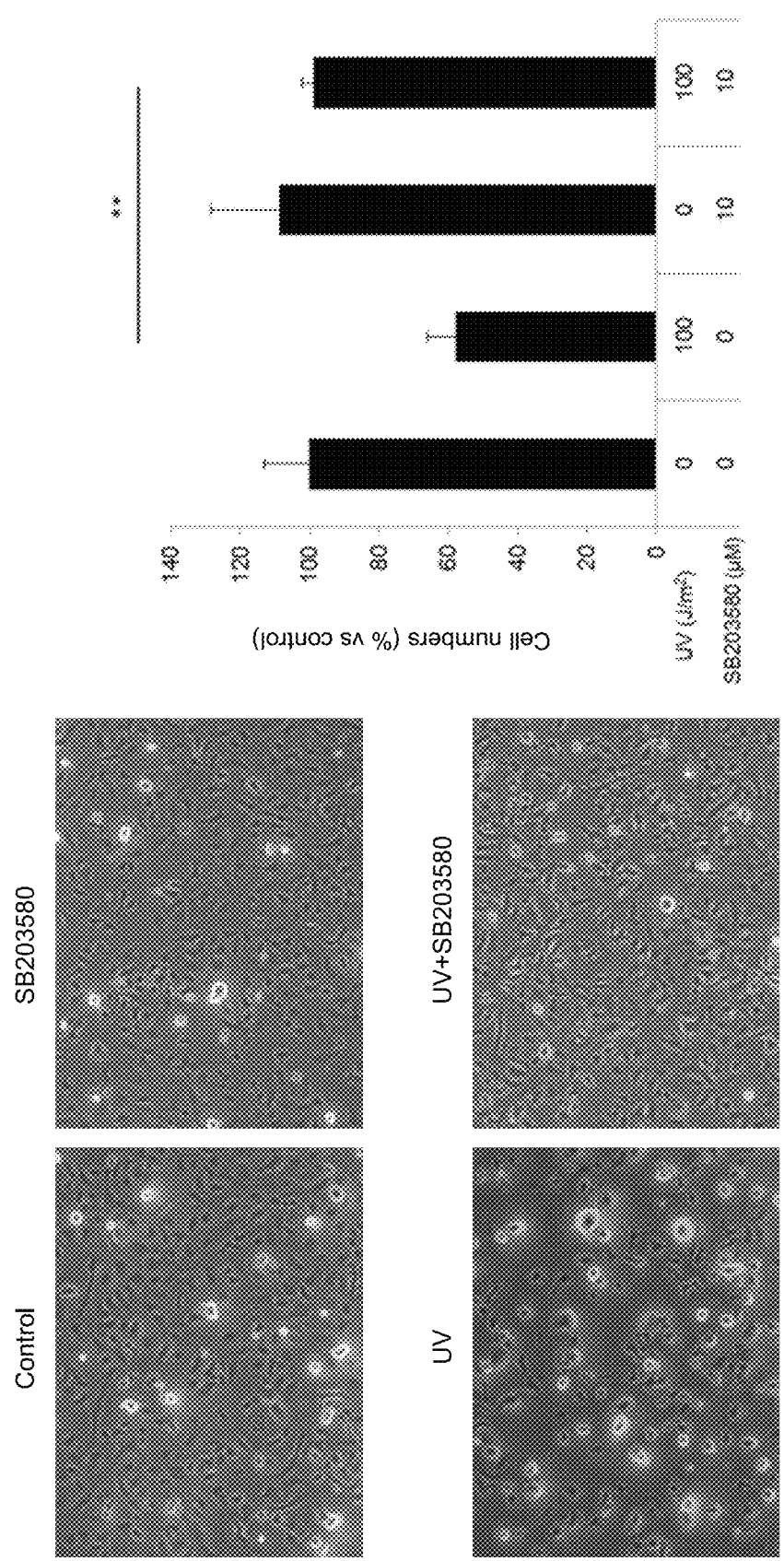
FIG. 9 shows that p38 MAP kinase signal inhibition suppresses corneal endothelial cell death. In the picture on the left side, top left shows the control and the top right shows SB203580, bottom left shows results of UV irradiation only and bottom right shows results of combining UV irradiation with SB203580. The graph on the left side shows results of each shown treatment with UV irradiation and SB203580. The y axis indicates the number of cells (% with respect to the control). ** indicates statistical significance at p<0.05. In order to study the effect of p38 MAP kinase signal inhibition on cell death, cultured human corneal endothelial cells were stimulated with 100 J/m$^2$ ultraviolet rays (UV) to induce cell death to study the effect of SB203580. The pictures from a phase difference microscope (left) are from 9 hours after UV irradiation. The right side is a graph depicting the percentage of live cell count to the control 12 hours after UV irradiation. The live cell count decreases due to UV irradiation, but significantly increases due to SB203580. It is understood therefrom that cellular disorders and cell death of corneal endothelial cells are suppressed by p38 MAP kinase signal inhibition.

The results are shown in FIG. 9. The picture from a phase difference microscope (left) is from 12 hours after UV irradiation. The right side is a graph after 12 from UV irradiation described in terms of the percentage of live cells to control. The number of live cells decreases due to UV irradiation, but significantly increases due to SB203580. It is understood thereby that p38 MAP kinase signal inhibition suppresses a cellular disorder of corneal endothelial cells to suppress cell death.

Example 7

Study of Effect of p38 MAP Kinase Inhibitor on Apoptosis

The present Example studied whether p38 MAP kinase inhibition suppresses apoptosis of corneal endothelia upon UV stimulation. In accordance with the experimental methodology discussed above in the specification, Western blot was used to confirm whether activation due to cleavage of PARP and caspase 3, which are molecules executing apoptosis due to UV irradiation, is suppressed, and whether expression of phosphorylated histone H2AX induced by cleavage of DNA double strand due to UV irradiation is suppressed. The following antibodies were used in the Western blot: anti-caspase 3 antibodies (9662, Cell Signaling), anti-PARP antibodies (9542, Cell Signaling), anti-H2AX antibodies (05-636, Millipore), and anti-GAPDH antibodies (2118, Cell Signaling) under the following condition: 100 J/m$^2$. SB203580 was used as a p38 MAP kinase signal inhibitor and the concentration thereof was 10 μM.

Figure 10:
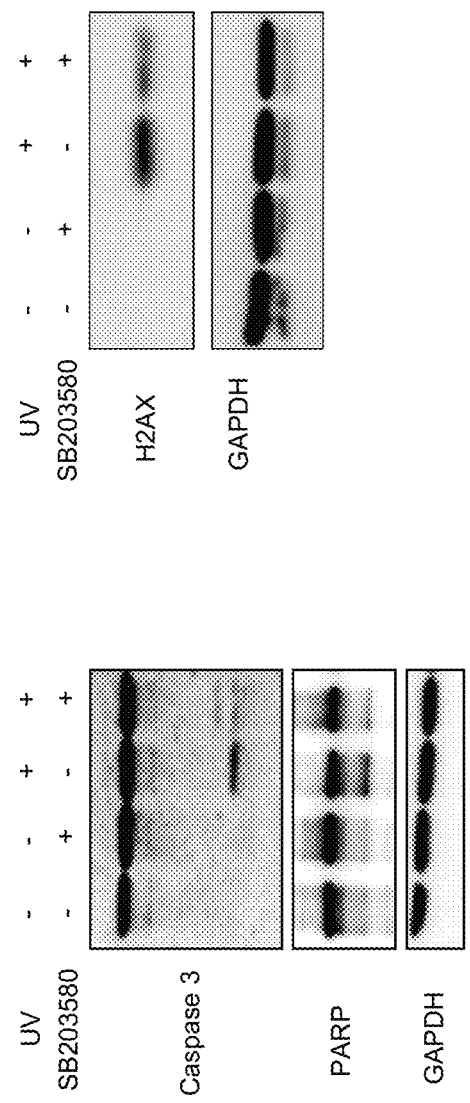
FIG. 10 shows that p38 MAP kinase signal inhibition suppresses apoptosis upon UV stimulation of a corneal endothelium. Both the left and right sides show results of Western blotting. Each lane shows the difference in the presence or absence of UV irradiation and SB203580. From the top panel, caspase 3, PARP, and GAPDH are shown. The right side also shows a difference in the presence or absence of UV irradiation and SB203580. From the top panel, H2AX and GAPDH are shown. The left side shows that activation due to cleavage of caspase 3 and PARP, which are molecules executing apoptosis due to UV irradiation, is suppressed by SB203580. The right side shows that expression of phosphorylated histone H2AX induced by cleavage of the double strand of a DNA due to UV irradiation is suppressed by SB203580.
Figure 11:
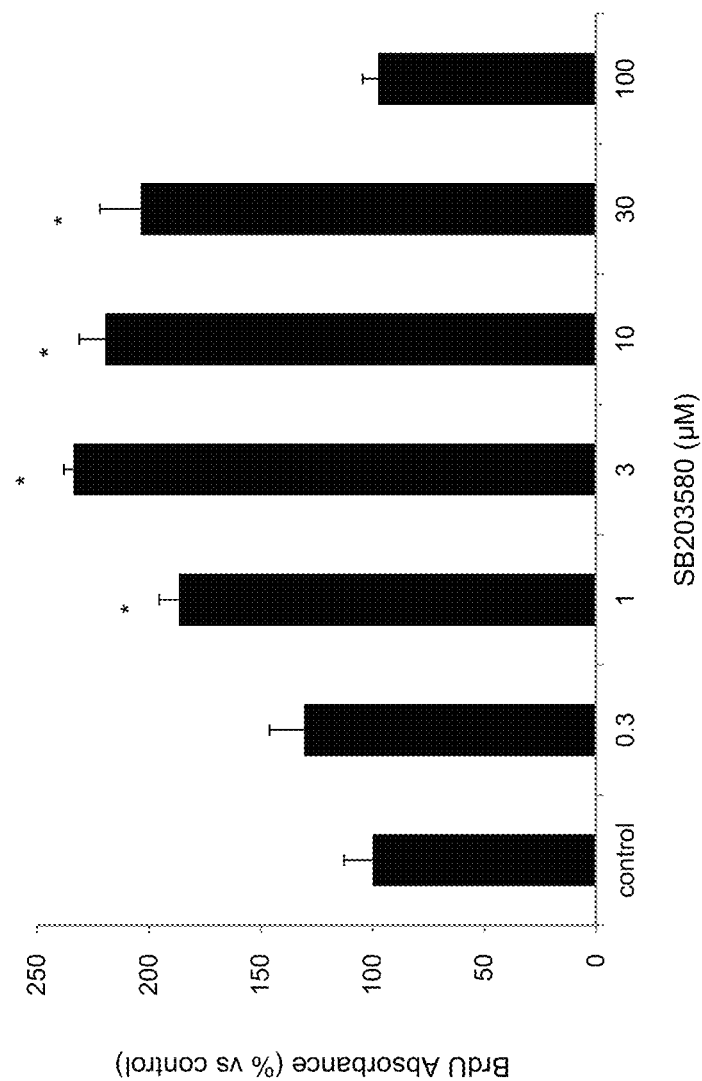
FIG. 11 shows that the p38 MAPK inhibitor SB203580 promotes proliferation of cultured corneal endothelial cells. BrdU uptake is shown as a percentage with respect to the control (y axis). The x axis indicates, from the left, the control (with no addition of SB203580), final concentration of 0.3 µM, 1 µM, 3 µM, 10 µM, 30 µM, and 100 µM. * indicates p<0.01.
Figure 12:
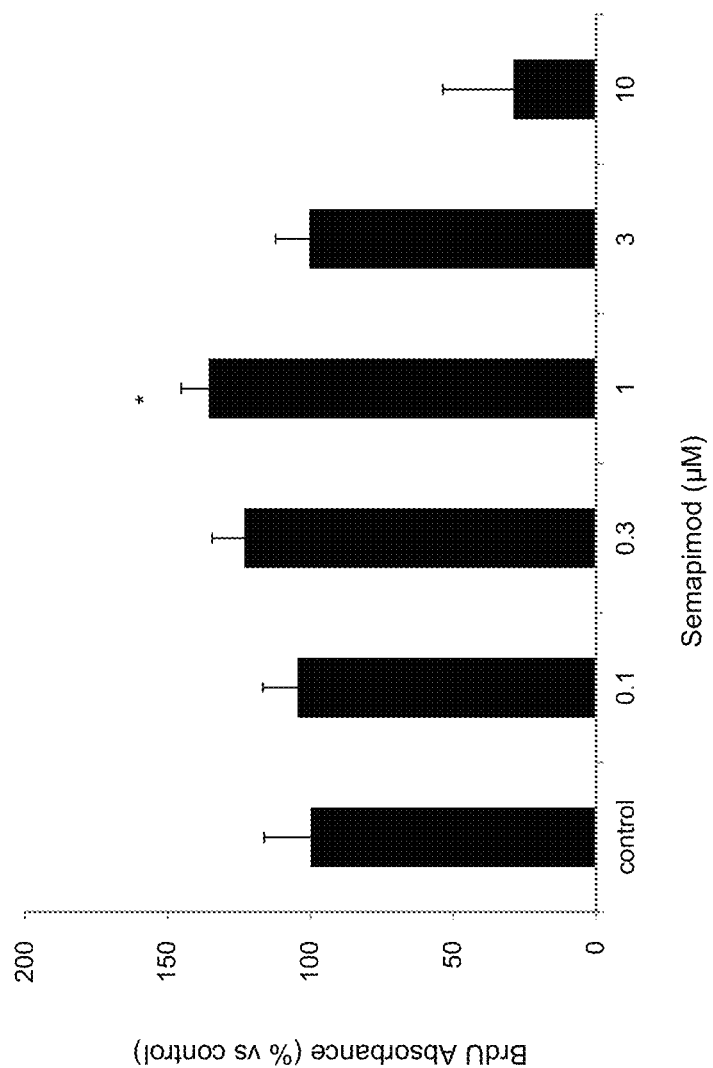
FIG. 12 shows that the p38 MAPK inhibitor Semapimod promotes proliferation of cultured corneal endothelial cells. BrdU uptake is shown as a percentage with respect to the control (y axis). The x axis indicates, from the left, the control (with no addition of Semapimod), final concentration of 0.1 µM, 0.3 µM, 1 µM, 3 µM, and 10 µM. * indicates p<0.01.
Figure 13:
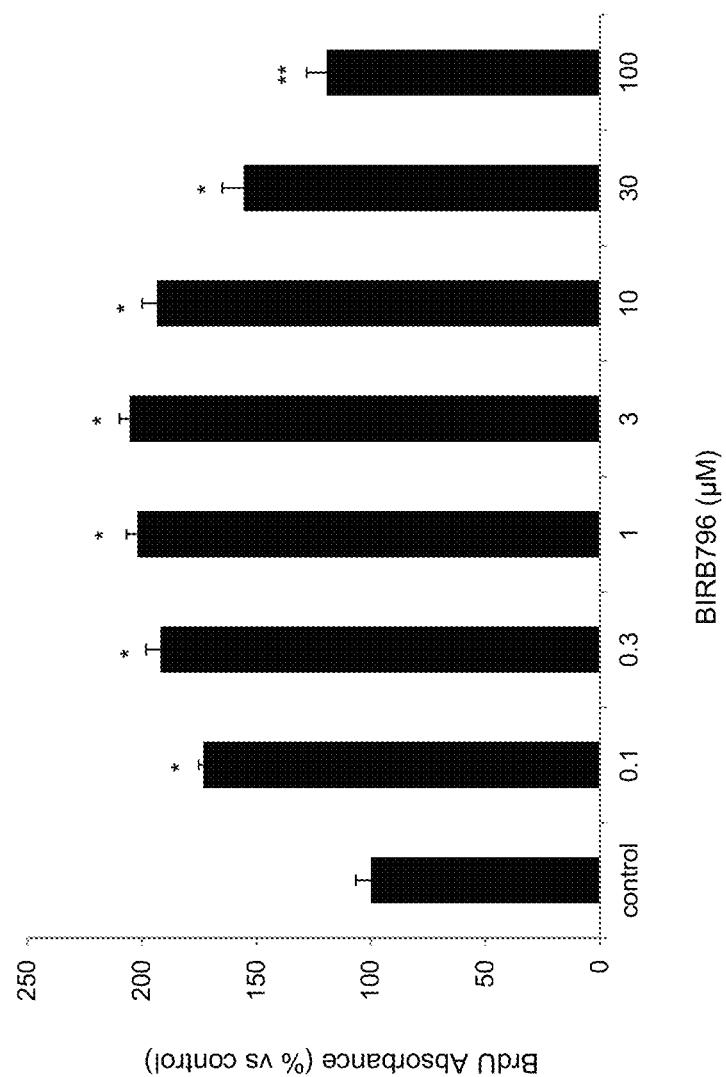
FIG. 13 shows that the p38 MAPK inhibitor BIRB796 promotes proliferation of cultured corneal endothelial cells. BrdU uptake is shown as a percentage with respect to the control (y axis). The x axis indicates, from the left, the control (with no addition of BIRB796), final concentration of 0.1 µM, 0.3 µM, 1 µM, 3 µM, 10 µM, 30 µM, and 100 µM. * indicates p<0.01.
Figure 14:
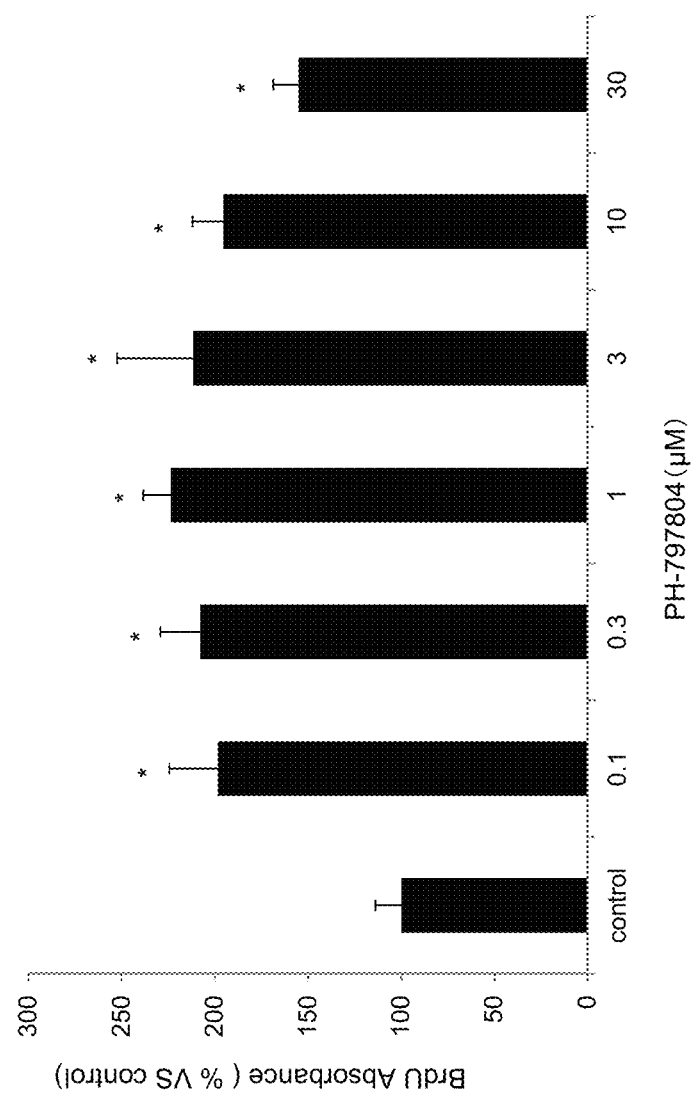
FIG. 14 shows that the p38 MAPK inhibitor PH-797804 promotes proliferation of cultured corneal endothelial cells. BrdU uptake is shown as a percentage with respect to the control (y axis). The x axis indicates, from the left, the control (with no addition of BIRB796), final concentration of 0.1 µM, 0.3 µM, 1 µM, 3 µM, 10 µM, and 30 µM. * indicates p<0.01.
Figure 15:
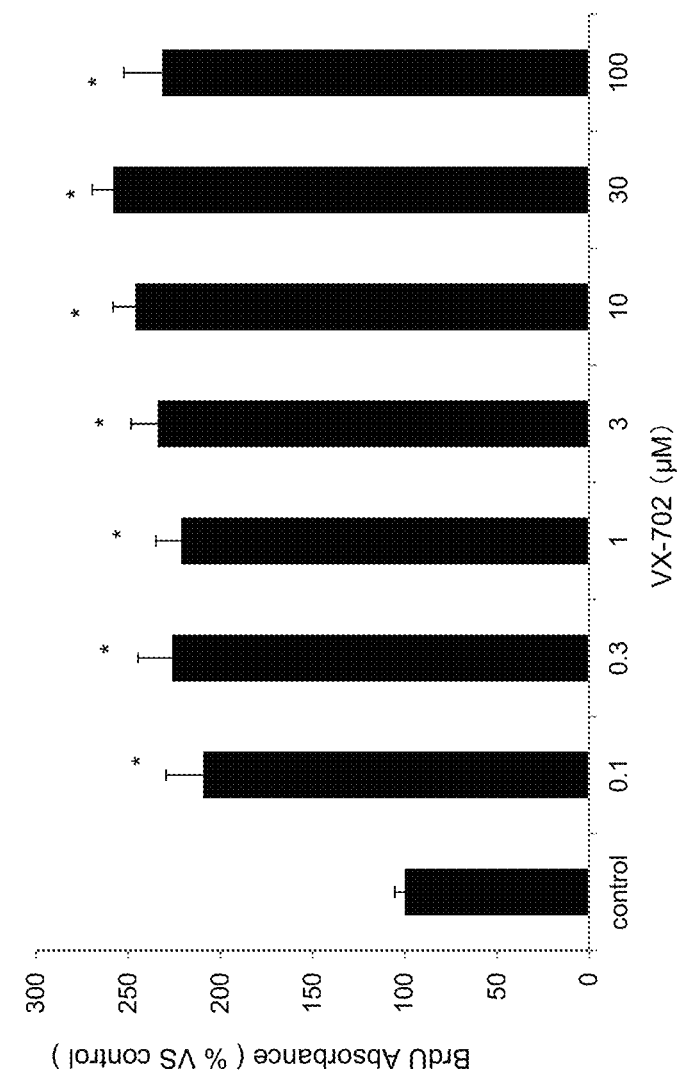
FIG. 15 shows that the p38 MAPK inhibitor VX-702 promotes proliferation of cultured corneal endothelial cells. BrdU uptake is shown as a percentage with respect to the control (y axis). The x axis indicates, from the left, the control (with no addition of BIRB796), final concentration of 0.1 µM, 0.3 µM, 1 µM, 3 µM, 10 µM, 30 µM, and 100 µM. * indicates p<0.01.
Figure 16:
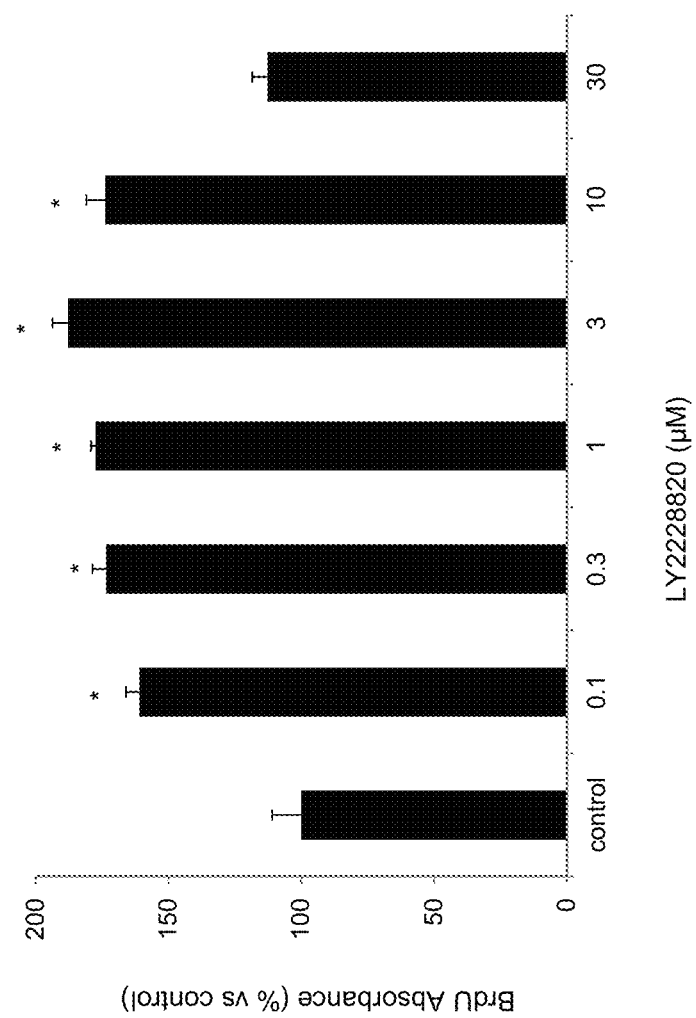
FIG. 16 shows that the p38 MAPK inhibitor LY2228820 promotes proliferation of cultured corneal endothelial cells. BrdU uptake is shown as a percentage with respect to the control (y axis). The x axis indicates, from the left, the control (with no addition of BIRB796), final concentration of 0.1 µM, 0.3 µM, 1 µM, 3 µM, 10 µM, and 30 µM. * indicates p<0.01.
Figure 17:
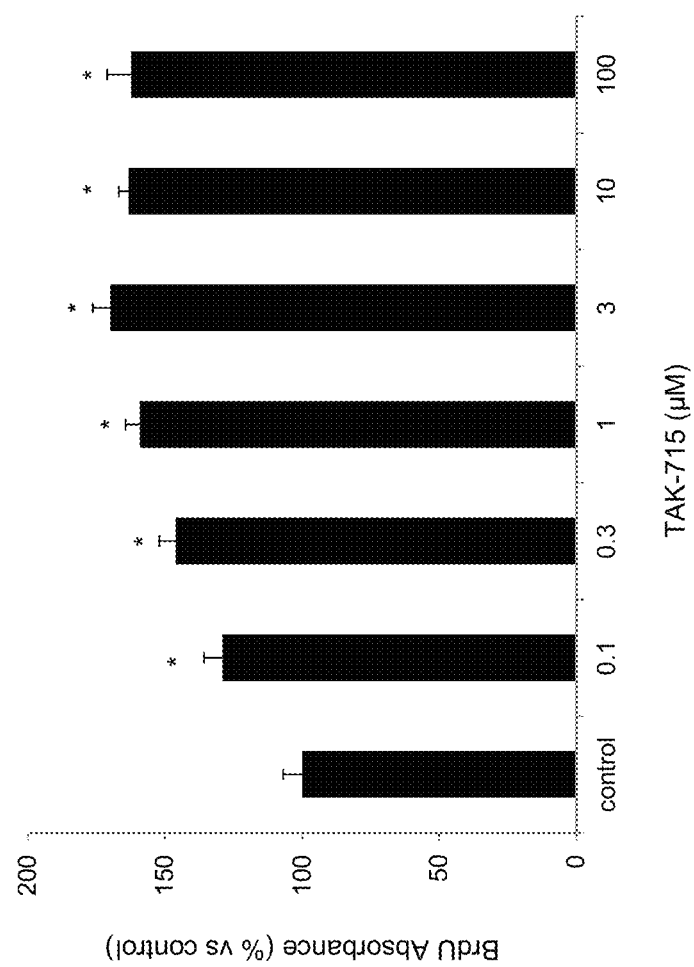
FIG. 17 shows that the p38 MAPK inhibitor TAK-715 promotes proliferation of cultured corneal endothelial cells. BrdU uptake is shown as a percentage with respect to the control (y axis). The x axis indicates, from the left, the control (with no addition of BIRB796), final concentration of 0.1 µM, 0.3 µM, 1 µM, 3 µM, 10 µM, 30 µM, and 100 µM. * indicates p<0.01.
Figure 18:
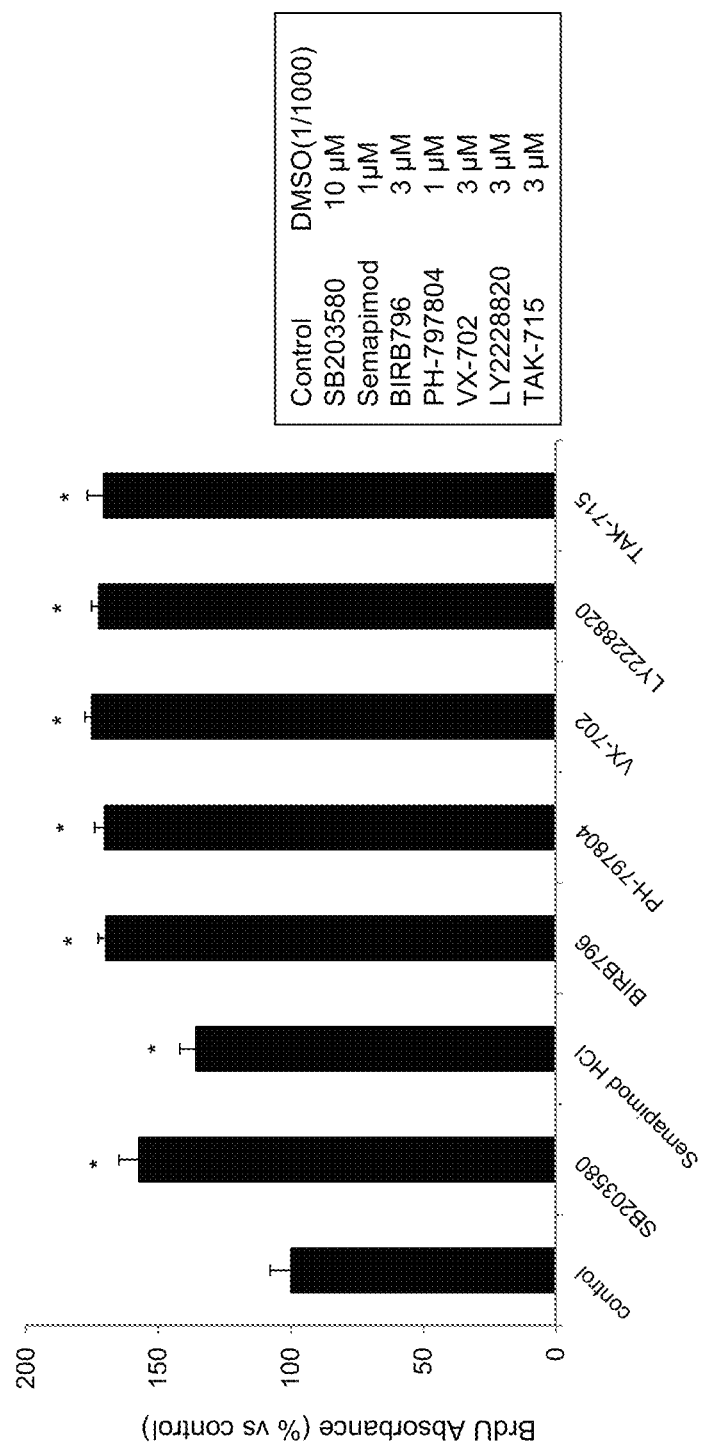
FIG. 18 shows that a p38 MAPK inhibitor promotes proliferation of cultured monkey corneal endothelial cells. BrdU uptake is shown as a percentage with respect to the control (y axis) The x axis indicates, from the left, the control (DMSO 1/1000, no agent added), 10 µM of SB203580, 1 µM of Semapimod, 3 µM of BIRB796, 1 µM of PH-797804, 3 µM of VX-702, 3 µM of LY2228820, and 3 µM of TAK-715. * indicates p<0.01.
Figure 19:
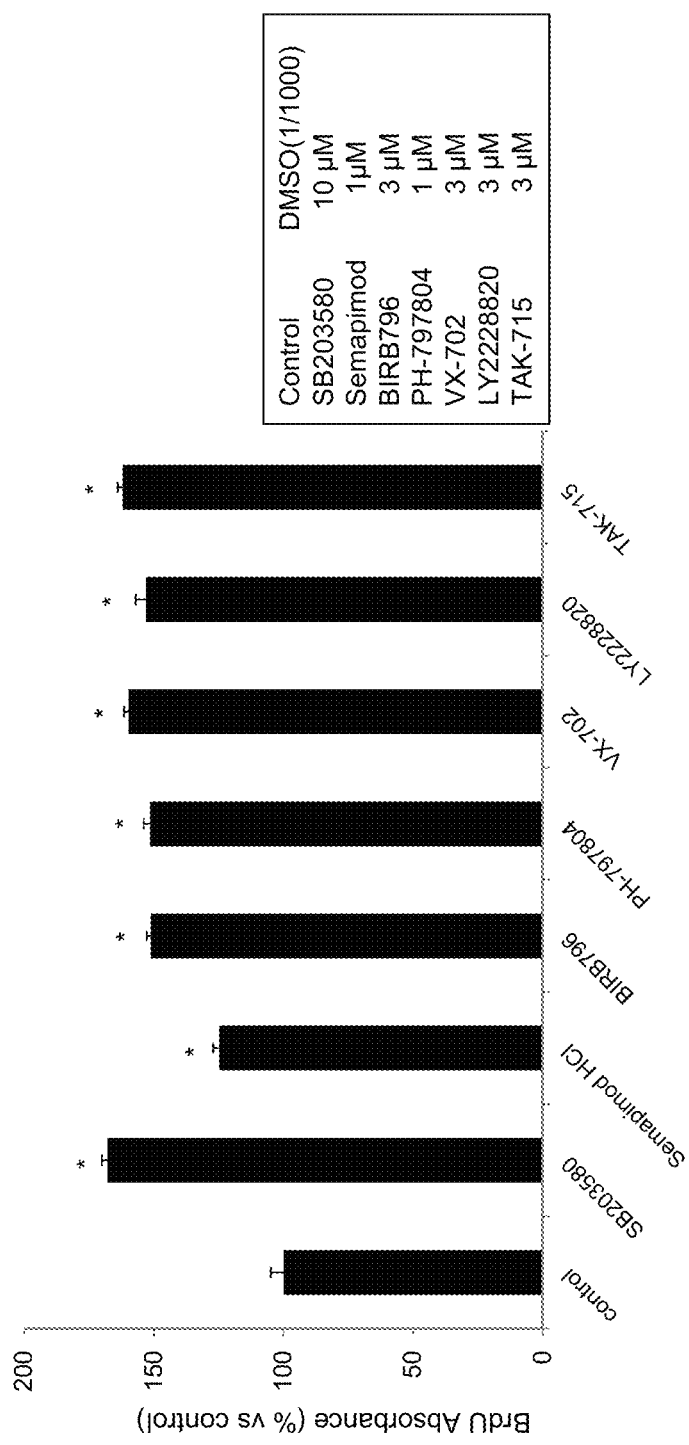
FIG. 19 shows that a p38 MAPK inhibitor promotes proliferation of cultured human corneal endothelial cells. BrdU uptake is shown as a percentage with respect to the control (y axis). The x axis indicates, from the left, the control (DMSO 1/1000, no agent added), 10 µM of SB203580, 1 µM of Semapimod, 3 µM of BIRB796, 1 µM of PH-797804, 3 µM of VX-702, 3 µM of LY2228820, and 3 µM of TAK-715. * indicates p<0.01.

The results are shown in FIG. 10. The left side shows that SB203580 suppresses activation by cleavage of PARP and caspase 3, which are molecules executing apoptosis due to UV irradiation. The right side shows the SB203580 suppresses phosphorylated histone H2AX induced by cleavage of double stand of a DNA due to UV irradiation. The above results show that p38 MAP kinase inhibition suppresses apoptosis of corneal endothelial cells.

In view of the above-described Examples, p38 MAP kinase inhibition promotes corneal endothelial cell proliferation, suppresses cell senescence, and suppresses cell death. Thus, it is demonstrated to be a target for therapy and prevention of progression of corneal endothelial disorders. For instance, eye drops, anterior chamber administration, subconjunctival injection, systemic administration and the like of the p38 MAP kinase inhibitor used in the present study or the like can potentially be developed as a therapeutic drug.

Example 8

Promotion of Proliferation with Various p38 MAPK Inhibitors

The present Example demonstrates the promotion of proliferation with various P38 MAPK inhibitors, and the effect of the present invention is not limited to a specific p38 MAPK inhibitor, but is observed in all p38 MAPK inhibitors. The present Example used reagents that are each considered as having inhibitory action specific to p38 MAPK to demonstrate that the effect of the present invention is not due to inhibition of other kinases, but is due to inhibition of p38 MAPK.

(Reagents)

The following agents were used.
(1) SB203580 (4-(4-fluorophenyl)-2-(4-methylsulfinylphenyl)-5-(4-pyridyl)-1H-imidazole) (Cayman, catalog number: 13067): SB203580 is known to be a specific (selective) inhibitor of MAPK (Biochem Biophys Res Commun. 1999 Oct. 5; 263(3): 825-31.) Thus, the experimental results with SB203580 can be identified as a result due to MAPK inhibition.
(2) Semapimod (N,N'-bis[3,5-bis[1-[2-(aminoiminomethyl)hydrazono]ethyl]phenyl]decanediamide) (CNI-1493; Med-Koo Biosciences, catalog number: 202590): Semapimod is known as an excellent inhibitor of MAPK (Gastroenterology. 2002 January; 122(1): 7-14; Transplant Proc. 1998 March; 30(2): 409-10; Auton Neurosci. 2000 Dec. 20; 85(1-3): 141-7; Gastroenterology. 2009 February; 136(2): 619-29. doi: 10.1053/j.gastro.2008.10.017. Epub 2008 Oct. 9.).
(3) BIRB796 (Doramapimod; N-[3-tert-butyl-1-(4-methylphenyl) pyrazole-5-yl]-N'-[4-(2-morpholinoethoxy)-1-naphthyl]urea) (Selleck Chemicals, catalog number: S1574): BIRB796 is known to be a specific (selective) inhibitor of MAPK (Nat Struct Biol. 2002 April; 9(4): 268-72.). Thus, the experimental results with BIRB796 can be identified as a result due to MAPK inhibition.
(4) PH-797804 (3-(3-bromo-4-((2,4-difluorobenzyl)oxy)-6-methyl-2-oxopyridine-1(2H)-yl)-N,4-dimethylbenzamide) (Selleck Chemicals, catalog number: S2726): PH-797804 is known as a specific (selective) inhibitor of MAPK (Bioorg Med Chem Lett. 2011 Jul. 1; 21(13): 4066-71. doi: 10.1016/j.bmcl.2011.04.121. Epub 2011 May 11.). Thus, experimental results with PH-797804 can be identified as a result due to MAPK inhibition.
(5) VX-702 (1-(carbamoyl-6-(2,4-difluorophenyl)pyridine-2-yl)-1-(2,6-difluorophenyl)urea) (Selleck Chemicals, catalog number: S6005): VX-702 is known as a specific (selective) inhibitor of MAPK (Curr Opin Investig Drugs. 2006 November; 7(11): 1020-5.) Thus, experimental results with VX-702 can be identified as a result due to MAPK inhibition.
(6) LY2228820 (ralimetinib; 5-(2-(tert-butyl)-5-(4-fluorophenyl)-1H-imidazole-4-yl)-3-neopentyl-3H-imidazo[4,5-b]pyridine-2-amine) (Selleck Chemicals, catalog number: S1494): LY2228820 is known as a potent specific (selective) inhibitor of MAPK (Br J Haematol. 2008 May; 141(5): 598-606. doi: 10.1111/j.1365-2141.2008.07044.x.Epub 2008 Apr. 7; Mol Cancer Ther. 2014 February; 13(2): 364-74. doi: 10.1158/1535-7163.MCT-13-0513.Epub 2013 Dec. 19; Biol Chem. 2013 Mar. 1; 288(9): 6743-53.doi: 10.1074/jbc.M112.425553.Epub 2013 Jan. 18.) Thus, experimental results with LY2228820 can be identified as a result due to MAPK inhibition.
(7) TAK-715 (2-benzamide-4-[2-ethyl-4-(3-methylphenyl)thiazole-5-yl]pyridine) (Selleck Chemicals, catalog number: S2928): TAK-715 is known as a potent specific (selective) inhibitor of MAPK (J Med Chem. 2005 Sep. 22; 48(19): 5966-79.) Thus, experimental results with TAK-715 can be identified as a result due to MAPK inhibition.

(1) SB203580 (4-(4-fluorophenyl)-2-(4-methylsulfinylphenyl)-5-(4-pyridyl)-1H-imidazole)

The medium was removed from a culture dish culturing cynomolgus monkey corneal endothelial cells (NISSEI BILIS). A phosphate buffer solution (Nacalai Tesque, 14249-95) heated to 37° C. in advance was added thereto and the cells were washed. This operation was repeated twice. After removing the phosphate buffer solution, 0.05% Trypsin-EDTA (Nacalai Tesque, 35554-64) was added and the cells were incubated for 10 minutes at 37° C. (5% CO$_2$). The cells were then suspended in DMEM (Nacalai Tesque, 08456-94)+10% FBS (Biowest, S1820-500)+1% penicillin/streptomycin (P/S, Nacalai Tesque, 26252-94) and centrifuged for 3 minutes at 1200 rpm to collect the cells.

A 96-well plate was treated with an FNC coating mix (50 ml (AES-0407), ATHENA, catalog number: 0407). The monkey corneal endothelial cells (lot: 20120404-3L-P8) were seeded in the coated 96-well plate at a ratio of 5000 cells/well. The cells were cultured for 30 hours at 37° C. (5% CO$_2$). After 30 hours, the medium was removed and changed to a serum free medium: DMEM+1% P/S to culture the cells for 18 hours. After 18 hours, SB203580 (Cayman, catalog number: 13067) was added to a DMEM+10% FBS+1% P/S medium such that the final concentration dissolved with DMSO was 0.3, 1, 3, 10, 30, or 100 μmol/l, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. SB203580 was added such that the final concentrations were 0.3, 1, 3, 10, 30, or 100 μmol/l, and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured. *P<0.01, Dunnet's test, n=5.

(2) Semapimod (N,N'-bis[3,5-bis[1-[2-(aminoiminomethyl) hydrazono]ethyl]phenyl]decanediamide)

As in (1), the medium was removed from a culture dish culturing cynomolgus monkey corneal endothelial cells. A phosphate buffer solution heated to 37° C. in advance was added thereto and the cells were washed. This operation was repeated twice. After removing the phosphate buffer solution, 0.05% Trypsin-EDTA (Nacalai Tesque, 35554-64) was added and the cells were incubated for 10 minutes at 37° C. (5% $CO_2$). The cells were then suspended in DMEM (Nacalai Tesque, 08456-94)+10% FBS (Biowest, S1820-500)+1% penicillin/streptomycin (Nacalai Tesque, catalog number: 26252-94) and centrifuged for 3 minutes at 1200 rpm to collect the cells.

A 96-well plate was treated with an FNC coating mix (50 ml (AES-0407), ATHENA, catalog number: 0407). Monkey corneal endothelial cells (lot: 20120404-3L-P8) were seeded in the coated 96-well plate at a ratio of 5000 cells/well. The cells were cultured for 30 hours at 37° C. (5% $CO_2$). After 30 hours, the medium was removed and changed to a serum free medium: DMEM+1% P/S to culture the cells for 18 hours. After 18 hours, Semapimod HCl (MedKoo Biosciences, catalog number: 202590, lot number: SMC20120918) was added to the DMEM+10% FBS+1% P/S medium such that the final concentration dissolved with DMSO was 0.1, 0.3, 1, 3, or 10 μmol/l, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. Semapimod HCl was added such that the final concentration was 0.1, 0.3, 1, 3, or 10 μmol/l and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

(3) BIRB796 (Doramapimod; N-[3-tert-butyl-1-(4-methylphenyl) pyrazole-5-yl]-N'-[4-(2-morpholinoethoxy)-1-naphthyl]urea)

As in (1), the medium was removed from a culture dish culturing cynomolgus monkey corneal endothelial cells. PBS (−) heated to 37° C. in advance was added thereto and the cells were washed. This operation was repeated twice. After removing the PBS (−), 0.05% Trypsin-EDTA (Nacalai Tesque, 35554-64) was added and the cells were incubated for 10 minutes at 37° C. (5% $CO_2$). The cells were then suspended in DMEM (Nacalai Tesque, 08456-94)+10% FBS (Biowest, S1820-500)+1% penicillin/streptomycin (Nacalai Tesque, catalog number: 26252-94) and centrifuged for 3 minutes at 1200 rpm to collect the cells.

A 96-well plate was treated with an FNC coating mix (50 ml (AES-0407), ATHENA, catalog number: 0407). The monkey corneal endothelial cells (lot: 20120404-3L-P9) were seeded in the coated 96-well plate at a ratio of 5000 cells/well. The cells were cultured for 30 hours at 37° C. (5% $CO_2$). After 30 hours, the medium was removed and changed to a serum free medium: DMEM+1% P/S to culture the cells for 18 hours. After 18 hours, BIRD796 (Doramapimod) (Selleck Chemicals, catalog number: S1574, lot number: S157402) was added to the DMEM+10% FBS+1% P/S medium such that the final concentration dissolved with DMSO is 0.1, 0.3, 1, 3, 10, 30, or 100 μmol/l, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. BIRB796 (Doramapimod) was added such that the final concentration was 0.1, 0.3, 1, 3, 10, 30, or 100 μmol/l and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

(4) PH-797804 (3-(3-bromo-4-((2,4-difluorobenzyl)oxy)-6-methyl-2-oxopyridine-1 (2H)-yl)-N, 4-dimethylbenzamide)

As in (1), the medium was removed from a culture dish culturing cynomolgus monkey corneal endothelial cells. PBS(−) heated to 37° C. in advance was added thereto and the cells were washed. This operation was repeated twice. After removing PBS(−), 0.05% Trypsin-EDTA (Nacalai Tesque, 35554-64) was added and the cells were incubated for 10 minutes at 37° C. (5% $CO_2$). The cells were then suspended in DMEM (Nacalai Tesque, 08456-94)+10% FBS (Biowest, S1820-500)+1% penicillin/streptomycin (Nacalai Tesque, catalog number: 26252-94) and centrifuged for 3 minutes at 1200 rpm to collect the cells.

A 96-well plate was treated with an FNC coating mix (50 ml (AES-0407), ATHENA, catalog number: 0407). The monkey corneal endothelial cells (lot: 20120404-3L-P9) were seeded in the coated 96-well plate at a ratio of 5000 cells/well. The cells were cultured for 30 hours at 37° C. (5% $CO_2$). After 30 hours, the medium was removed and changed to a serum free medium: DMEM+1% P/S to culture the cells for 18 hours. After 18 hours, PH-797804 (Selleck Chemicals, catalog number: S2726, lot number: 01) was added to the DMEM+10% FBS+1% P/S medium such that the final concentration dissolved with DMSO was 0.1, 0.3, 1, 3, 10, or 30 mol/l, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. PH-797804 was added such that the final concentration was 0.1, 0.3, 1, 3, 10, or 30 μmol/l and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

(5) VX-702 (1-(carbamoyl-6-(2,4-difluorophenyl) pyridine-2-yl)-1-(2,6-difluorophenyl)urea) (2-(2,4-difluorophenyl)-6-(1-(2,6-difluorophenyl)ureido) nicotinamide)

As in (1), the medium was removed from a culture dish culturing cynomolgus monkey corneal endothelial cells. PBS(−) heated to 37° C. in advance was added thereto and the cells were washed. This operation was repeated twice. After removing PBS(−), 0.05% Trypsin-EDTA (Nacalai Tesque, 35554-64) was added and the cells were incubated for 10 minutes at 37° C. (5% $CO_2$). The cells were then suspended in DMEM (Nacalai Tesque, 08456-94)+10% FBS (Biowest, S1820-500)+1% penicillin/streptomycin (Nacalai Tesque, catalog number: 26252-94) and centrifuged for 3 minutes at 1200 rpm to collect the cells.

A 96-well plate was treated with an FNC coating mix (50 ml (AES-0407), ATHENA, catalog number: 0407). The monkey corneal endothelial cells (lot: 20120404-3L-P9) were seeded in the coated 96-well plate at a ratio of 5000 cells/well. The cells were cultured for 30 hours at 37° C. (5% $CO_2$). After 30 hours, the medium was removed and changed to a serum free medium: DMEM+1% P/S to culture the cells for 18 hours. After 18 hours, VX-702 (Selleck Chemicals, catalog number: S6005, lot number: 02) was added to the DMEM+10% FBS+1% P/S medium such that the final concentration dissolved with DMSO was 0.1, 0.3, 1, 3, 10, 30, or 100 µmol/l, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. VX-702 was added such that the final concentration was 0.1, 0.3, 1, 3, 10, 30, or 100 µmol/l and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

(6) LY2228820 (ralimetinib; 5-(2-(tert-butyl)-5-(4-fluorophenyl)-1H-imidazole-4-yl)-3-neopentyl-3H-imidazo [4,5-b]pyridine-2-amine)

As in (1), the medium was removed from a culture dish culturing cynomolgus monkey corneal endothelial cells. PBS(−) heated to 37° C. in advance was added thereto and the cells were washed. This operation was repeated twice. After removing PBS(−), 0.05% Trypsin-EDTA (Nacalai Tesque, 35554-64) was added and the cells were incubated for 10 minutes at 37° C. (5% $CO_2$) The cells were then suspended in DMEM (Nacalai Tesque, 08456-94)+10% FBS (Biowest, S1820-500)+1% penicillin/streptomycin (Nacalai Tesque, catalog number: 26252-94) and centrifuged for 3 minutes at 1200 rpm to collect the cells.

A 96-well plate was treated with an FNC coating mix (50 ml (AES-0407), ATHENA, catalog number: 0407). The monkey corneal endothelial cells (lot: 20120404-3L-P9) were seeded in the coated 96-well plate at a ratio of 5000 cells/well. The cells were cultured for 30 hours at 37° C. (5% $CO_2$). After 30 hours, the medium was removed and changed to a serum free medium: DMEM+1% P/S to culture the cells for 18 hours. After 18 hours, LY2228820 (Selleck Chemicals, catalog number: S1494, lot number: 01) was added to the DMEM+10% FBS+1% P/S medium such that the final concentration dissolved with DMSO was 0.1, 0.3, 1, 3, 10, or 30 µmol/l, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FES+1% P/S medium. LY2228820 was added such that the final concentration was 0.1, 0.3, 1, 3, 10, or 30 mol/l and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

(7) TAK-715 (2-benzamide-4-[2-ethyl-4-(3-methylphenyl) thiazole-5-yl]pyridine)

As in (1), the medium was removed from a culture dish culturing cynomolgus monkey corneal endothelial cells. PBS(−) heated to 37° C. in advance was added thereto and the cells were washed. This operation was repeated twice. After removing PBS(−), 0.05% Trypsin-EDTA (Nacalai Tesque, 35554-64) was added and the cells were incubated for 10 minutes at 37° C. (5% $CO_2$). The cells were then suspended in DMEM (Nacalai Tesque 08456-94)+10% FBS (Biowest, S1820-500)+1% penicillin/streptomycin (Nacalai Tesque, catalog number: 26252-94) and centrifuged for 3 minutes at 1200 rpm to collect the cells.

A 96-well plate was treated with an FNC coating mix (50 ml (AES-0407), ATHENA, catalog number: 0407). The monkey corneal endothelial cells (lot: 20120404-3L-P9) were seeded in the coated 96-well plate at a ratio of 5000 cells/well. The cells were cultured for 30 hours at 37° C. (5% $CO_2$). After 30 hours, the medium was removed and changed to a serum free medium: DMEM+1% P/S to culture the cells for 18 hours. After 18 hours, TAK-715 (Selleck Chemicals, catalog number: S2928, lot number: 01) was added to the DMEM+10% FBS+1% P/S medium such that the final concentration dissolved with DMSO was 0.1, 0.3, 1, 3, 10, or 100 µmol/l, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. TAK-715 was added such that the final concentration was 0.1, 0.3, 1, 3, 10, or 100 µmol/l and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

Example 9

Effect in Various Animal Species

The present Example demonstrated that proliferation is found to be promoted with various p38 MAPK inhibitors in not only monkeys but also humans. In addition, the effect of the present invention is demonstrated to be an effect observed in a wide-range of animal species including humans, instead of being limited to a specific animal species. The reagent used in Example 8 was used in each of the present Examples.

(1) Monkeys

The medium was removed from a culture dish culturing cynomolgus monkey corneal endothelial cells. PBS (−) heated to 37° C. in advance was added thereto and the cells were washed. This operation was repeated twice. After removing the PBS (−), 0.05% Trypsin-EDTA (Nacalai-Tesque, 35554-64) was added and the cells were incubated for 10 minutes at 37° C. (5% $CO_2$). The cells were then suspended in DMEM (Nacalai Tesque, 08456-94)+10% FBS (Biowest, S1820-500)+1% penicillin/streptomycin (Nacalai Tesque, catalog number: 26252-94) and centrifuged for 3 minutes at 1200 rpm to collect the cells.

A 96-well plate was treated with an FNC coating mix (50 ml (AES-0407), ATHENA, catalog number: 0407). The monkey corneal endothelial cells (lot: 20120404-3L-P9) were seeded in the coated 96-well plate at a ratio of 3000 cells/well. The cells were cultured for 30 hours at 37° C. (5% $CO_2$). After 30 hours, the medium was removed and changed to a serum free medium: DMEM+1% P/S to culture the cells for 18 hours. After 18 hours, SB203580 (Cayman, catalog number: 13067), Semapimod HCl (MedKoo Biosciences, catalog number: 202590, lot number: SMC20120918), BIRB796 (Doramapimod) (Selleck Chemicals, catalog number: S1574, lot number: S157402), PH-797804 (Selleck Chemicals, catalog number: S2726, lot number: 01), VX-702 (Selleck Chemicals, catalog number: S6005, lot number: 02), LY2228820 (Selleck Chemicals, catalog number: S1494, lot number: 01), and TAK-715 (Selleck Chemical, catalog number: S2928, lot number: 01) were added to the DMEM+10% FBS+1% P/S medium such that the final concentrations dissolved with DMSO were 10 μmol/l, 1 μmol/l, 3 μmol/l, 1 μmol/l, 3 μmol/l, 3 μmol/l, 3 μmol/l, and 3 μmol/l, respectively, and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. SB203580, SemapimodHCl, BIRB796, PH-797804, VX-702, LY2228820, and TAK-715 were added such that the final concentrations were 10 μmol/l, 1 μmol/l, 3 μmol/l, 1 μmol/l, 3 μmol/l, 3 μmol/l, and 3 μmol/l, respectively, and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

(2) Humans

The medium was removed from a culture dish culturing human corneal endothelial cells. PBS (−) heated to 37° C. in advance was added thereto and the cells were washed. This operation was repeated twice. After removing the PBS (−) TrypLE Select (×10) (GIBCO, A12177-01) was added and the cells were incubated for 10 minutes at 37° C. (5% $CO_2$). The cells were then suspended in Opti-MEM (GIBCO, 31985-070) and centrifuged for 3 minutes at 1200 rpm to collect the cells.

A 96-well plate was treated with an FNC coating mix (50 ml (AES-0407), ATHENA, catalog number: 0407). The human corneal endothelial cells (lot: C1642-P8) were seeded in a Condition Medium for humans in the coated 96-well plate at a ratio of 3000 cells/well. The cells were cultured for 30 hours at 37° C. (5% $CO_2$). After 30 hours, the medium was removed and changed to a serum free medium: Opti-MEM+1% P/S to culture the cells for 18 hours. After 18 hours, SB203580 (Cayman, catalog number: 13067), Semapimod HCl (MedKoo Biosciences, catalog number: 202590, lot number: SMC20120918), BIRB796 (Doramapimod) (Selleck Chemicals, catalog number: S1574, lot number: S157402), PH-797804 (Selleck Chemicals, catalog number: S2726, lot number: 01), VX-702 (Selleck Chemicals, catalog number: S6005, lot number: 02), LY2228820 (Selleck Chemicals, catalog number: S1494, lot number: 01), and TAK-715 (Selleck Chemical, catalog number: S2928, lot number: 01) were added to the Condition Medium for humans such that the final concentrations dissolved with DMSO are 10 μmol/l, 1 μmol/l, 3 μmol/l, 1 μmol/l, 3 μmol/l, 3 mol/l, and 3 μmol/l, respectively and the cells were cultured for 24 hours. DMSO was added to the control. After 24 hours, a BrdU labeling reagent (Amersham Cell Proliferation Biotrak ELISA System, Version 2, GE Healthcare, catalog number: RPN250) was further added at a ratio of 1:1000 to the DMEM+10% FBS+1% P/S medium. SB203580, Semapimod HCl, BIRB796, PH-797804, VX-702, LY2228820, and TAK-715 were added such that the final concentrations were 10 μmol/l, 1 μmol/l, 3 μmol/l, 1 μmol/l, 3 μmol/l, 3 μmol/l, and 3 μmol/l, respectively, and the cells were cultured for 24 hours. DMSO was added to the control. After 24 hours, BrdU ELISA was carried out with Amersham Cell Proliferation Biotrak ELISA System, Version 2 (GE Healthcare, catalog number: RPN250). The absorbance at 450 nm was measured.

Example 10: Activation of p38 MAPK Induces Apoptosis

The present Example demonstrated that activation of p38 MAPK induces apoptosis.

(Materials and Methods)

$1 \times 10^5$ cultured monkey corneal endothelial cells were seeded on a 12-well plate coated with an FNC Coating Mix and cultured for about 5 days until reaching confluence under the condition of 5% $CO_2$ at 37° C. The medium used was Dulbecco's Modified Eagle Medium (Gibco, 12320-032), 10% FBS, 1% Penicillin-Streptomycin (nacalai tesque, 26252-94).

As acclimation treatment, Z-VAD (OMe)-FMK (Wako Pure Chemical Industries, Ltd. 269-02071) was then added at a concentration of 10 μM and the cells were incubated for 16 hours under the condition of 5% $CO_2$ at 37° C. For the Control group and anisomysin group, a solvent of a reagent Dimethyl Sulfoxide (DMSO) (Dimethyl Sulfoxide, Sterile-filtered; nacalai tesque, 13408-64) was added. The medium used was Gibco DMEM, 1% P/S. The cellular supernatant was then removed, and anisomysin (Wako Pure Chemical Industries Ltd., 017-16861) was added to the anisomysin group and the anisomysin+Z-VAD-FMK group at a concentration of 10 μM. 10 μM of Z-VAD was added with anisomysin to the anisomysin+Z-VAD-FMK group. DMSO was added to the groups to which Z-VAD-FMK was not added. The cells were then cultured for 9 hours. The cellular form was observed under a phase difference microscope. A picture was taken after 9 hours.

After 9 hours, cell proteins were collected. The amount of protein expression was compared by Western blot. Anti-caspase 3 antibodies (cell signaling, 9662S), anti-p38 MAPK antibodies (cell signaling, #9212), and anti-pp38 MAPK antibodies (cell signaling, #4631S) were used as the antibodies. Further, anti-GAPDH antibodies (MBL, 3H12) were used as the internal standard.

(Results)

Figure 20:
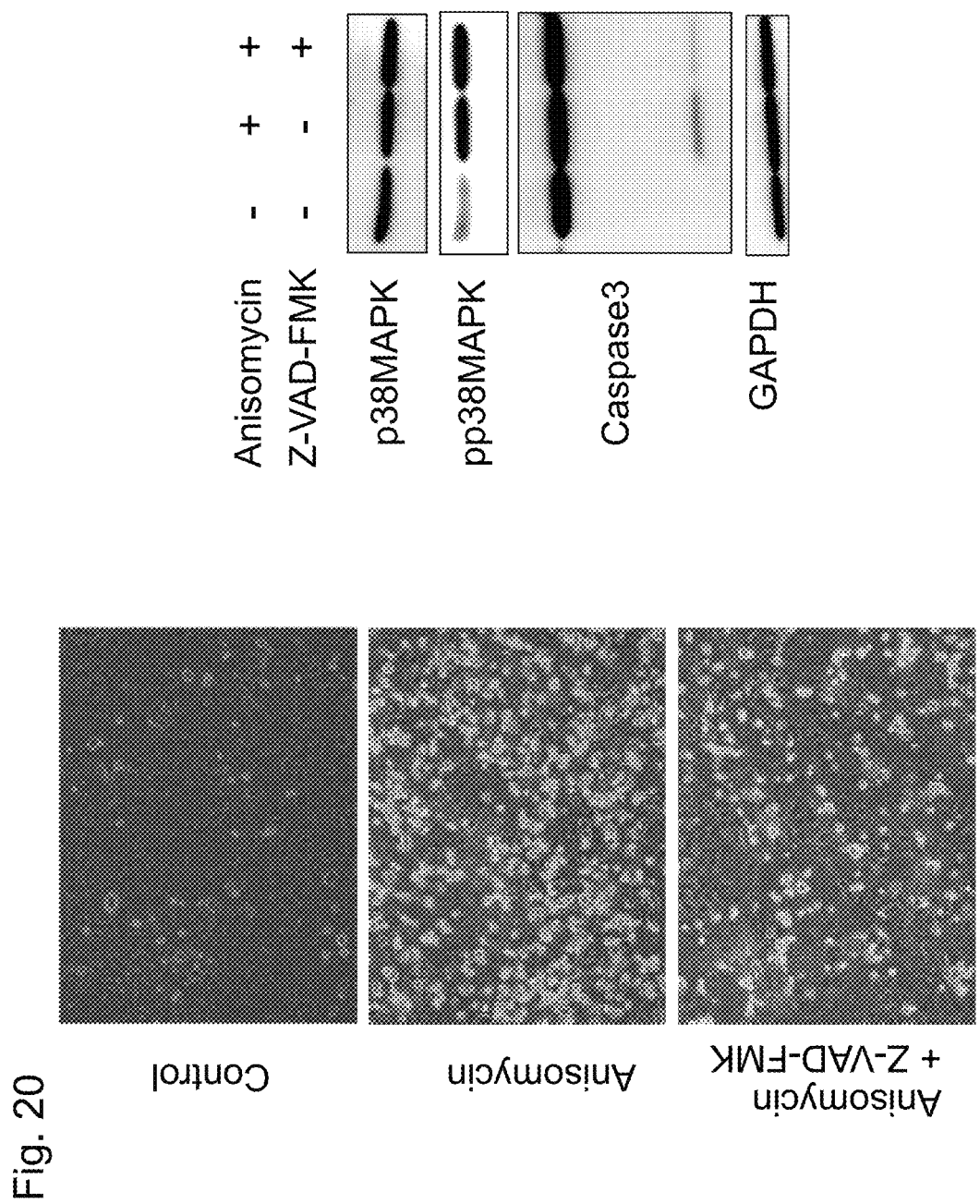
FIG. 20 shows that p38 MAPK activation induces apoptosis. The left panel is a picture from observation of cell form under a phase difference microscope (after 9 hours). From the top, the control, anisomycin group, and anisomycin and Z-VAD-FMK group are shown. The results are shown in the right panel from collecting proteins from the cells and comparing the amount of expression of proteins by Western Blot after 9 hours. The expression of p38 MAPK, phosphorylated p38 MAPK, Caspase 3 and GADPH (control) is shown from the top. From the left column, a sample without adding anisomycin or Z-VAD-FMK (control), sample added with only anisomycin, and sample added with both anisomycin and Z-VAD-FM are shown.

The results are shown in FIG. 20. Phosphorylation of p38 due to anisomysin having p38 activation action is observed, and activation due to cleavage of caspase 3 is also observed. Caspase 3 activation was suppressed by a caspase inhibitor Z-VAD-FMK. The above results show that p38 activation induces apoptosis. Since p38 MAPK activation was demonstrated to induce corneal endothelial apoptosis, this fact also demonstrates that the p38 MAPK inhibitor of the present invention causes promotion of corneal endothelial cell proliferation and suppression of corneal endothelial cell disorder, and therefore can be used as a corneal endothelial therapeutic drug.

Example 11

P38 MAPK Inhibitor Eye Drops Test in Monkey Corneal Endothelial Partial Disorder Model After a stainless steel bar with a diameter of 7 mm was cooled with liquid nitrogen, the bar was contacted with the corneal in both eyes of 2 cynomolgus monkeys (purchased from Shiga University of Medical Science). About 7 mm in diameter of the corneal endothelium fell off to make a partial disorder model.

50 μl of SB203580 (3 mM) eyedrops was then administered into the right eye 4 times a day. Similarly, eye drops of abase agent, which is phosphate buffer solution, were administered into the left eye as the control.

A monkey model was made in this manner for use in the following experiment.

Example 12

Administration of SB203580 Eye Drops Promotes Proliferation of Primate Corneal Endothelium The present Example demonstrated that administration of SB203580 eye drops promotes proliferation of a primate corneal endothelium.

(Materials and Methods)
(Observation of Expression by Immunostaining)

Expression of Ki-67 associated with cell proliferation was confirmed to be elevated after administration of SB203580 eye drops by immunostaining. The methodology of immunostaining was in accordance with the above-described Preparation Example 2. The antibodies were changed to antibodies to Ki-67 to conduct the experiment.
*Antibodies to Ki-67 (M7240, Dako)

In short, the following was performed.

For a tissue staining inspection, cultured cells were immobilized with 4% formaldehyde for 10 minutes at room temperature (RT) and incubated for 60 minutes with 1% bovine serum albumin (BSA). The antibodies to Ki-67 were diluted 1:200 to conduct the inspection. For secondary antibodies, a 1:1000 dilution of Alexa Fluor® 488 labeling goat antimouse IgG (Life Technologies) was used. Cellular nuclei were then stained with DAPI (Cell stain DAPI Solution; Dojindo, Kumamoto, Japan). Slides were then observed under a fluorescence microscope (all-in-one fluorescence microscope, KEYENCE, Osaka, JAPAN).

Pictures of 5 views were taken for each of the right and left eyes to analyze the percentage of Ki67 positive cells.
(Results)

Figure 21:
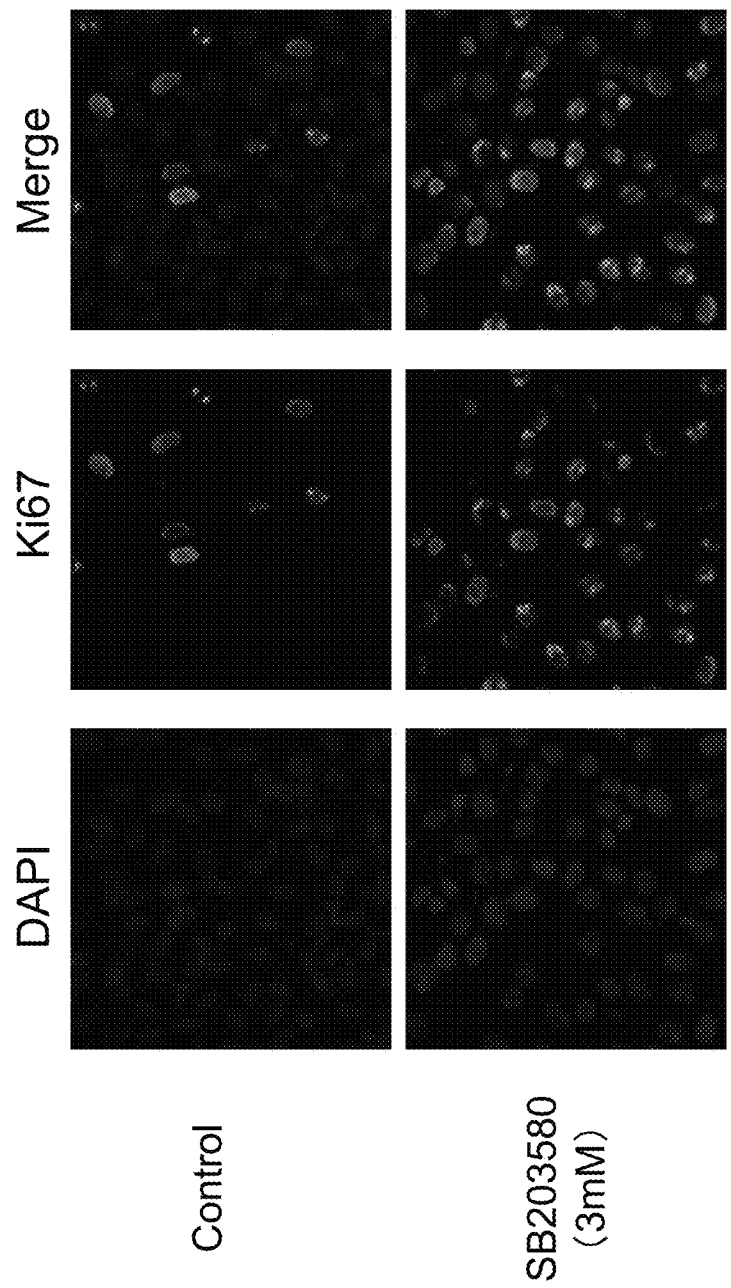
FIG. 21 shows that administration of SB203580 eye drops promotes proliferation of a primate corneal endothelium. Promotion of proliferation was confirmed by immunostaining. The top row shows the control, and the bottom row shows SB203580 (3 mM). From the left, pictures of DAPI staining, immunostaining with anti-Ki67 antibodies and merge are shown.
Figure 22:
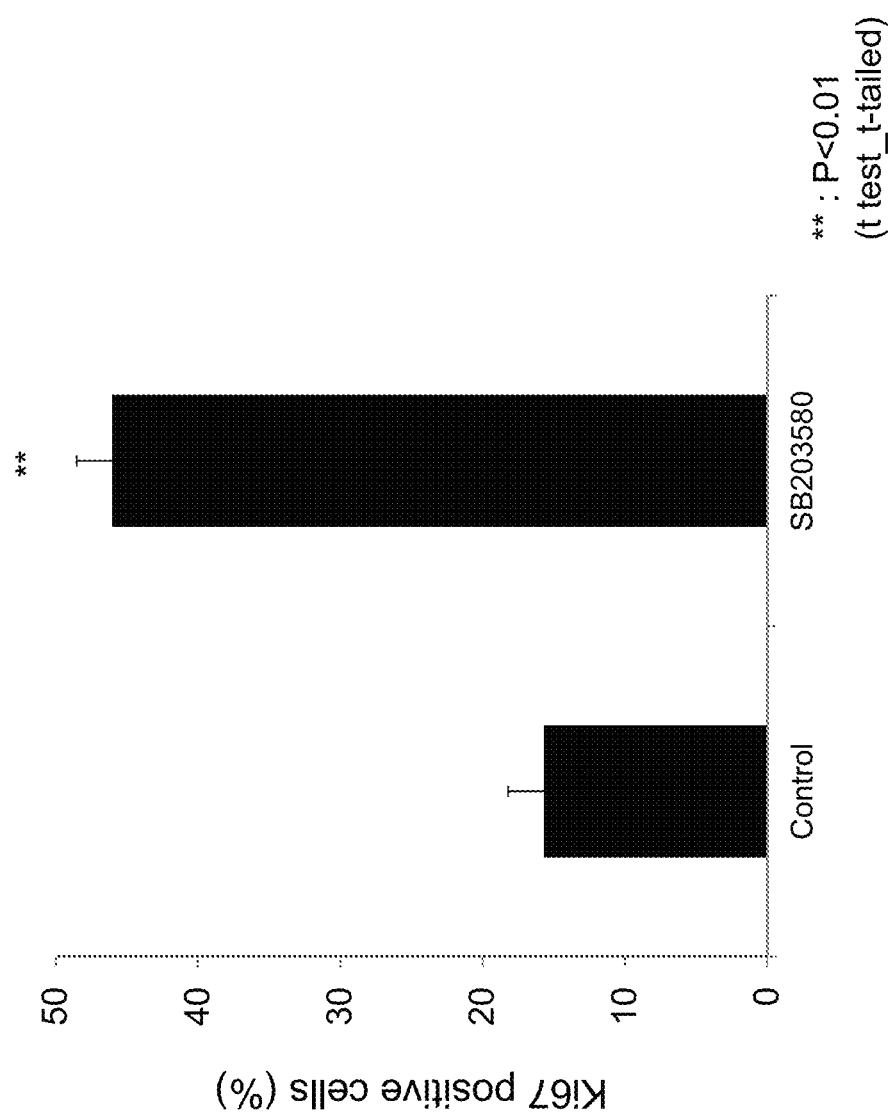
FIG. 22 shows that administration of SB203580 eye drops promotes proliferation of a primate corneal endothelium. The percentages of Ki67 positive cells in the control (left) and SB203580 (right) are shown (y axis). When pictures for 5 views were taken for each of the right and left eyes to analyze the ratio of Ki67 positive cells, significantly more Ki67 positive cells were observed in the eyes with SB203580 eye drops administered. ** indicates p<0.01.

The results are shown in FIGS. 21 and 22.

Figure 23:
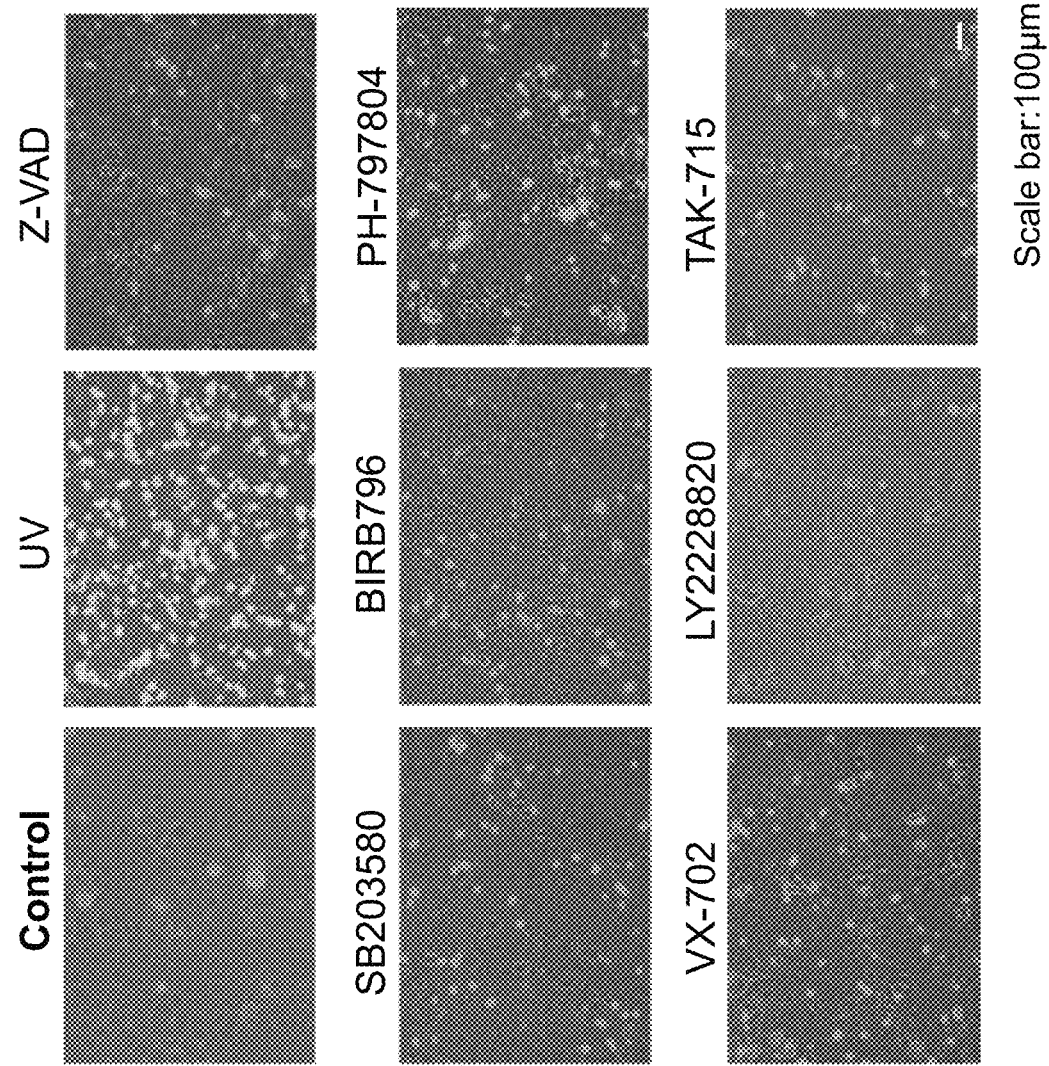
FIG. 23 shows that a p38 MAPK inhibitor suppresses cell death of cultured corneal endothelial cells. The top row, from the left, shows the control (addition of only DMSO), UV (100 J/m$^2$) and Z-VAD staining. The middle row shows, from the left, SB203580, BIRB796, and PH-797804. The bottom row shows, from the left, VX-702, LY2228820, and TAK-715. The concentration used was 10 µM for SB203580, 1 µM for Semapimod, 3 µM for BIRB796, 1 µM for PH-797804, 3 µM for VX-702, 3 µM for LY2228820, and 3 µM for TAK-715. Cellular disorders induced by UV were suppressed by all p38 MAPK inhibitors that were used. The scale bar indicates 100 µm.

FIG. 21 is a picture showing that administration of SB203580 eye drops promotes proliferation of primate corneal endothelia. FIG. 22 is a result of counting, which shows that administration of SB203580 eye drops promotes proliferation of primate corneal endothelia. As shown, more Ki67 positive cells were observed in the eye with SB203580 eye drops administered. Further, as shown in FIG. 23, significantly more Ki67 positive cells were observed in the eye with SB203580 eye drops administered when the percentage of Ki67 positive cells was analyzed. The same tendency was observed in both of the two monkeys. The above results show that a p38 MAPK inhibitor, from administration as eye drops or the like, acts on a corneal endothelium and promotes proliferation of corneal endothelial cells in primates in general.

Example 13

P38 MAPK Inhibitor Suppresses Cell Death of Cultured Corneal Endothelial Cells

Study of effect of p38 MAPK inhibitor on apoptosis of cultured monkey corneal endothelial cells $1 \times 10^5$ cultured monkey corneal endothelial cells were seeded on a 12-well plate coated with an FNC Coating Mix and cultured for about 5 days until reaching confluence under the condition of 5% $CO_2$ at 37° C.

Medium: Dulbecco's Modified Eagle Medium (DMEM, Gibco, 12320-032), 10% FBS, 1% Penicillin-Streptomycin (nacalai tesque, 26252-94)

Each inhibitor was then added at the concentration in the above-described Table and the cells were incubated for 16 hours under the condition of 5% $CO_2$ at 37° C. The solvent of each reagent, Dimethyl Sulfoxide, Sterile-filtered (nacalai tesque, 13408-64) MSO, was added to the Control group and the UV group. Gibco DMEM, 1% P/S (penicillin/streptomycin) was used as the medium.

The cellular supernatant was then removed and the cells were irradiated with UV (100 $J/m^2$). After irradiation, cells were again added to a medium containing each inhibitor and cultured for 9 hours. The cell form and apoptosis were observed under a phase difference microscope.
(Results)

The results are shown in FIG. 23. As shown for all p38 MAPK inhibitors, p38 MAPK inhibitors were shown to suppress death of cultured corneal endothelial cells.

Example 14

P38 MAPK Inhibitor Suppresses Apoptosis of Cultured Corneal Endothelial Cells

The cells, after 9 hours of culture, were stained for 20 minutes at 37° C. by using MEBCYTO-Apoptosis Kit (Annexin V-FITC Kit) (manufacturer: MBL, Code: 4700). The cells were then immobilized for 10 minutes with 95% acetic acid ethanol. After immobilization, the cells were stained for 30 minutes with DAPI Solution (manufacturer: DOJINDO, Code: GA098) and observed under a confocal microscope.
(Results)

Figure 24:
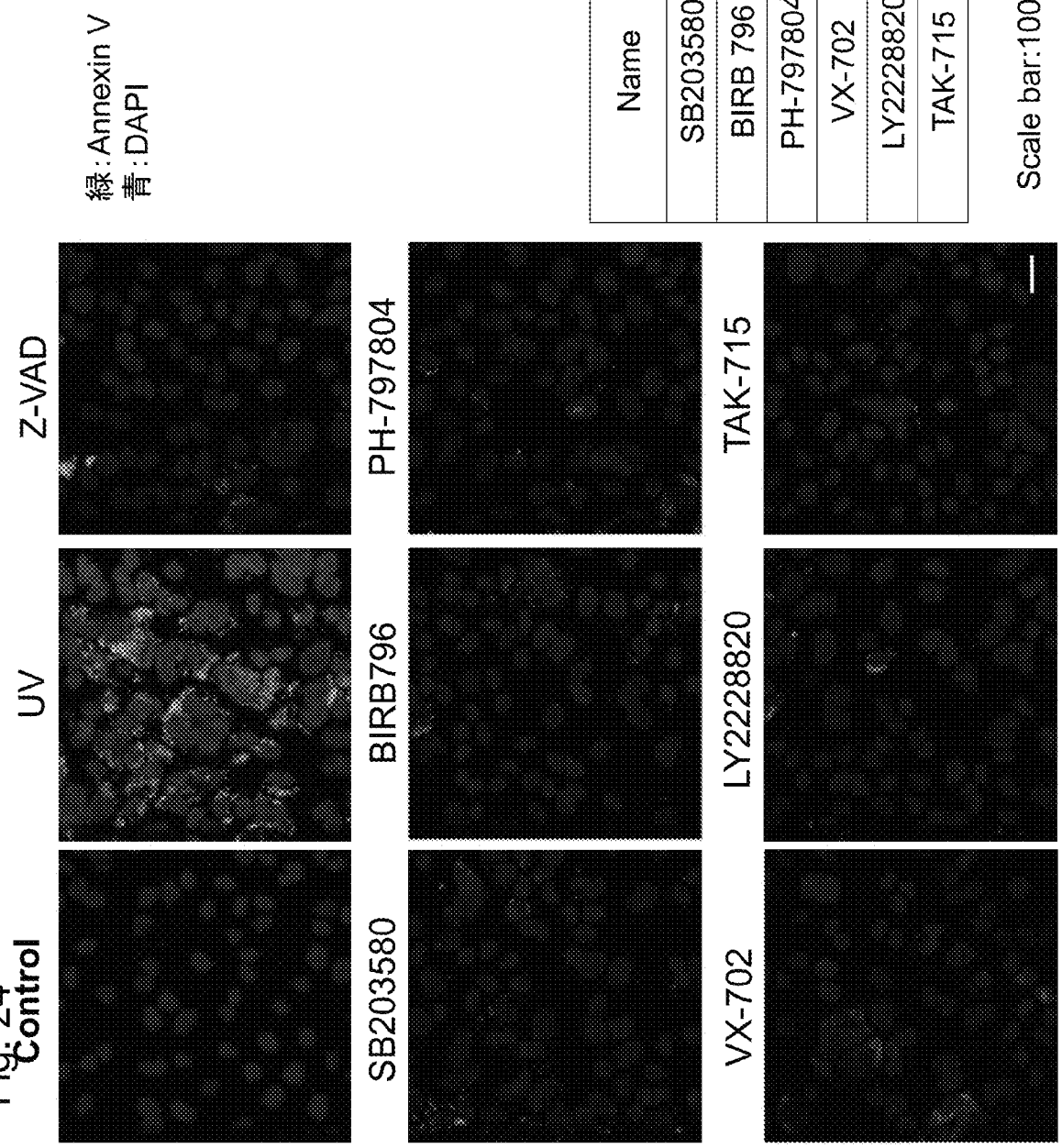
FIG. 24 shows that a p38 MAPK inhibitor suppresses apoptosis of cultured corneal endothelial cells. The top row, from the left, shows the control (addition of only DMSO), UV (100 J/m$^2$) and Z-VAD staining. The middle row shows, from the left, SB203580, BIRB796, and PH-797804. The bottom row shows, from the left, VX-702, LY2228820, and TAK-715. Green staining indicates annexin V, and blue staining indicates DAPI staining. Apoptosis induced by UV was suppressed by all p38 MAPK inhibitors that were used. The scale bar indicates 100 µm.

The results are shown in FIG. 24. As shown for all p38 MAPK inhibitors, p38 MAPK inhibitors were shown to suppress death of cultured corneal endothelial cells.

Example 15

P38 MAPK Inhibitor Suppresses Apoptosis of Corneal Endothelium

The present Example demonstrated that a p38 MAPK inhibitor suppresses apoptosis of a corneal endothelium.
(Materials and Methods)

The experiment used a rabbit eye ball 0-24 hours after euthanasia. Sclerocornea was removed along the corneal limbus under a stereo microscope by using spring scissors. The crystalline lens and iris were removed to make a sclerocornea segment. The sclerocornea segment was divided into 4 for a control group and a group added with an agent similar to SB203580. After dividing a cornea, pretreatment was applied to the Control group for 2 hours in the dark with Optisol-GS® (Bausch & Lomb) (Lot. W0006098) added with DMSO and to the group added with an agent similar to SB203580 with Optisol-GS® added with each reagent. After washing the cornea twice with PBS(–), 100

J/m² of UV was irradiated onto the corneal endothelial cells, which were against stored for 24 hours at 4° C. As the storing solution, DMSO was used for the Control group and Optisol-GS® added with each reagent was used for each of the groups added with an agent similar to SB203580. The sclerocornea segments were washed with PBS(−), and MEBCYTO-Apoptosis kit (Annexin V-FITC kit) (MBL) (Lot. 027FA) was used for Annexin V and DAPI staining. The segments were immersed and immobilized for 30 minutes in −30° C. ice-cooled 95% ethanol. In order to remove ethanol components, PBS(−) was exchanged every 5 minutes and the segments were washed three times. An antifading agent was then added and enclosed. Annexin V and nuclei was observed by fluorescence imaging under a confocal microscope.

The percentage of Annexin V positive cells were calculated in the above-described rabbit corneal tissue. *$p<0.05$ (Dunnett's test).

(Results)

Figure 25:
FIG. 25 shows that a p38 MAPK inhibitor suppresses apoptosis of a corneal endothelium.
Figure 25:
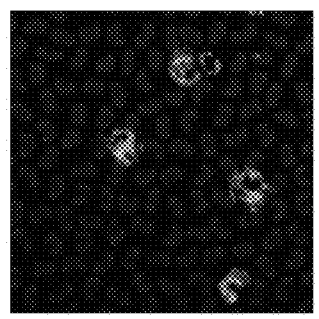
Figure 25:
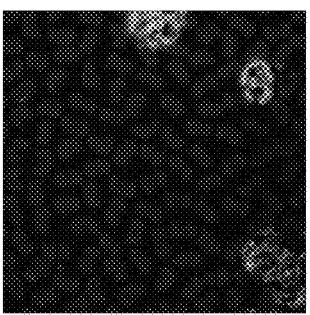
Figure 25:
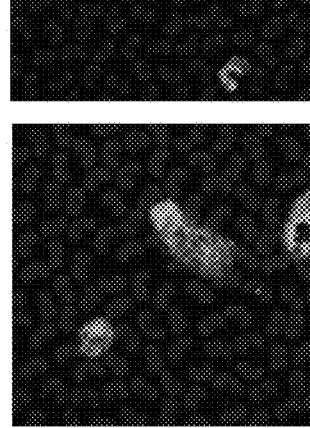
Figure 25:
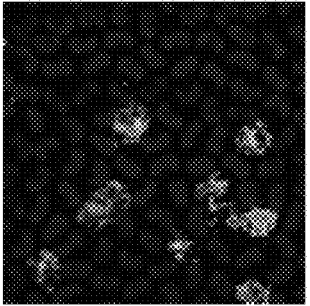
Figure 26:
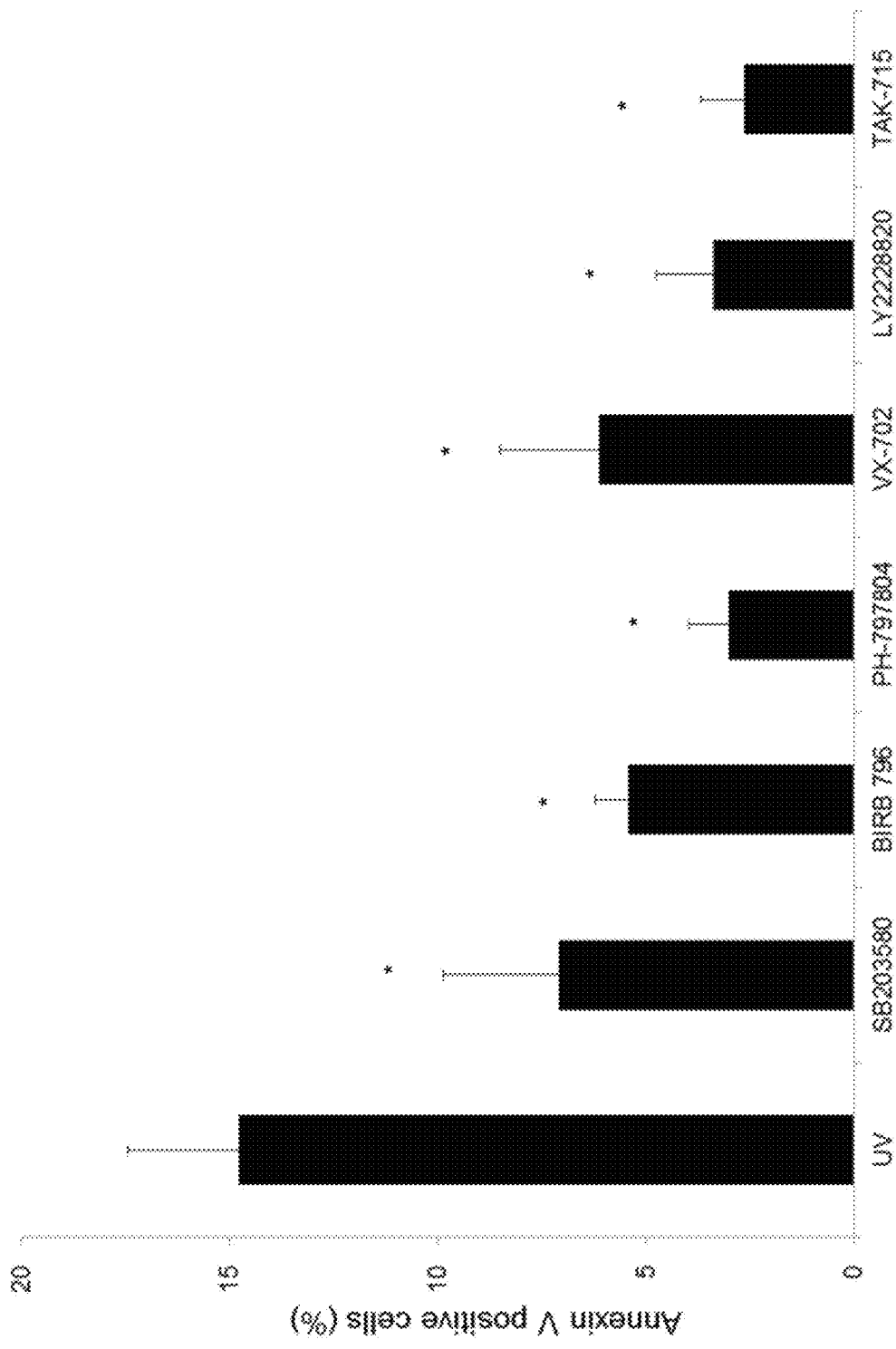
FIG. 26 shows that a p38 MAPK inhibitor suppresses apoptosis of a corneal endothelium. The percentage of Annexin V positive cells is shown. From the left, UV irradiation, SB203580, BIRB796, PH-707804, VX-702, LY2228820, and TAK715 are shown. Dunnett's test was used for the test. * indicates p<0.05.

The results of observing Annexin V and nuclei by fluorescence imaging are shown in FIG. 25. As shown for all p38 MAPK inhibitors, p38 MAPK inhibitors were shown to suppress apoptosis of corneal endothelia. Further, the results of calculating the percentage of Annexin V positive cells are shown in FIG. 26. Relative to the control irradiated with UV, the percentage of Annexin V positive cells significantly decreased by all p38 MAPK inhibitors. The above results demonstrate that p38 MAPK inhibitors have an effect of suppressing apoptosis of a corneal endothelium.

Example 16

Examples of Other Dosing Form of p38 MAP Kinase Inhibitor

The present Example uses the p38 MAP kinase inhibitor SB203580 to confirm whether anterior chamber administration, subconjunctival injection, anterior chamber or subconjunctival injection by including an agent in a sustained release agent or the like is possible. The following protocols were used for such dosing form.

Anterior chamber administration: A formulation prepared in the following manner is injected into the anterior chamber by a common method.

Preparation Example of an Agent to be Administered

An agent (e.g., SB203580) is prepared by diluting the agent with saline or purified water.

Subconjunctival injection: A formulation prepared in the following manner is injected into the anterior chamber by a common method.

An agent (e.g., SB203580) is prepared by diluting the agent with saline or purified water.

Anterior Chamber Administration with a Sustained Release Agent:

An agent (e.g., S8203580) is impregnated into a sustained release agent using a carrier such as gelatin or polylactic acid and is injected into the anterior chamber.

Subconjunctival Administration with a Sustained Release Agent:

An agent (e.g., SB203580) is impregnated into a sustained release agent using a carrier such as gelatin or polylactic acid and is subconjunctivally injected.

These administration methods are also expected to achieve therapy and prevention of progression of corneal endothelial disorder as in the above-described Examples.

Example 17

Eye Drops as Formulation Example

The composition of tested substances at each concentration is shown below.

SB203580 (available from CALBIOCHEM, catalog number: 559389 or the like) or SB203580 hydrochloride (available from Wako Pure Chemical Industries (193-15611) or the like) or other p38 MAP kinase inhibitors: 0.003 g, 0.01 g, 0.03 g, 0.05 g or 0.1 g (dosage as dehydrochlorinated form)

| | |
|---|---|
| Sodium chloride | 0.85 g |
| Sodium dihydrogen phosphate dihydrate | 0.1 g |
| Benzalkonium chloride | 0.005 g |
| Sodium hydroxide | appropriate amount |
| Purified water | appropriate amount |
| Total amount | 100 mg (pH 7.0). |

Eye drops can also be diluted with a base agent.
The following is a representative composition of the base. However, the composition can be appropriately changed.

| | |
|---|---|
| Sodium chloride | 0.85 g |
| Sodium dihydrogenphosphate dihydrate | 0.1 g |
| Benzalkonium chloride | 0.005 g |
| Sodium hydroxide | appropriate amount |
| Purified water | appropriate amount |
| Total amount | 100 mg (pH 7.0) |

As described above, the present invention is exemplified by the use of its preferred Embodiments. However, it is understood that the scope of the present invention should be interpreted solely based on the claims. It is also understood that any patent, any patent application, and any references cited herein should be incorporated by reference in the present specification in the same manner as the contents are specifically described herein. The present application claims priority to Japanese Patent Application No. 2013-235768.

INDUSTRIAL APPLICABILITY

The present invention provides a therapeutic or prophylactic drug for a corneal endothelial disorder requiring cell proliferation, especially a therapeutic or prophylactic technique for corneal endothelial wound. The present invention provides a technique available in industries (pharmaceutical or the like) involved in techniques associated with formulation or the like based on such a technique.

[Sequence Listing Free Text]

```
IL6-F:
SEQ ID NO: 1:
CACAAGCGCCTTCGGTCCAGTT

IL6-R:
SEQ ID NO: 2:
TCTGCCAGTGCCTCTTTGCTGC

GAPDH-F:
SEQ ID NO: 3:
GAGTCAACGGATTTGGTCGT

GAPDH-R:
SEQ ID NO: 4:
TTGATTTTGGAGGGATCTCG
```

The invention claimed is:

1. A method of treating Fuchs' endothelial corneal dystrophy, comprising administering an effective amount of a p38 MAP kinase inhibitor at a concentration of 3 mM to 10 mM to a subject in need thereof, wherein the p38 MAP kinase inhibitor is 4-(4-fluorophenyl)-2-(4-methylsulfinylphenyl)-5-(4-pyridyl)-1H-imidazole (SB203580) or a salt thereof, and the method is effective to increase cell proliferation of corneal endothelial cells.

2. The method of claim 1, wherein the p38 MAP kinase inhibitor is water-soluble.

3. The method of claim 1, wherein the p38 MAP kinase inhibitor is 4-(4-fluorophenyl)-2-(4-methylsulfinylphenyl)-5-(4-pyridyl)-1H-imidazole (SB203580) hydrochloride.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial
<220> FEATURE:
<223> OTHER INFORMATION: IL6-F primer

<400> SEQUENCE: 1
cacaagcgcc ttcggtccag tt                                              22

<210> SEQ ID NO 2
<211> LENGTH: 22
<212> TYPE: DNA
<213> ORGANISM: Artificial
<220> FEATURE:
<223> OTHER INFORMATION: IL6-R primer

<400> SEQUENCE: 2
tctgccagtg cctctttgct gc                                              22

<210> SEQ ID NO 3
<211> LENGTH: 20
<212> TYPE: DNA
<213> ORGANISM: Artificial
<220> FEATURE:
<223> OTHER INFORMATION: GAPDH-F

<400> SEQUENCE: 3
gagtcaacgg atttggtcgt                                                 20

<210> SEQ ID NO 4
<211> LENGTH: 20
<212> TYPE: DNA
<213> ORGANISM: Artificial
<220> FEATURE:
<223> OTHER INFORMATION: GAPDH-R

<400> SEQUENCE: 4
ttgattttgg agggatctcg                                                 20
```